United States Patent
Scheinberg et al.

(10) Patent No.: US 9,233,149 B2
(45) Date of Patent: *Jan. 12, 2016

(54) WT1 HLA CLASS II—BINDING PEPTIDES AND COMPOSITIONS AND METHODS COMPRISING SAME

(71) Applicant: SLOAN KETTERING INSTITUTE FOR CANCER RESEARCH, New York, NY (US)

(72) Inventors: David A. Scheinberg, New York, NY (US); Javier Pinilla-Ibarz, Tampa, FL (US); Rena May, Baltimore, MD (US)

(73) Assignee: SLOAN KETTERING INSTITUTE FOR CANCER RESEARCH, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/028,329

(22) Filed: Sep. 16, 2013

(65) Prior Publication Data

US 2014/0220054 A1 Aug. 7, 2014

Related U.S. Application Data

(63) Continuation of application No. 12/083,731, filed as application No. PCT/US2006/040719 on Oct. 17, 2006, now Pat. No. 8,765,687.

(60) Provisional application No. 60/726,608, filed on Oct. 17, 2005, provisional application No. 60/728,304, filed on Oct. 20, 2005.

(51) Int. Cl.
*A61K 38/03* (2006.01)
*A61K 39/00* (2006.01)
*C07K 14/47* (2006.01)
*A61K 38/00* (2006.01)

(52) U.S. Cl.
CPC .......... *A61K 39/0011* (2013.01); *C07K 14/4748* (2013.01); *A61K 38/00* (2013.01); *A61K 2039/5158* (2013.01); *A61K 2039/57* (2013.01)

(58) Field of Classification Search
CPC ... A61K 39/0011; A61K 39/00; A61K 38/00; A61K 2039/5154; A61K 2039/5158; A61K 2039/55566; A61K 38/193; A61K 2039/572; C07K 14/4748; C07K 7/08; C07K 14/7051; C07K 14/435
See application file for complete search history.

(56) References Cited

U.S. PATENT DOCUMENTS 8,765,687 B2 * 7/2014 Scheinberg et al. ......... 514/21.4

OTHER PUBLICATIONS

Menssen et al. Wilms' tumor gene (WT1) expression in lung cancer, colon cancer and glioblastoma cell lines compared to freshly isolated tumor specimens. J Cancer Res Clin Oncol. Apr. 2000;126(4):226-32.*
Watson et al. A prophylactic vaccine for breast cancer? Breast Cancer Res. 2010;12(4):310.*
Kaida et al. Phase 1 trial of Wilms tumor 1 (WT1) peptide vaccine and gemcitabine combination therapy in patients with advanced pancreatic or biliary tract cancer. J Immunother. Jan. 2011;34(1):92-9.*
Kelly et al. Lung cancer vaccines. Cancer J. Sep.-Oct. 2011;17(5):302-8.*
Maslak, Peter A, et al. "Vaccination with synthetic analog peptides derived from WT1 oncoprotein induces T-cell responses in patients with complete remission from acute myeloid leukemia." *Blood* 116.2 (2010): 171-179.
Krug, Lee M., et al. "WT1 peptide vaccinations induce CD4 and CD8 T cell immune responses in patients with mesothelioma and non-small cell lung cancer." *Cancer immunology, immunotherapy* 59.10 (2010): 1467-1479.

* cited by examiner

*Primary Examiner* — Karlheinz R Skowronek
*Assistant Examiner* — Jia-Hai Lee
(74) *Attorney, Agent, or Firm* — Mark S. Cohen; Pearl Cohen Zedek Latzer Baratz LLP

(57) ABSTRACT

This invention provides WT1 peptides and methods of treating, reducing the incidence of, and inducing immune responses against a WT1-expressing cancer, comprising same.

21 Claims, 12 Drawing Sheets

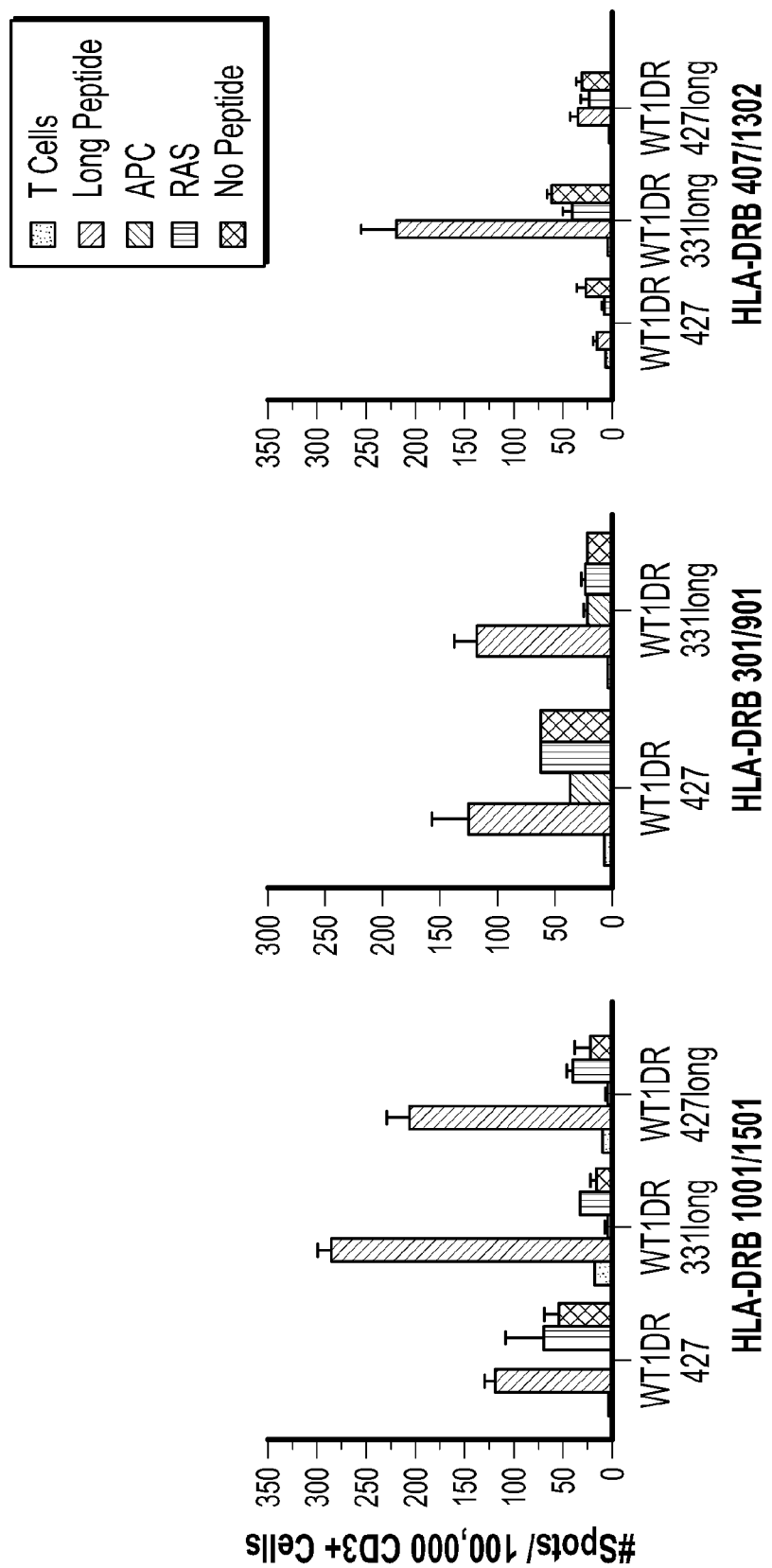
FIG. 5 (Part 1)

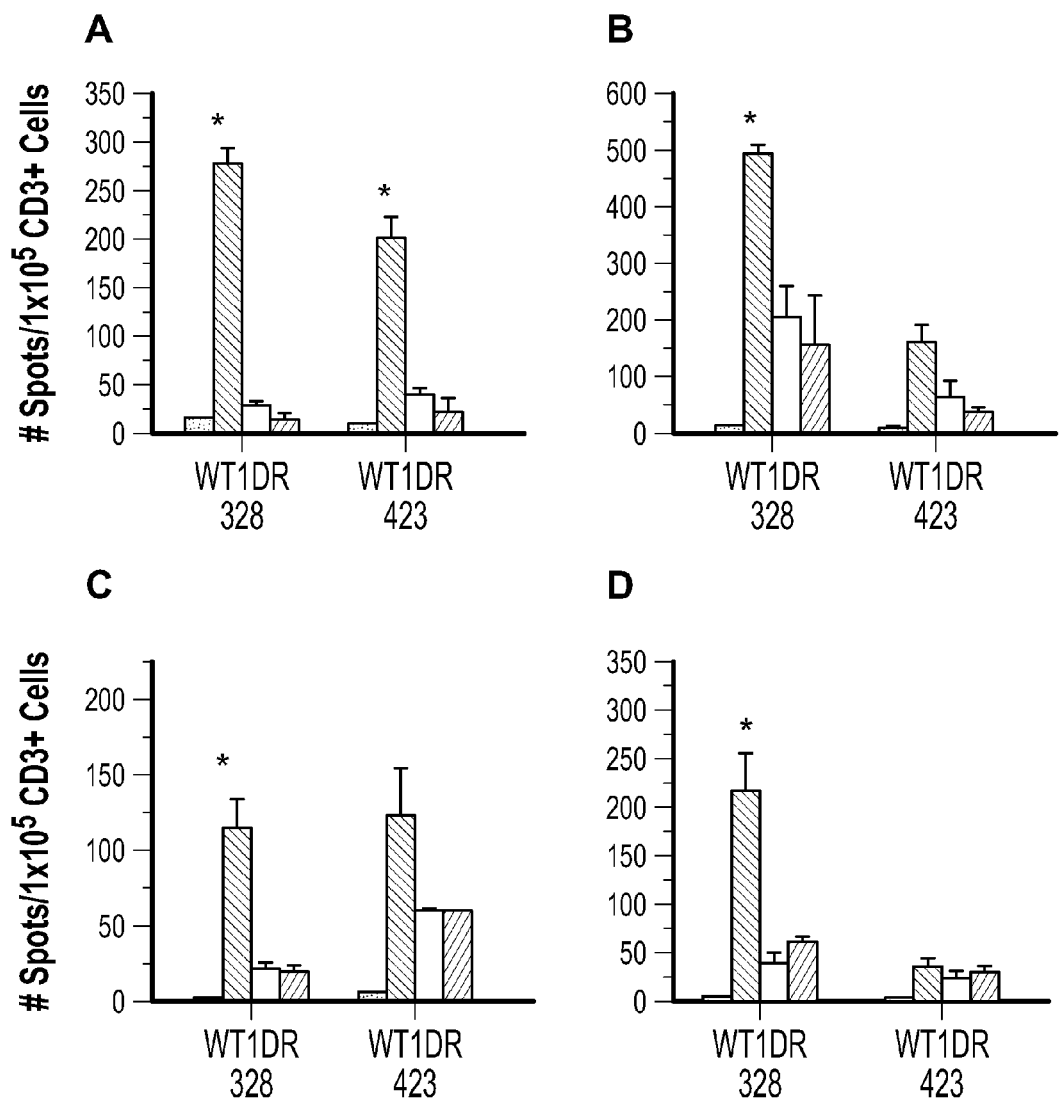
FIG. 5 (Part 2)

WT1 HLA CLASS II—BINDING PEPTIDES AND COMPOSITIONS AND METHODS COMPRISING SAME

CROSS-REFERENCE TO RELATED APPLICATIONS

This application is a continuation of U.S. patent application Ser. No. 12/083,731, filed Sep. 27, 2009, issued as U.S. Pat. No. 8,765,687, which is a National Phase Application of PCT International Application No. PCT/US06/40719, International Filing Date Oct. 17, 2006, claiming priority to US Provisional Patent Applications, 60/726,608, filed Oct. 17, 2005, and 60/728,304, filed Oct. 20, 2005.

FIELD OF INVENTION

This invention provides WT1 peptides and methods of treating, reducing the incidence of, and inducing immune responses against a WT1-expressing cancer, comprising same.

BACKGROUND OF THE INVENTION

Wilms tumor (WT), a pediatric nephroblastoma that occurs with a frequency of 1 in 10,000 births, has been the subject of intense clinical and basic research for several years. The tumor is embryonic in origin, it is detected in children usually during the first 5 years of life and can occur unilaterally or bilaterally. A WT arises when condensed metanephric mesenchymal cells of the developing kidney fail to properly differentiate. The implication of the Wilms tumor 1 (WT1) tumor suppressor gene in the etiology of WT illustrated the impact that genetic alterations can have on both development and tumorigenesis.

SUMMARY OF THE INVENTION

This invention provides WT1 peptides and methods of treating, reducing the incidence of, and inducing immune responses against a WT1-expressing cancer, comprising same.

In one embodiment, the present invention provides an isolated WT1 peptide having an amino acid (AA) sequence comprising the sequence RSDELVRHHNMHQRNMTKL (SEQ ID No: 2). In another embodiment, the AA sequence of the isolated WT1 peptide consists of SEQ ID No: 2. In another embodiment, the AA sequence of the isolated WT1 consists of a fragment of SEQ ID No: 2. Each possibility represents a separate embodiment of the present invention.

In another embodiment, the present invention provides an isolated WT1 peptide having an AA sequence comprising the sequence PGCNKRYFKLSHLQMHSRKHTG (SEQ ID No: 4). In another embodiment, the AA sequence of the isolated WT1 peptide consists of SEQ ID No: 4. In another embodiment, the AA sequence of the isolated WT1 consists of a fragment of SEQ ID No: 4. Each possibility represents a separate embodiment of the present invention.

In another embodiment, the present invention provides a composition comprising (a) an antigen-presenting cell and (b) a peptide selected from RSDELVRHHNMHQRNMTKL (SEQ ID No: 2) and PGCNKRYFKLSHLQMHSRKHTG (SEQ ID No: 4).

In another embodiment, the present invention provides a method of treating a subject with a WT1-expressing cancer, the method comprising administering to the subject a WT1 vaccine of the present invention, thereby treating a subject with a WT1-expressing cancer.

In another embodiment, the present invention provides a method of reducing the incidence of a WT1-expressing cancer, or its relapse, in a subject, the method comprising administering to the subject a WT1 vaccine of the present invention, thereby reducing the incidence of a WT1-expressing cancer, or its relapse, in a subject.

In another embodiment, the present invention provides a method of inducing an anti-mesothelioma immune response in a subject, the method comprising the step of contacting the subject with an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby inducing an anti-mesothelioma immune response in a subject.

In another embodiment, the present invention provides a method of treating a subject with a mesothelioma, the method comprising the step of administering to the subject an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby treating a subject with a mesothelioma.

In another embodiment, the present invention provides a method of reducing an incidence of a mesothelioma, or its relapse, in a subject, the method comprising the step of administering to the subject an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby reducing an incidence of a mesothelioma, or its relapse, in a subject.

BRIEF DESCRIPTION OF THE FIGURES

FIG. 5, part 1. Gamma IFN ELISPOT after stimulation with WT1 peptides of CD3+ T cells from healthy donors with different HLA-DRB1 types. Y axis:percentage of cytotoxicity. X axis:effector cell:target cell ratio. Part 2. CD3+ T cells (A: HLA-DRB1*1001/1501; B: HLA-DRB1*0701/1202; C: HLA-DRB1*0301/901; D: HLA-DRB1*0407/1302) were stimulated twice with peptide WT1 DR 328 or WT1DR 423. Stimulated T cells were challenged in an IFN-gamma ELISPOT assay with the following: Grey Bars: unchallenged control; Black Bars: CD14+ cells pulsed with stimulating peptide (either WT1DR 328 or WT1DR 423); White Bars: CD14+ cells pulsed with irrelevant CD4+ peptide epitope (RAS); Hatched Bars: unpulsed CD14+ cells. *–p<0.05 compared to controls. Y axis: number of spots per 1×10⁵ CD3+ T cells. X axis: peptide used for T cell stimulations.

DETAILED DESCRIPTION OF THE INVENTION

Figure 1A:
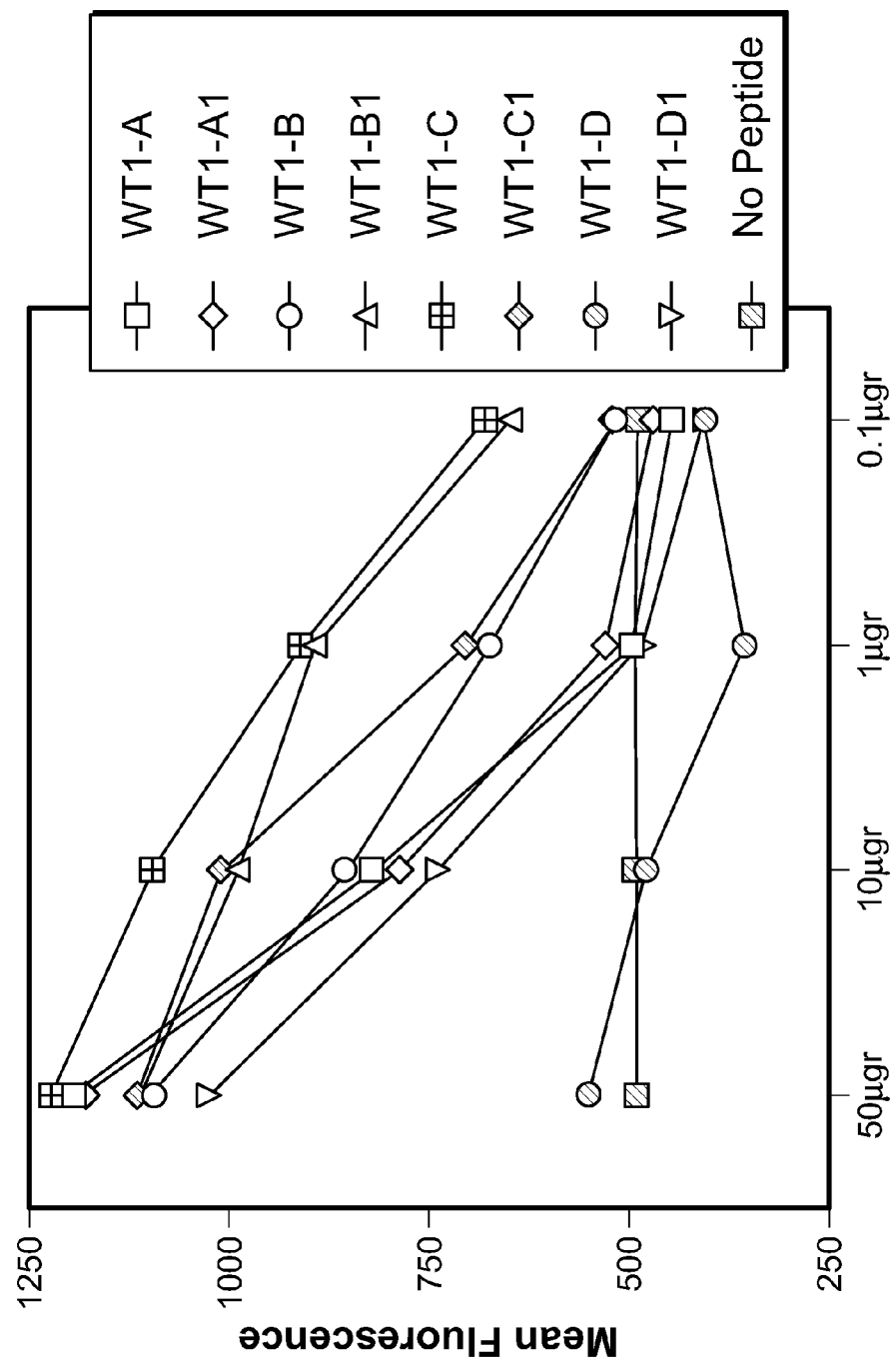
FIG. 1: T2 stabilization assay of native and synthetic WT-1 peptides to HLA A0201 cells (A) and HLA A0301 cells (B-E). Fluorescence index is ratio between median fluorescence with peptide tested:median fluorescence with no peptide. X axis:concentration per well of the peptide tested.
Figure 1B:
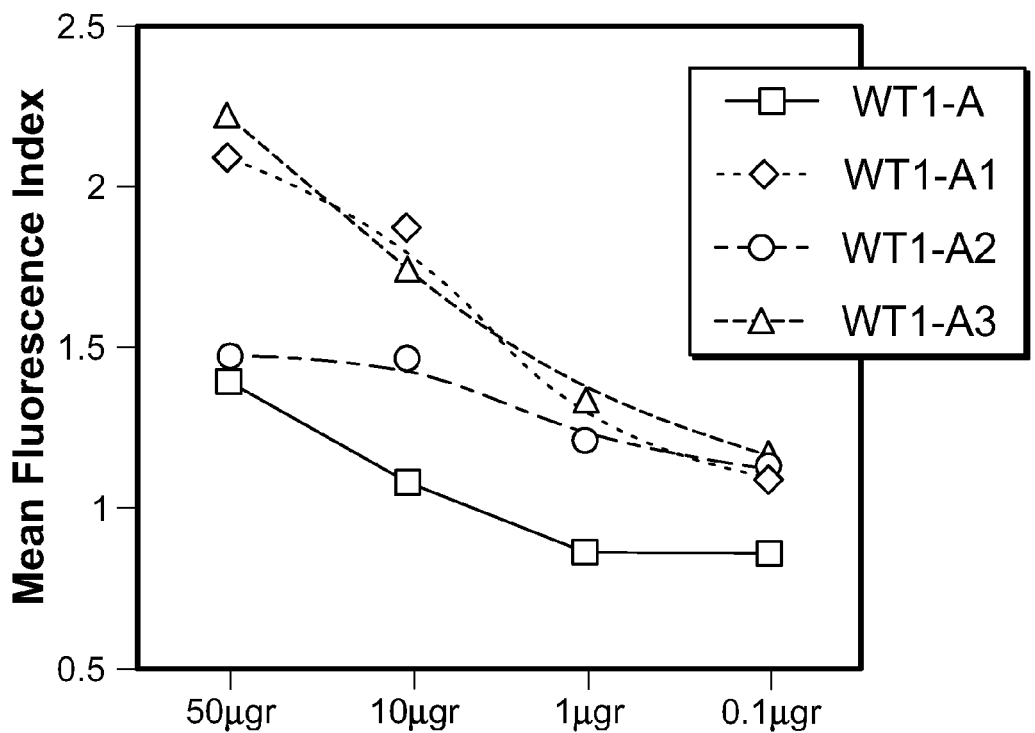
Figure 1C:
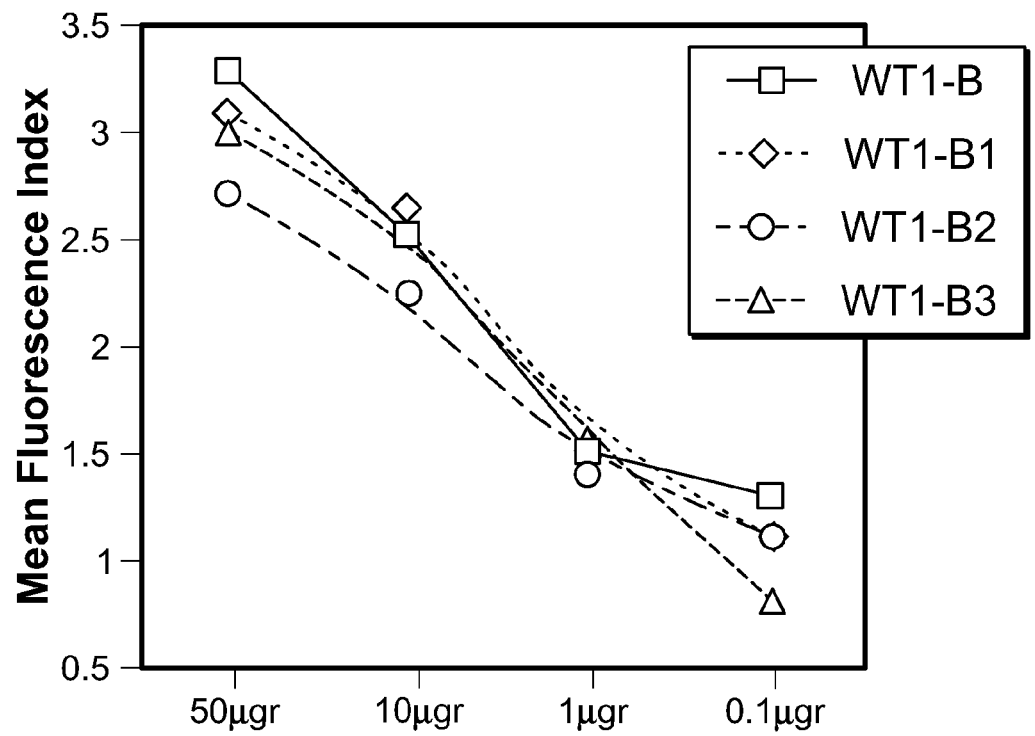
Figure 1D:
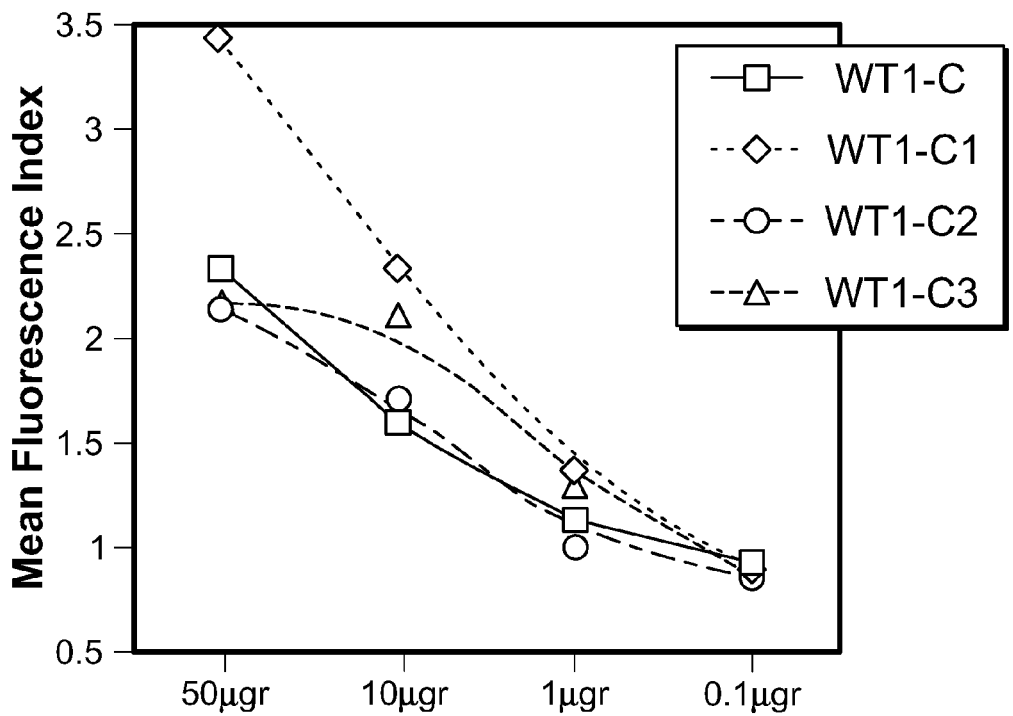
Figure 1E:
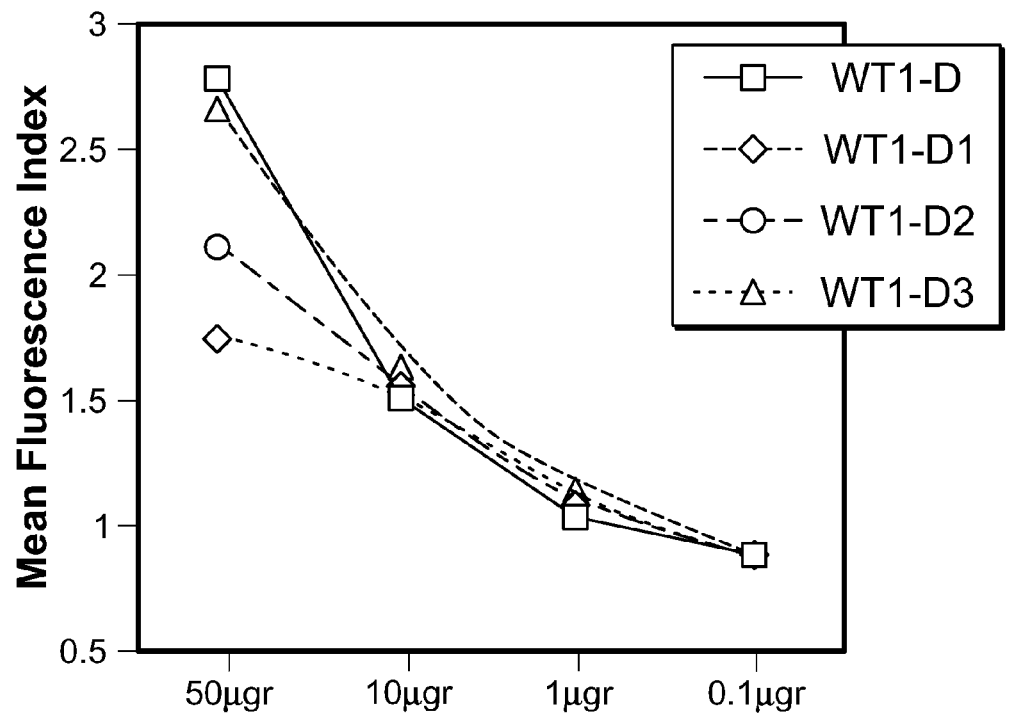

This invention provides WT1 peptides and methods of treating, reducing the incidence of, and inducing immune responses against a WT1-expressing cancer, comprising same.

As provided herein, peptides of the present invention elicit CD4+ T cell responses (Examples 3-4).

In one embodiment, the present invention provides an isolated WT1 peptide having an amino acid (AA) sequence comprising the sequence RSDELVRHHNMHQRNMTKL (SEQ ID No: 2). In another embodiment, the AA sequence of the isolated WT1 peptide consists of SEQ ID No: 2. In another embodiment, the AA sequence of the isolated WT1 consists of a fragment of SEQ ID No: 2. Each possibility represents a separate embodiment of the present invention.

In another embodiment, the present invention provides an isolated WT1 peptide having an AA sequence comprising the sequence PGCNKRYFKLSHLQMHSRKHTG (SEQ ID No: 4). In another embodiment, the AA sequence of the isolated WT1 peptide consists of SEQ ID No: 4. In another embodiment, the AA sequence of the isolated WT1 consists of a fragment of SEQ ID No: 4. Each possibility represents a separate embodiment of the present invention.

In another embodiment, the present invention provides an isolated WT1 peptide having an AA sequence comprising or consisting of SEQ ID No: 1, or consisting of a fragment of SEQ ID No: 1. In another embodiment, the present invention provides an isolated WT1 peptide having an AA sequence comprising or consisting of SEQ ID No: 3, or consisting of a fragment of SEQ ID No: 3. Each possibility represents a separate embodiment of the present invention.

In another embodiment, an isolated WT1 peptide of the present invention is unaltered (e.g. its sequence corresponds to a fragment of the WT1 protein, without in vitro introduction of mutations.

In another embodiment, the present invention provides a composition comprising (a) an antigen-presenting cell and (b) a peptide selected from RSDELVRHHNMHQRNMTKL (SEQ ID No: 2) and PGCNKRYFKLSHLQMHSRKHTG (SEQ ID No: 4). In another embodiment, the composition further comprises an additional HLA class II molecule-binding peptide. In another embodiment, the composition further comprise an HLA class I molecule-binding WT1 peptide. In another embodiment, the HLA class I molecule is an HLA-A molecule. In another embodiment, the AA sequence of the HLA class I molecule-binding WT1 peptide comprises a sequence selected from SEQ ID No: 5-38. In another embodiment, the AA sequence of the HLA class I molecule-binding WT1 peptide is from SEQ ID No: 5-38. Each possibility represents a separate embodiment of the present invention.

The WT1 protein of methods and compositions of the present invention can be any WT1 protein known in the art.

The WT1 molecule from which a peptide of the present invention is derived has, in another embodiment, the sequence:

```
(GenBank Accession number AY245105; SEQ ID No: 50)
MGSDVRDLNALLPAVPSLGGGGGCALPVSGAAQWAPVLDFAPPGASAYGSLGGPAPPPAPP

PPPPPPPHSFIKQEPSWGGAEPHEEQCLSAFTVHFSGQFTGTAGACRYGPFGPPPPSQASSGQA

RMFPNAPYLPSCLESQPAIRNQGYSTVTFDGTPSYGHTPSHHAAQFPNHSFKHEDPMGQQGS

LGEQQYSVPPPVYGCHTPTDSCTGSQALLLRTPYSSDNLYQMTSQLECMTWNQMNLGATLK

GVAAGSSSSVKWTEGQSNHSTGYESDNHTTPILCGAQYRIHTHGVFRGIQDVRRVPGVAPTL

VRSASETSEKRPFMCAYPGCNKRYFKLSHLQMHSRKHTGEKPYQCDFKDCERRFSRSDQLK
```

-continued
RHQRRHTGVKPFQCKTCQRKFSRSDHLKTHTRTHTGKTSEKPFSCRWPSCQKKFARSDELVR

HHNMHQRNMTKLQLAL.

In another embodiment, the WT1 molecule has the sequence:

(GenBank Accession number NM_000378; SEQ ID No: 51)
AAEASAERLQGRRSRGASGSEPQQMGSDVRDLNALLPAVPSLGGGGGCALPVSGAAQWAP

VLDFAPPGASAYGSLGGPAPPPAPPPPPPPPHSFIKQEPSWGGAEPHEEQCLSAFTVHFSGQF

TGTAGACRYGPFGPPPPSQASSGQARMFPNAPYLPSCLESQPAIRNQGYSTVTFDGTPSYGHT

PSHHAAQFPNHSFKHEDPMGQQGSLGEQQYSVPPPVYGCHTPTDSCTGSQALLLRTPYSSDN

LYQMTSQLECMTWNQMNLGATLKGHSTGYESDNHTTPILCGAQYRIHTHGVFRGIQDVRRV

PGVAPTLVRSASETSEKRPFMCAYPGCNKRYFKLSHLQMHSRKHTGEKPYQCDFKDCERRF

SRSDQLKRHQRRHTGVKPFQCKTCQRKFSRSDHLKTHTRTHTGEKPFSCRWPSCQKKFARS

DELVRHHNMHQRNMTKLQLAL.

In another embodiment, the WT1 molecule has the sequence:

(GenBank Accession number NP_077742; SEQ ID No: 52)
MQDPASTCVPEPASQHTLRSGPGCLQQPEQQGVRDPGGIWAKLGAAEASAERLQGRRSRGA

SGSEPQQMGSDVRDLNALLPAVPSLGGGGGCALPVSGAAQWAPVLDFAPPGASAYGSLGGP

APPPAPPPPPPPPHSFIKQEPSWGGAEPHEEQCLSAFTVHFSGQFTGTAGACRYGPFGPPPPSQ

ASSGQARMFPNAPYLPSCLESQPAIRNQGYSTVTFDGTPSYGHTPSHHAAQFPNHSFKHEDP

MGQQGSLGEQQYSVPPPVYGCHTPTDSCTGSQALLLRTPYSSDNLYQMTSQLECMTWNQM

NLGATLKGVAAGSSSSVKWTEGQSNHSTGYESDNHTTPILCGAQYRIHTHGVFRGIQDVRRV

PGVAPTLVRSASETSEKRPFMCAYPGCNKRYFKLSHLQMHSRKHTGEKPYQCDFKDCERRF

SRSDQLKRHQRRHTGVKPFQCKTCQRKFSRSDHLKTHTRTHTGEKPFSCRWPSCQKKFARS

DELVRHHNMHQRNMTKLQLAL.

In another embodiment, the WT1 molecule comprises the sequence:

(SEQ ID No: 53)
MGHHHHHHHHHHSSGHIEGRHMRRVPGVAPTLVRSASETSEKRPFMCAYPGCNKRYFKLS

HLQMHSRKHTGEKPYQCDFKDCERRFFRSDQLKRHQRRHTGVKPFQCKTCQRKFSRSDHLK

THTRTHTGEKPFSCRWPSCQKKFARSDELVRHHNMHQRNMTKLQLAL.

In another embodiment, the WT1 protein has the sequence set forth in GenBank Accession #NM_024426. In other embodiments, the WT1 protein has or comprises one of the sequences set forth in 1 of the following sequence entries: NM_024425, NM_024424, NM_000378, S95530, D13624, D12496, D12497, or X77549. In another embodiment, the WT1 protein has any other WT1 sequence known in the art.

"Peptide," in another embodiment of methods and compositions of the present invention, refers to a compound of subunit AA connected by peptide bonds. In another embodiment, the peptide comprises an AA analogue. In another embodiment, the peptide comprises a peptidomimetic. The different AA analogues and peptidomimetics that can be included in the peptides of methods and compositions of the present invention are enumerated hereinbelow. The subunits are, in another embodiment, linked by peptide bonds. In another embodiment, the subunit is linked by another type of bond, e.g. ester, ether, etc. Each possibility represents a separate embodiment of the present invention.

The unaltered and heteroclitic WT1 peptides of the present invention (as described both above and below) are referred to collectively herein as "WT1 peptides." Each of the embodiments enumerated below for "WT1 peptides" applies to unaltered WT1 peptides and HLA class I and class II heteroclitic peptides of the present invention. Each possibility represents a separate embodiment of the present invention.

In another embodiment, a WT1 peptide of the present invention binds to an HLA class II molecule. In another embodiment, the HLA class II molecule is an HLA-DRB molecule. In another embodiment, the HLA class II-molecule is an HLA-DRA molecule. In another embodiment, the HLA molecule is an HLA-DQA1 molecule. In another embodiment, the HLA molecule is an HLA-DQB1 molecule. In another embodiment, the HLA molecule is an HLA-DPA1 molecule. In another embodiment, the HLA molecule is an HLA-DPB1 molecule. In another embodiment, the HLA molecule is an HLA-DMA molecule. In another embodiment, the HLA molecule is an HLA-DMB molecule. In another embodiment, the HLA molecule is an HLA-DOA molecule. In another embodiment, the HLA molecule is an HLA-DOB molecule. In another embodiment, the HLA molecule is any other HLA class II-molecule known in the art. Each possibility represents a separate embodiment of the present invention.

In another embodiment, a WT1 peptide of methods and compositions of the present invention is so designed as to exhibit affinity for an HLA molecule. In another embodiment, the affinity is a high affinity, as described herein.

HLA molecules, known in another embodiment as major histocompatibility complex (MHC) molecules, bind peptides and present them to immune cells. Thus, in another embodiment, the immunogenicity of a peptide is partially determined by its affinity for HLA molecules. HLA class I molecules interact with CD8 molecules, which are generally present on cytotoxic T lymphocytes (CTL). HLA class II molecules interact with CD4 molecules, which are generally present on helper T lymphocytes.

In another embodiment, a peptide of the present invention is immunogenic. In another embodiment, "immunogenic" refers to an ability to stimulate, elicit or participate in an immune response. In another embodiment, the immune response elicited is a cell-mediated immune response. In another embodiment, the immune response is a combination of cell-mediated and humoral responses.

In another embodiment, T cells that bind to the MHC molecule-peptide complex become activated and induced to proliferate and lyse cells expressing a protein comprising the peptide. T cells are typically initially activated by "professional" antigen presenting cells ("APC"; e.g. dendritic cells, monocytes, and macrophages), which present costimulatory molecules that encourage T cell activation as opposed to anergy or apoptosis. In another embodiment, the response is heteroclitic, as described herein, such that the CTL lyses a neoplastic cell expressing a protein which has an AA sequence homologous to a peptide of this invention, or a different peptide than that used to first stimulate the T cell.

In another embodiment, an encounter of a T cell with a peptide of this invention induces its differentiation into an effector and/or memory T cell. Subsequent encounters between the effector or memory T cell and the same peptide, or, in another embodiment, with a related peptide of this invention, leads to a faster and more intense immune response. Such responses are gauged, in another embodiment, by measuring the degree of proliferation of the T cell population exposed to the peptide. In another embodiment, such responses are gauged by any of the methods enumerated hereinbelow.

In another embodiment, the peptides of methods and compositions of the present invention bind an HLA class II molecule with high affinity. In other embodiments, the HLA class II molecule is any HLA class II molecule enumerated herein. Each possibility represents a separate embodiment of the present invention.

In another embodiment, derivatives of peptides of methods and compositions of the present invention bind an HLA class I molecule with high affinity. In other embodiments, the MHC class I molecule is any MHC class I molecule enumerated herein. Each possibility represents a separate embodiment of the present invention.

In another embodiment, a peptide of methods and compositions of the present invention binds an HLA class II molecule with significant affinity, while a peptide derived from the original peptide binds an HLA class I molecule with significant affinity.

In another embodiment, "affinity" refers to the concentration of peptide necessary for inhibiting binding of a standard peptide to the indicated MHC molecule by 50%. In another embodiment, "high affinity" refers to an affinity is such that a concentration of about 500 nanomolar (nM) or less of the peptide is required for 50% inhibition of binding of a standard peptide. In another embodiment, a concentration of about 400 nM or less of the peptide is required. In another embodiment, the binding affinity is 300 nM. In another embodiment, the binding affinity is 200 nM. In another embodiment, the binding affinity is 150 nM. In another embodiment, the binding affinity is 100 nM. In another embodiment, the binding affinity is 80 nM. In another embodiment, the binding affinity is 60 nM. In another embodiment, the binding affinity is 40 nM. In another embodiment, the binding affinity is 30 nM. In another embodiment, the binding affinity is 20 nM. In another embodiment, the binding affinity is 15 nM. In another embodiment, the binding affinity is 10 nM. In another embodiment, the binding affinity is 8 nM. In another embodiment, the binding affinity is 6 nM. In another embodiment, the binding affinity is 4 nM. In another embodiment, the binding affinity is 3 nM. In another embodiment, the binding affinity is 2 nM. In another embodiment, the binding affinity is 1.5 nM. In another embodiment, the binding affinity is 1 nM. In another embodiment, the binding affinity is 0.8 nM. In another embodiment, the binding affinity is 0.6 nM. In another embodiment, the binding affinity is 0.5 nM. In another embodiment, the binding affinity is 0.4 nM. In another embodiment, the binding affinity is 0.3 nM. In another embodiment, the binding affinity is less than 0.3 nM.

In another embodiment, "affinity" refers to a measure of binding strength to the MHC molecule. In another embodiment, affinity is measured using a method known in the art to measure competitive binding affinities. In another embodiment, affinity is measured using a method known in the art to measure relative binding affinities. In another embodiment, the method is a competitive binding assay. In another embodiment, the method is radioimmunoassay or RIA. In another embodiment, the method is BiaCore analyses. In another embodiment, the method is any other method known in the art. In another embodiment, the method yields an IC50 in relation to an IC50 of a reference peptide of known affinity.

Each type of affinity and method of measuring affinity represents a separate embodiment of the present invention.

In another embodiment, "high affinity" refers to an IC50 of 0.5-500 nM. In another embodiment, the IC50 is 1-300 nM. In another embodiment, the IC50 is 1.5-200 nM. In another embodiment, the IC50 is 2-100 nM. In another embodiment, the IC50 is 3-100 nM. In another embodiment, the IC50 is 4-100 nM. In another embodiment, the IC50 is 6-100 nM. In another embodiment, the IC50 is 10-100 nM. In another embodiment, the IC50 is 30-100 nM. In another embodiment, the IC50 is 3-80 nM. In another embodiment, the IC50 is 4-60 nM. In another embodiment, the IC50 is 5-50 nM. In another embodiment, the IC50 is 6-50 nM. In another embodiment, the IC50 is 8-50 nM. In another embodiment, the IC50 is 10-50 nM. In another embodiment, the IC50 is 20-50 nM. In another embodiment, the IC50 is 6-40 nM. In another embodiment, the IC50 is 8-30 nM. In another embodiment, the IC50 is 10-25 nM. In another embodiment, the IC50 is 15-25 nM. Each affinity and range of affinities represents a separate embodiment of the present invention.

In another embodiment, a peptide of methods and compositions of the present invention binds to a superfamily of HLA molecules. Superfamilies of HLA molecules share very similar or identical binding motifs. In another embodiment, the superfamily is a HLA class I superfamily. In another embodiment, the superfamily is a HLA class II superfamily. Each possibility represents a separate embodiment of the present invention.

The terms "HLA-binding peptide," "HLA class I molecule-binding peptide," and "HLA class II molecule-binding peptide" refer, in another embodiment, to a peptide that binds an HLA molecule with measurable affinity. In another embodiment, the terms refer to a peptide that binds an HLA molecule with high affinity. In another embodiment, the terms refer to a peptide that binds an HLA molecule with sufficient affinity to activate a T cell precursor. In another embodiment, the terms refer to a peptide that binds an HLA molecule with sufficient affinity to mediate recognition by a T cell. The HLA molecule is, in other embodiments, any of the HLA molecules enumerated herein. Each possibility represents a separate embodiment of the present invention.

"Heteroclitic" refers, in another embodiment, to a peptide that generates an immune response that recognizes the original peptide from which the heteroclitic peptide was derived (e.g. the peptide not containing the anchor residue mutations). In another embodiment, "original peptide" refers to a peptide of the present invention. For example, YMFPNAPYL (SEQ ID No: 6), was generated from RMFPNAPYL (SEQ ID No: 5) by mutation of residue 1 to tyrosine (Examples). In another embodiment, "heteroclitic" refers to a peptide that generates an immune response that recognizes the original peptide from which the heteroclitic peptide was derived, wherein the immune response generated by vaccination with the heteroclitic peptide is greater than the immune response generated by vaccination with the original peptide. In another embodiment, a "heteroclitic" immune response refers to an immune response that recognizes the original peptide from which the improved peptide was derived (e.g. the peptide not containing the anchor residue mutations). In another embodiment, a "heteroclitic" immune response refers to an immune response that recognizes the original peptide from which the heteroclitic peptide was derived, wherein the magnitude of the immune response generated by vaccination with the heteroclitic peptide is greater than the immune response generated by vaccination with the original peptide. In another embodiment, the magnitude of the immune response generated by vaccination with the heteroclitic peptide is greater than the immune response substantially equal to the response to vaccination with the original peptide. In another embodiment, the magnitude of the immune response generated by vaccination with the heteroclitic peptide is greater than the immune response less than the response to vaccination with the original peptide. In another embodiment, a heteroclitic peptide of the present invention is an HLA class I heteroclitic peptide. Methods for identifying HLA class I and class II residues, and for improving HLA binding by mutating the residues, are well known in the art, as described below. Each possibility represents a separate embodiment of the present invention.

In another embodiment, a heteroclitic peptide of the present invention induces an immune response that is increased at least 2-fold relative to the WT1 peptide from which the heteroclitic peptide was derived ("native peptide"). In another embodiment, the increase is 3-fold relative to the native peptide. In another embodiment, the increase is 5-fold relative to the native peptide. In another embodiment, the increase is 7-fold relative to the native peptide. In another embodiment, the increase is 10-fold relative to the native peptide. In another embodiment, the increase is 15-fold relative to the native peptide. In another embodiment, the increase is 20-fold relative to the native peptide. In another embodiment, the increase is 30-fold relative to the native peptide. In another embodiment, the increase is 50-fold relative to the native peptide. In another embodiment, the increase is 100-fold relative to the native peptide. In another embodiment, the increase is 150-fold relative to the native peptide. In another embodiment, the increase is 200-fold relative to the native peptide. In another embodiment, the increase is 300-fold relative to the native peptide. In another embodiment, the increase is 500-fold relative to the native peptide. In another embodiment, the increase is 1000-fold relative to the native peptide. In another embodiment, the increase is more than 1000-fold relative to the native peptide. Each possibility represents a separate embodiment of the present invention.

In another embodiment, the present invention provides a HLA class II heteroclitic peptide derived from an isolated WT1 peptide of the present invention. In another embodiment, the process of deriving comprises introducing a mutation that enhances a binding of the peptide to an HLA class II molecule. In another embodiment, the process of deriving consists of introducing a mutation that enhances a binding of the peptide to an HLA class I molecule. In another embodiment, the mutation is in an HLA class II anchor residue. In another embodiment, a heteroclitic class II peptide of the present invention is identified and tested in a manner analogous to identification and testing of HLA class I heteroclitic peptides, as exemplified herein. Each possibility represents a separate embodiment of the present invention.

In another embodiment, the HLA class II binding site in a peptide of the present invention is created or improved by mutation of an HLA class II motif anchor residue. In another embodiment, the anchor residue that is modified is in the P1 position. In another embodiment, the anchor residue is at the P2 position. In another embodiment, the anchor residue is at the P6 position. In another embodiment, the anchor residue is at the P9 position. In another embodiment, the anchor residue is selected from the P1, P2, P6, and P9 positions. In another embodiment, the anchor residue is at the P3 position. In another embodiment, the anchor residue is at the P4 position. In another embodiment, the anchor residue is at the P5 position. In another embodiment, the anchor residue is at the P6 position. In another embodiment, the anchor residue is at the P8 position. In another embodiment, the anchor residue is at the P10 position. In another embodiment, the anchor residue is at the P11 position. In another embodiment, the anchor residue is at the P12 position. In another embodiment, the anchor residue is at the P13 position. In another embodiment, the anchor residue is at any other anchor residue of an HLA class II molecule that is known in the art. In another embodiment, residues other than P1, P2, P6, and P9 serve as secondary anchor residues; therefore, mutating them can improve HLA class II binding. Each possibility represents a separate embodiment of the present invention.

In another embodiment, a heteroclitic peptide is generated by introduction of a mutation that creates an anchor motif. "Anchor motifs" or "anchor residues" refers, in another embodiment, to 1 or a set of preferred residues at particular positions in an HLA-binding sequence. In another embodiment, the HLA-binding sequence is an HLA class II-binding sequence. In another embodiment, the HLA-binding sequence is an HLA class I-binding sequence. In another embodiment, the positions corresponding to the anchor motifs are those that play a significant role in binding the HLA molecule. In another embodiment, the anchor residue is a primary anchor motif. In another embodiment, the anchor residue is a secondary anchor motif. Each possibility represents a separate embodiment of the present invention.

Methods for predicting MHC class II epitopes are well known in the art. In another embodiment, the MHC class II epitope is predicted using TEPITOPE (Meister G E, Roberts C G et al, Vaccine 1995 13: 581-91). In another embodiment, the MHC class II epitope is predicted using EpiMatrix (De Groot A S, Jesdale B M et al, AIDS Res Hum Retroviruses 1997 13: 529-31). In another embodiment, the MHC class II epitope is predicted using the Predict Method (Yu K, Petrovsky N et al, Mol. Med. 2002 8: 137-48). In another embodiment, the MHC class II epitope is predicted using the SYFPEITHI epitope prediction algorithm (Examples). In another embodiment, the MHC class II epitope is predicted using Rankpep. In another embodiment, the MHC class II epitope is predicted using any other method known in the art. Each possibility represents a separate embodiment of the present invention.

In another embodiment, in the case of HLA class II-binding peptides (e.g. HLA-DR-binding peptides), the anchor residue that is modified is in the P1 position (e.g. a position corresponding to F263 of the CII(259-273) peptide, an unrelated peptide that was used to define some of the anchor residues of an HLA-DR allele). In another embodiment, the anchor residue is in the P2 position (e.g. a position corresponding to K264 of the CII(259-273) peptide). In another embodiment, the anchor residue is in the P6 position. In another embodiment, the anchor residue is in the P9 position. In other embodiments, the anchor residue is the P3, P4, P5, P6, P8, P10, P11, P12, or P13 position. In another embodiment, the anchor residue is any other anchor residue of an HLA class II molecule that is known in the art. In another embodiment, residues other than P1, P2, P6, and P9 serve as secondary anchor residues; therefore, mutating them can improve HLA class II binding. In another embodiment, any combination of the above residues is mutated. Each possibility represents a separate embodiment of the present invention.

In another embodiment, a WT1 peptide of the present invention binds to 2 distinct HLA class II molecules. In another embodiment, the peptide binds to three distinct HLA class II molecules. In another embodiment, the peptide binds to four distinct HLA class II molecules. In another embodiment, the peptide binds to five distinct HLA class II molecules. In another embodiment, the peptide binds to six distinct HLA class II molecules. In another embodiment, the peptide binds to more than six distinct HLA class II molecules.

In another embodiment, the HLA class II molecules that are bound by a WT1 peptide of the present invention are encoded by two or more distinct alleles at a given HLA class II locus. In another embodiment, the HLA class II molecules are encoded by 3 distinct alleles at a locus. In another embodiment, the HLA class II molecules are encoded by 4 distinct alleles at a locus. In another embodiment, the HLA class II molecules are encoded by 5 distinct alleles at a locus. In another embodiment, the HLA class II molecules are encoded by 6 distinct alleles at a locus. In another embodiment, the HLA class II molecules are encoded by more than six distinct alleles at a locus.

In another embodiment, the HLA class II molecules bound by the WT1 peptide are encoded by HLA class II genes at 2 distinct loci. In another embodiment, the HLA molecules bound are encoded by HLA class II genes at 2 or more distinct loci. In another embodiment, the HLA molecules bound are encoded by HLA class II genes at 3 distinct loci. In another embodiment, the HLA molecules bound are encoded by HLA class II genes at 3 or more distinct loci. In another embodiment, the HLA molecules bound are encoded by HLA class II genes at 4 distinct loci. In another embodiment, the HLA molecules bound are encoded by HLA class II genes at 4 or more distinct loci. In another embodiment, the HLA molecules bound are encoded by HLA class II genes at more than 4 distinct loci. In other embodiments, the loci are selected from HLA-DRB loci. In another embodiment, the HLA class II-binding peptide is an HLA-DRA binding peptide. In another embodiment, the peptide is an HLA-DQA1 binding peptide. In another embodiment, the peptide is an HLA-DQB1 binding peptide. In another embodiment, the peptide is an HLA-DPA1 binding peptide. In another embodiment, the peptide is an HLA-DPB1 binding peptide. In another embodiment, the peptide is an HLA-DMA binding peptide. In another embodiment, the peptide is an HLA-DMB binding peptide. In another embodiment, the peptide is an HLA-DOA binding peptide. In another embodiment, the peptide is an HLA-DOB binding peptide. In another embodiment, the peptide binds to any other HLA class II molecule known in the art. Each possibility represents a separate embodiment of the present invention.

In another embodiment, a WT1 peptide of the present invention binds to 2 distinct HLA-DRB molecules. In another, embodiment, the peptide binds to 3 distinct HLA-DRB molecules. In another embodiment, the peptide binds to 4 distinct HLA-DRB molecules. In another embodiment, the peptide binds to 5 distinct HLA-DRB molecules. In another embodiment, the peptide binds to 6 distinct HLA-DRB molecules. In another embodiment, the peptide binds to more than 6 distinct HLA-DRB molecules.

In another embodiment, a WT1 peptide of the present invention binds to HLA-DRB molecules that are encoded by 2 distinct HLA-DRB alleles. In another embodiment, the HLA-DRB molecules are encoded by 3 distinct HLA-DRB alleles. In another embodiment, the HLA-DRB molecules are encoded by 4 distinct HLA-DRB alleles. In another embodiment, the HLA-DRB molecules are encoded by 5 distinct HLA-DRB alleles. In another embodiment, the HLA-DRB molecules are encoded by 6 distinct HLA-DRB alleles. In another embodiment, the HLA-DRB molecules are encoded by more than 6 distinct HLA-DRB alleles. Each possibility represents a separate embodiment of the present invention.

In another embodiment, a WT1 peptide of the present invention binds to HLA-DRB molecules that are encoded by 2 distinct HLA-DRB alleles selected from DRB 101, DRB 301, DRB 401, DRB 701, DRB 1101, and DRB 1501. In another embodiment, the WT1 peptide binds to HLA-DRB molecules encoded by 3 distinct HLA-DRB alleles selected from DRB 101, DRB 301, DRB 401, DRB 701, DRB 1101, and DRB 1501. In another embodiment, the WT1 peptide binds to HLA-DRB molecules encoded by 4 distinct HLA-DRB alleles selected from DRB 101, DRB 301, DRB 401, DRB 701, DRB 1101, and DRB 1501. In another embodiment, the WT1 peptide binds to HLA-DRB molecules encoded by 5 distinct HLA-DRB alleles selected from DRB 101, DRB 301, DRB 401, DRB 701, DRB 1101, and DRB 1501. In another embodiment, the WT1 peptide binds to HLA-DRB molecules encoded by each of the following HLA-DRB alleles: DRB 101, DRB 301, DRB 401, DRB 701, DRB 1101, and DRB 1501. Each possibility represents a separate embodiment of the present invention.

In another embodiment, the present invention provides a composition comprising 2 distinct WT1 peptides of the present invention. In another embodiment, the 2 distinct WT1 peptides are both unaltered. In another embodiment, 1 of the WT1 peptides is unaltered, while the other is heteroclitic. In another embodiment, both of the WT1 peptides are heteroclitic.

In another embodiment, the composition comprises 3 distinct WT1 peptides of the present invention. In another embodiment, the composition comprises 4 distinct WT1 peptides of the present invention. In another embodiment, the composition comprises 5 distinct WT1 peptides of the present invention. In another embodiment, the composition comprises more than 5 distinct isolated WT1 peptides of the present invention.

In another embodiment, 2 of the WT1 peptides in the composition are unaltered. In another embodiment, 2 of the WT1 peptides in the composition are heteroclitic. In another embodiment, 2 of the WT1 peptides in the composition are unaltered, and 2 are heteroclitic. In another embodiment, more than 2 of the WT1 peptides in the composition are unaltered. In another embodiment, more than 2 of the WT1 peptides in the composition are heteroclitic. In another embodiment, more than 2 of the WT1 peptides in the composition are unaltered, and more than 2 are heteroclitic. Each possibility represents a separate embodiment of the present invention.

In another embodiment, 1 of the additional WT1 peptides in a composition of the present invention has a sequence selected from the sequences set forth in SEQ ID No: 1-3. In another embodiment, 2 of the additional WT1 peptides have a sequence selected from the sequences set forth in SEQ ID No: 1-3. In another embodiment, 3 of the additional WT1 peptides have a sequence selected from the sequences set forth in SEQ ID No: 1-3.

In another embodiment, any other immunogenic WT1 peptide known in the art is utilized as an additional WT1 peptide. In another embodiment, any combination of immunogenic WT1 peptides known in the art is utilized.

Each additional WT1 peptide, and each combination thereof, represents a separate embodiment of the present invention.

In another embodiment, a composition of the present invention contains 2 HLA class II heteroclitic peptides that are derived from the same isolated WT1 peptide of the present invention. In another embodiment, the 2 HLA class II heteroclitic peptides contain mutations in different HLA class II molecule anchor residues. In another embodiment, the 2 HLA class II heteroclitic peptides contain different mutations in the same anchor residues. In another embodiment, 2 of the HLA class II heteroclitic peptides are derived from different isolated WT1 peptides of the present invention. Each possibility represents a separate embodiment of the present invention.

In another embodiment, 2 WT1 peptides of the present invention, or the WT1 peptides that correspond to two HLA class II heteroclitic peptides of the present invention, overlap with one another. In another embodiment, the overlap between the peptides is at least 7 amino acids (AA). In another embodiment, the overlap is at least 8 AA. In another embodiment, the overlap is at least 9 AA. In another embodiment, the overlap is 7 AA. In another embodiment, the overlap is 8 AA. In another embodiment, the overlap is 9 AA. In another embodiment, the overlap is 10 AA. In another embodiment, the overlap is 11 AA. In another embodiment, the overlap is 12 AA. In another embodiment, the overlap is 13 AA. In another embodiment, the overlap is 14 AA. In another embodiment, the overlap is 15 AA. In another embodiment, the overlap is 16 AA. In another embodiment, the overlap is more than 16 AA. Each possibility represents a separate embodiment of the present invention.

In another embodiment, the peptides in a composition of the present invention bind to 2 distinct HLA class II molecules. In another embodiment, the peptides bind to 3 distinct HLA class II molecules. In another embodiment, the peptides bind to 4 distinct HLA class II molecules. In another embodiment, the peptides bind to 5 distinct HLA class II molecules. In another embodiment, the peptides bind to more than 5 distinct HLA class II molecules. In another embodiment, the peptides in the composition bind to the same HLA class II molecules.

In another embodiment, each of the WT1 peptides in a composition of the present invention binds to a set of HLA class II molecules. In another embodiment, each of the WT1 peptides binds to a distinct set of HLA class II molecules. In another embodiment, the WT1 peptides in the composition bind to the same set of HLA class II molecules. In another embodiment, 2 of the WT1 peptides bind to a distinct but overlapping set of HLA class II molecules. In another embodiment, 2 or more of the WT1 peptides bind to the same set of HLA class II molecules, while another of the WT1 peptides binds to a distinct set. In another embodiment, 2 or more of the WT1 peptides bind to an overlapping set of HLA class II molecules, while another of the WT1 peptides binds to a distinct set.

In another embodiment, 2 or more of the WT1 peptides in a composition of the present invention each binds to more than 1 HLA-DRB molecule. In another embodiment, the 4 or more HLA-DRB molecules bound by the peptides in the composition are distinct from one another. In another embodiment, the HLA-DRB molecules are encoded by different HLA-DRB alleles. Each possibility represents a separate embodiment of the present invention.

In another embodiment, 2 or more of the HLA class II molecules bound by WT1 peptides in a composition of the present invention are HLA-DRB molecules. In another embodiment, 3 or more of the HLA class II molecules that are bound are HLA-DRB molecules. In other embodiments, the HLA class II molecules that are bound can be any of the HLA class II molecules enumerated herein. In another embodiment, the HLA class II molecules that are bound are encoded by 2 or more distinct HLA class II alleles at a given locus. In another embodiment, the HLA class II molecules that are bound are encoded by HLA class II genes at 2 or more distinct loci.

Each of the above compositions represents a separate embodiment of the present invention.

In another embodiment, a "set of HLA class II molecules" refers to the HLA class II molecules encoded by different alleles at a particular locus. In another embodiment, the term refers to HLA class II molecules with a particular binding specificity. In another embodiment, the term refers to HLA class II molecules with a particular peptide consensus sequence. In another embodiment, the term refers to a superfamily of HLA class II molecules. Each possibility represents a separate embodiment of the present invention.

In another embodiment, the present invention provides a composition comprising an unaltered HLA class II molecule-binding WT1 peptide of the present invention and a second, HLA class I molecule-binding WT1 peptide. In another embodiment, the composition comprises more than 1 HLA class II molecule-binding WT1 peptide of the present invention, in addition to the HLA class I molecule-binding WT1 peptide. In another embodiment, the composition comprises more than 1 HLA class I molecule-binding WT1 peptide, in addition to the HLA class II molecule-binding WT1 peptide. Each possibility represents a separate embodiment of the present invention.

In another embodiment, the AA sequence of the HLA class I molecule-binding WT1 peptide comprises a sequence selected from SEQ ID No: 5-38. In another embodiment, the AA sequence of the HLA class I molecule-binding WT1 peptide is selected from the sequences set forth in SEQ ID No: 5-38. Each possibility represents a separate embodiment of the present invention.

In other embodiments, the HLA class I molecule bound by the HLA class I molecule-binding WT1 peptide is encoded by any of the HLA-A genes. In other embodiments, the HLA class I molecule is encoded by any of the HLA-B genes. In other embodiments, the HLA class I molecule is encoded by any of the HLA-C genes. In another embodiment, the HLA class I molecule is an HLA-0201 molecule. In another embodiment, the molecule is HLA A1. In other embodiments, the molecule is HLA A3.2, HLA A11, HLA A24, HLA B7, HLA B8, HLA B27, or HLA A2, A3, A4, A5, or B8. HLA A1, HLA A2.1, or HLA A3.2. In other embodiment, the HLA class II molecule is encoded by any of the HLA genes HLA-DP, -DQ, or -DR. Each possibility represents a separate embodiment of the present invention.

In another embodiment, the HLA class I molecule-binding WT1 peptide of methods and compositions of the present invention binds to a superfamily of HLA class I molecules. In another embodiment, the superfamily is the A2 superfamily. In another embodiment, the superfamily is the A3 superfamily. In another embodiment, the superfamily is the A24 superfamily. In another embodiment, the superfamily is the B7 superfamily. In another embodiment, the superfamily is the B27 superfamily. In another embodiment, the superfamily is the B44 superfamily. In another embodiment, the superfamily is the C1 superfamily. In another embodiment, the superfamily is the C4 superfamily. In another embodiment, the superfamily is any other superfamily known in the art. Each possibility represents a separate embodiment of the present invention. In another embodiment, the HLA molecule is HLA A0201.

In another embodiment, the HLA class I molecule-binding WT1 peptide is an HLA class I heteroclitic peptide. In another embodiment, the HLA class I molecule-binding WT1 peptide contains a mutation in an HLA class I molecule anchor residue thereof, as described further herein. As provided herein, WT1-derived peptides were modified in HLA anchor residues to generate heteroclitic peptides with increased predicted binding to HLA-A0201 and HLA-A0301. Peptides with increased predicted binding also exhibited enhanced ability to bind HLA class I molecules and increased immunogenicity.

In another embodiment, the mutation that enhances MHC binding is in the residue at position 1 of the HLA class I heteroclitic peptide. In another embodiment, the residue is changed to tyrosine. In another embodiment, the residue is changed to glycine. In another embodiment, the residue is changed to threonine. In another embodiment, the residue is changed to phenylalanine. In another embodiment, the residue is changed to any other residue known in the art. In another embodiment, a substitution in position 1 (e.g. to tyrosine) stabilizes the binding of the position 2 anchor residue.

In another embodiment, the mutation is in position 2 of the HLA class I heteroclitic peptide. In another embodiment, the residue is changed to leucine. In another embodiment, the residue is changed to valine. In another embodiment, the residue is changed to isoleucine. In another embodiment, the residue is changed to methionine. In another embodiment, the residue is changed to any other residue known in the art.

In another embodiment, the mutation is in position 6 of the HLA class I heteroclitic peptide. In another embodiment, the residue is changed to valine. In another embodiment, the residue is changed to cysteine. In another embodiment, the residue is changed to glutamine. In another embodiment, the residue is changed to histidine. In another embodiment, the residue is changed to any other residue known in the art.

In another embodiment, the mutation is in position 9 of the HLA class I heteroclitic peptide. In another embodiment, the mutation changes the residue at the C-terminal position thereof. In another embodiment, the residue is changed to valine. In another embodiment, the residue is changed to threonine. In another embodiment, the residue is changed to isoleucine. In another embodiment, the residue is changed to leucine. In another embodiment, the residue is changed to alanine. In another embodiment, the residue is changed to cysteine. In another embodiment, the residue is changed to any other residue known in the art.

In another embodiment, the point mutation is in a primary anchor residue. In another embodiment, the HLA class I primary anchor residues are positions 2 and 9. In another embodiment, the point mutation is in a secondary anchor residue. In another embodiment, the HLA class I secondary anchor residues are positions 1 and 8. In another embodiment, the HLA class I secondary anchor residues are positions 1, 3, 6, 7, and 8. In another embodiment, the point mutation is in a position selected from positions 4, 5, and 8. Each possibility represents a separate embodiment of the present invention.

In another embodiment, the point mutation is in 1 or more residues in positions selected from positions 1, 2, 8, and 9 of the HLA class I binding motif. In another embodiment, the point mutation is in 1 or more residues in positions selected from positions 1, 3, 6, and 9. In another embodiment, the point mutation is in 1 or more residues in positions selected from positions 1, 2, 6, and 9. In another embodiment, the point mutation is in 1 or more residues in positions selected from positions 1, 6, and 9. In another embodiment, the point mutation is in 1 or more residues in positions selected from positions 1, 2, and 9. In another embodiment, the point mutation is in 1 or more residues in positions selected from positions 1, 3, and 9. In another embodiment, the point mutation is in 1 or more residues in positions selected from positions 2 and 9. In another embodiment, the point mutation is in 1 or more residues in positions selected from positions 6 and 9. Each possibility represents a separate embodiment of the present invention.

Each of the above anchor residues and substitutions represents a separate embodiment of the present invention.

In another embodiment, the HLA class I molecule-binding WT1 peptide comprises a sequence selected from SEQ ID No: 6, 8, 10, 12, 14, 16, 18, 20, 22, 24-26, 28-30, 32-34, and 36-38. In another embodiment, the HLA class I molecule-binding WT1 peptide has a sequence selected from the sequences set forth in SEQ ID No: 6, 8, 10, 12, 14, 16, 18, 20, 22, 24-26, 28-30, 32-34, and 36-38.

In another embodiment, the HLA class I molecule-binding WT peptide has a length of 9-13 AA. In another embodiment, the length is 8-13 AA. In another embodiment, the peptide has any of the lengths of a peptide of the present invention enumerated herein.

In another embodiment, the HLA class I molecule-binding WT peptide has length of 9 AA. In another embodiment, the peptide has length of 10 AA. As provided herein, native and heteroclitic peptides of 9-10 AA exhibited substantial binding to HLA class I molecules and ability to elicit cytokine secretion and cytolysis by CTL.

In another embodiment, the HLA class I molecule that is bound by the HLA class I molecule-binding WT1 peptide is an HLA-A molecule. In another embodiment, the HLA class I-molecule is an HLA-A2 molecule. In another embodiment, the HLA class I-molecule is an HLA-A3 molecule. In another embodiment, the HLA class I-molecule is an HLA-A11 molecule. In another embodiment, the HLA class I-molecule is an HLA-B8 molecule. In another embodiment, the HLA class I-molecule is an HLA-0201 molecule. In another embodiment, the HLA class I-molecule binds any other HLA class I molecule known in the art. Each possibility represents a separate embodiment of the present invention.

In another embodiment, a WT1 peptide of methods and compositions of the present invention has a length of 8-30 amino acids. In another embodiment, the peptide has a length of 9-11 AA. In another embodiment, the peptide ranges in size from 7-25 AA, or in another embodiment, 8-11, or in another embodiment, 8-15, or in another embodiment, 9-20, or in another embodiment, 9-18, or in another embodiment, 9-15, or in another embodiment, 8-12, or in another embodiment, 9-11 AA in length. In another embodiment, the peptide is 8 AA in length, or in another embodiment, 9 AA or in another embodiment, 10 AA or in another embodiment, 12 AA or in another embodiment, 25 AA in length, or in another embodiment, any length therebetween. In another embodiment, the peptide is of greater length, for example 50, or 100, or more. In this embodiment, the cell processes the peptide to a length of 7 and 25 AA in length. In this embodiment, the cell processes the peptide to a length of 9-11 AA Each possibility represents a separate embodiment of the present invention.

In another embodiment, the peptide is 15-23 AA in length. In another embodiment, the length is 15-24 AA. In another embodiment, the length is 15-25 AA. In another embodiment, the length is 15-26 AA. In another embodiment, the length is 15-27 AA. In another embodiment, the length is 15-28 AA. In another embodiment, the length is 14-30 AA. In another embodiment, the length is 14-29 AA. In another embodiment, the length is 14-28 AA. In another embodiment, the length is 14-26 AA. In another embodiment, the length is 14-24 AA. In another embodiment, the length is 14-22 AA. In another embodiment, the length is 14-20 AA. In another embodiment, the length is 16-30 AA. In another embodiment, the length is 16-28 AA. In another embodiment, the length is 16-26 AA. In another embodiment, the length is 16-24 AA. In another embodiment, the length is 16-22 AA. In another embodiment, the length is 18-30 AA. In another embodiment, the length is 18-28 AA. In another embodiment, the length is 18-26 AA. In another embodiment, the length is 18-24 AA. In another embodiment, the length is 18-22 AA. In another embodiment, the length is 18-20 AA. In another embodiment, the length is 20-30 AA. In another embodiment, the length is 20-28 AA. In another embodiment, the length is 20-26 AA. In another embodiment, the length is 20-24 AA. In another embodiment, the length is 22-30 AA. In another embodiment, the length is 22-28 AA. In another embodiment, the length is 22-26 AA. In another embodiment, the length is 24-30 AA. In another embodiment, the length is 24-28 AA. In another embodiment, the length is 24-26 AA.

Each of the above peptides, peptide lengths, and types of peptides represents a separate embodiment of the present invention.

In another embodiment, minor modifications are made to peptides of the present invention without decreasing their affinity for HLA molecules or changing their TCR specificity, utilizing principles well known in the art. In the case of HLA class I-binding peptides, "minor modifications" refers, in another embodiment, to e.g. insertion, deletion, or substitution of one AA, inclusive, or deletion or addition of 1-3 AA outside of the residues between 2 and 9, inclusive. While the computer algorithms described herein are useful for predicting the MHC class I-binding potential of peptides, they have 60-80% predictive accuracy; and thus, the peptides should be evaluated empirically before a final determination of MHC class I-binding affinity is made. Thus, peptides of the present invention are not limited to peptides predicated by the algorithms to exhibit strong MHC class I-binding affinity. The types are modifications that can be made are listed below. Each modification represents a separate embodiment of the present invention.

In another embodiment, a peptide enumerated in the Examples of the present invention is further modified by mutating an anchor residue to an MHC class I preferred anchor residue, which can be, in other embodiments, any of the anchor residues enumerated herein. In another embodiment, a peptide of the present invention containing an MHC class I preferred anchor residue is further modified by mutating the anchor residue to a different MHC class I preferred residue for that location. The different preferred residue can be, in other embodiments, any of the preferred residues enumerated herein.

In another embodiment, the anchor residue that is further modified is in the 1 position. In another embodiment, the anchor residue is in the 2 position. In another embodiment, the anchor residue is in the 3 position. In another embodiment, the anchor residue is in the 4 position. In another embodiment, the anchor residue is in the 5 position. In another embodiment, the anchor residue is in the 6 position. In another embodiment, the anchor residue is in the 7 position. In another embodiment, the anchor residue is in the 8 position. In another embodiment, the anchor residue is in the 9 position. In the case of HLA class I-binding peptides, residues other than 2 and 9 can serve as secondary anchor residues; therefore, mutating them can improve MHC class I binding. Each possibility represents a separate embodiment of the present invention.

In another embodiment, a peptide of methods and compositions of the present invention is a length variant of a peptide enumerated in the Examples. In another embodiment, the length variant is one amino acid (AA) shorter than the peptide from the Examples. In another embodiment, the length variant is two AA shorter than the peptide from the Examples. In another embodiment, the length variant is more than two AA shorter than the peptide from the Examples. In another embodiment, the shorter peptide is truncated on the N-terminal end. In another embodiment, the shorter peptide is truncated on the C-terminal end. In another embodiment, the truncated peptide is truncated on both the N-terminal and C-terminal ends. Peptides are, in another embodiment, amenable to truncation without changing affinity for HLA molecules, as is well known in the art.

Each of the above truncated peptides represents a separate embodiment of the present invention.

In another embodiment, the length variant is longer than a peptide enumerated in the Examples of the present invention. In another embodiment, the longer peptide is extended on the N-terminal end in accordance with the surrounding WT1 sequence. Peptides are, in another embodiment, amenable to extension on the N-terminal end without changing affinity for HLA molecules, as is well known in the art. Such peptides are thus equivalents of the peptides enumerated in the Examples. In another embodiment, the N-terminal extended peptide is extended by one residue. In another embodiment, the N-terminal extended peptide is extended by two residues. In another embodiment, the N-terminal extended peptide is extended by three residues. In another embodiment, the N-terminal extended peptide is extended by more than three residues.

In another embodiment, the longer peptide is extended on the C terminal end in accordance with the surrounding WT1 sequence. Peptides are, in another embodiment, amenable to extension on the C-terminal end without changing affinity for HLA molecules, as is well known in the art. Such peptides are thus equivalents of the peptides enumerated in the Examples of the present invention. In another embodiment, the C-terminal extended peptide is extended by one residue. In another embodiment, the C-terminal extended peptide is extended by two residues. In another embodiment, the C-terminal extended peptide is extended by three residues. In another embodiment, the C-terminal extended peptide is extended by more than three residues.

In another embodiment, the extended peptide is extended on both the N-terminal and C-terminal ends in accordance with the surrounding WT1 sequence.

Each of the above extended peptides represents a separate embodiment of the present invention.

In another embodiment, a truncated peptide of the present invention retains the HLA anchor residues (e.g. the HLA class I anchor residues) on the second residue and the C-terminal residue, with a smaller number of intervening residues (e.g. 5) than a peptide enumerated in the Examples of the present invention. Peptides are, in another embodiment, amenable to such mutation without changing affinity for HLA molecules. In another embodiment, such a truncated peptide is designed by removing one of the intervening residues of one of the above sequences. In another embodiment, the HLA anchor residues are retained on the second and eighth residues. In another embodiment, the HLA anchor residues are retained on the first and eighth residues. Each possibility represents a separate embodiment of the present invention.

In another embodiment, an extended peptide of the present invention retains the HLA anchor residues (e.g. the HLA class I anchor residues) on the second residue and the C-terminal residue, with a larger number of intervening residues (e.g. 7 or 8) than a peptide enumerated in the Examples of the present invention. In another embodiment, such an extended peptide is designed by adding one or more residues between two of the intervening residues of one of the above sequences. It is well known in the art that residues can be removed from or added between the intervening sequences of HLA-binding peptides without changing affinity for HLA. Such peptides are thus equivalents of the peptides enumerated in the Examples of the present invention. In another embodiment, the HLA anchor residues are retained on the second and ninth residues. In another embodiment, the HLA anchor residues are retained on the first and eighth residues. In another embodiment, the HLA anchor residues are retained on the two residues separated by six intervening residues. Each possibility represents a separate embodiment of the present invention.

"Fragment," in another embodiment, refers to a peptide of 11 or more AA in length. In another embodiment, a peptide fragment of the present invention is 16 or more AA long. In another embodiment, the fragment is 12 or more AA long. In another embodiment, the fragment is 13 or more AA. In another embodiment, the fragment is 14 or more AA. In another embodiment, the fragment is 15 or more AA. In another embodiment, the fragment is 17 or more AA. In another embodiment, the fragment is 18 or more AA. In another embodiment, the fragment is 19 or more AA. In another embodiment, the fragment is 22 or more AA. In another embodiment, the fragment is 8-12 AA. In another embodiment, the fragment is about 8-12 AA. In another embodiment, the fragment is 16-19 AA. In another embodiment, the fragment is about 16-19 AA. In another embodiment, the fragment 10-25 AA. In another embodiment, the fragment is about 10-25 AA. In another embodiment, the fragment has any other length. Each possibility represents a separate embodiment of the present invention.

"Fragment of a WT1 protein," in another embodiment, refers to any of the definitions of "fragment" found herein. Each definition represents a separate embodiment of the present invention.

As provided herein, mesothelioma cells express WT1 protein (Example 7). In addition, mesothelioma cells process and present peptides of the present invention or the corresponding native peptides (Example 5). Moreover, the presentation is robust enough to elicit anti-WT1 specific immune responses (Example 5). Thus, mesothelioma cells can be targeted by anti-WT1 immune therapy.

In another embodiment, a peptide of the present invention is homologous to a peptide enumerated in the Examples. The terms "homology," "homologous," etc, when in reference to any protein or peptide, refer, in another embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

In another embodiment, the term "homology," when in reference to any nucleic acid sequence similarly indicates a percentage of nucleotides in a candidate sequence that are identical with the nucleotides of a corresponding native nucleic acid sequence.

Homology is, in another embodiment, determined by computer algorithm for sequence alignment, by methods well described in the art. In other embodiments, computer algorithm analysis of nucleic acid sequence homology includes the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence selected from SEQ ID No: 1-38 of greater than 70%. In another embodiment, "homology" refers to identity to a sequence selected from SEQ ID No: 1-38 of greater than 72%. In another embodiment, "homology" refers to identity to one of SEQ ID No: 1-38 of greater than 75%. In another embodiment, "homology" refers to identity to a sequence selected from SEQ ID No: 1-38 of greater than 78%. In another embodiment, "homology" refers to identity to one of SEQ ID No: 1-38 of greater than 80%. In another embodiment, "homology" refers to identity to one of SEQ ID No: 1-38 of greater than 82%. In another embodiment, "homology" refers to identity to a sequence selected from SEQ ID No: 1-38 of greater than 83%. In another embodiment, "homology" refers to identity to one of SEQ ID No: 1-38 of greater than 85%. In another embodiment, "homology" refers to identity to one of SEQ ID No: 1-38 of greater than 87%. In another embodiment, "homology" refers to identity to a sequence selected from SEQ ID No: 1-38 of greater than 88%. In another embodiment, "homology" refers to identity to one of SEQ ID No: 1-38 of greater than 90%. In another embodiment, "homology" refers to identity to one of SEQ ID No: 1-38 of greater than 92%. In another embodiment, "homology" refers to identity to a sequence selected from SEQ ID No: 1-38 of greater than 93%. In another embodiment, "homology" refers to identity to one of SEQ ID No: 1-38 of greater than 95%. In another embodiment, "homology" refers to identity to a sequence selected from SEQ ID No: 1-38 of greater than 96%. In another embodiment, "homology" refers to identity to one of SEQ ID No: 1-38 of greater than 97%. In another embodiment, "homology" refers to identity to one of SEQ ID No: 1-38 of greater than 98%. In another embodiment, "homology" refers to identity to one of SEQ ID No: 1-38 of greater than 99%. In another embodiment, "homology" refers to identity to one of SEQ ID No: 1-38 of 100%. Each possibility represents a separate embodiment of the present invention.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y). In another embodiments, methods of hybridization are carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA.

Each of the above homologues and variants of peptides enumerated in the Examples represents a separate embodiment of the present invention.

In another embodiment, the present invention provides a composition comprising a peptide of this invention. In another embodiment, the composition further comprises a pharmaceutically acceptable carrier. In another embodiment, the composition further comprises an adjuvant. In another embodiment, the composition comprises 2 or more peptides of the present invention. In another embodiment, the composition further comprises any of the additives, compounds, or excipients set forth hereinbelow. In another embodiment, the adjuvant is KLH, QS21, Freund's complete or incomplete adjuvant, aluminum phosphate, aluminum hydroxide, BCG or alum. In other embodiments, the carrier is any carrier enumerated herein. In other embodiments, the adjuvant is any adjuvant enumerated herein. Each possibility represents a separate embodiment of the present invention.

In another embodiment, this invention provides a vaccine comprising a peptide of this invention. In another embodiment, this invention provides a vaccine comprising an antigen-presenting cell (APC) and a peptide of this invention. In another embodiment, the vaccine further comprises a carrier. In another embodiment, the vaccine further comprises an adjuvant. In another embodiment, the vaccine further comprises an APC. In another embodiment, the vaccine further comprises a combination of more than 1 of an antigen, carrier, and/or APC. In another embodiment, the vaccine is a cell-based composition. Each possibility represents a separate embodiment of the present invention.

In another embodiment, the term "vaccine" refers to a material or composition that, when introduced into a subject, provides a prophylactic or therapeutic response for a particular disease, condition, or symptom of same. In another embodiment, this invention comprises peptide-based vaccines, wherein the peptide comprises any embodiment listed herein, including immunomodulating compounds such as cytokines, adjuvants, etc.

In another embodiment, a vaccine of methods and compositions of the present invention further comprises an adjuvant. In another embodiment, the adjuvant is Montanide ISA 51. Montanide ISA 51 contains a natural metabolizable oil and a refined emulsifier. In another embodiment, the adjuvant is GM-CSF. Recombinant GM-CSF is a human protein grown, in another embodiment, in a yeast (*S. cerevisiae*) vector. GM-CSF promotes clonal expansion and differentiation of hematopoietic progenitor cells, APC, and dendritic cells and T cells.

In another embodiment, the adjuvant is a cytokine. In another embodiment, the adjuvant is a growth factor. In another embodiment, the adjuvant is a cell population. In another embodiment, the adjuvant is QS21. In another embodiment, the adjuvant is Freund's incomplete adjuvant. In another embodiment, the adjuvant is aluminum phosphate. In another embodiment, the adjuvant is aluminum hydroxide. In another embodiment, the adjuvant is BCG. In another embodiment, the adjuvant is alum. In another embodiment, the adjuvant is an interleukin. In another embodiment, the adjuvant is a chemokine. In another embodiment, the adjuvant is any other type of adjuvant known in the art. In another embodiment, the WT1 vaccine comprises two the above adjuvants. In another embodiment, the WT1 vaccine comprises more than two the above adjuvants. Each possibility represents a separate embodiment of the present invention.

In other embodiments, a vaccine or composition of the present invention can comprise any of the embodiments of WT1 peptides of the present invention and combinations thereof. Each possibility represents a separate embodiment of the present invention.

It is to be understood that any embodiments described herein, regarding peptides, vaccines and compositions of this invention can be employed in any of the methods of this invention. Each combination of peptide, vaccine, or composition with a method represents an embodiment thereof.

In another embodiment, the present invention provides a method of treating a subject with a WT1-expressing cancer, the method comprising administering to the subject a WT1 vaccine of the present invention, thereby treating a subject with a WT1-expressing cancer.

In another embodiment, the present invention provides a method of treating a subject with an MDS, the method comprising administering to the subject a WT1 vaccine of the present invention, thereby treating a subject with an MDS.

In another embodiment, the present invention provides a method of suppressing or halting the progression of a WT1-expressing cancer in a subject, the method comprising administering to the subject a WT1 vaccine of the present invention, thereby suppressing or halting the progression of a WT1-expressing cancer.

In another embodiment, the present invention provides a method of reducing the incidence of a WT1-expressing cancer in a subject, the method comprising administering to the subject a WT1 vaccine of the present invention, thereby reducing the incidence of a WT1-expressing cancer in a subject.

In another embodiment, the present invention provides a method of reducing the incidence of an AML in a subject, the method comprising administering to the subject a WT1 vaccine of the present invention, thereby reducing the incidence of an AML.

In another embodiment, the present invention provides a method of reducing the incidence of relapse of a WT1-expressing cancer in a subject, the method comprising administering to the subject a WT1 vaccine of the present invention, thereby reducing the incidence of relapse of a WT1-expressing cancer in a subject.

In another embodiment, the present invention provides a method of reducing the incidence of relapse of an AML in a subject, the method comprising administering to the subject a WT1 vaccine of the present invention, thereby reducing the incidence of relapse of an AML in a subject.

In another embodiment, the present invention provides a method of breaking a T cell tolerance of a subject to a WT1-expressing cancer, the method comprising administering to the subject a WT1 vaccine of the present invention, thereby breaking a T cell tolerance to a WT1-expressing cancer.

In another embodiment, the present invention provides a method of treating a subject having a WT1-expressing cancer, comprising (a) inducing in a donor formation and proliferation of human cytotoxic T lymphocytes (CTL) that recognize a malignant cell of the cancer by a method of the present invention; and (b) infusing the human CTL into the subject, thereby treating a subject having a cancer.

In another embodiment, the present invention provides a method of treating a subject having a WT1-expressing cancer, comprising (a) inducing ex vivo formation and proliferation of human CTL that recognize a malignant cell of the cancer by a method of the present invention, wherein the human immune cells are obtained from a donor; and (b) infusing the human CTL into the subject, thereby treating a subject having a cancer.

Methods for ex vivo immunotherapy are well known in the art and are described, for example, in United States Patent Application Serial Numbers 2006/0057130, 2005/0221481, 2005/0214268, 2003/0175272, 2002/0127718, and U.S. Pat. No. 5,229,115, which are incorporated herein by reference. Additional methods are well known in the art and are described, for example, in Davis I D et al (Blood dendritic cells generated with Flt3 ligand and CD40 ligand prime CD8+ T cells efficiently in cancer patients. J. Immunother. 2006 September-October; 29(5):499-511) and Mitchell M S et al (The cytotoxic T cell response to peptide analogs of the HLA-A*0201-restricted MUC1 signal sequence epitope, M1.2. Cancer Immunol Immunother. 2006 Jul. 28). Each method represents a separate embodiment of the present invention.

In another embodiment, the present invention provides a method of inducing the formation and proliferation of CTL specific for cells of a WT1-expressing cancer, the method comprising contacting a lymphocyte population with a vaccine of the present invention. In another embodiment, the vaccine is an APC associated with a peptide of the present invention. In another embodiment, the vaccine is an APC associated with a mixture of peptides of the present invention. Each possibility represents a separate embodiment of the present invention.

In another embodiment, this invention provides a method of generating a heteroclitic immune response in a subject, wherein the heteroclitic immune response is directed against a WT1-expressing cancer, the method comprising administering to the subject a vaccine of the present invention, thereby generating a heteroclitic immune response.

In another embodiment, the present invention provides a method of inducing an anti-mesothelioma immune response in a subject, the method comprising the step of contacting the subject with an immunogenic composition comprising (a) a WT1 protein; or (b) a fragment of a WT protein, thereby inducing an anti-mesothelioma immune response in a subject. In another embodiment, the mesothelioma is a malignant mesothelioma. Each possibility represents a separate embodiment of the present invention.

In another embodiment, the present invention provides a method of inducing an anti-mesothelioma immune response in a subject, the method comprising the step of contacting the subject with an immunogenic composition comprising a nucleotide molecule encoding (a) a WT1 protein; or (b) a fragment of a WT1 protein, thereby inducing an anti-mesothelioma immune response in a subject. In another embodiment, the mesothelioma is a malignant mesothelioma. Each possibility represents a separate embodiment of the present invention.

In another embodiment, the present invention provides a method of treating a subject with a mesothelioma, the method comprising the step of administering to the subject an immunogenic composition comprising (a) a WT1 protein; or (b) a fragment of a WT protein, thereby treating a subject with a mesothelioma. In another embodiment, the mesothelioma is a malignant mesothelioma. Each possibility represents a separate embodiment of the present invention.

In another embodiment, the present invention provides a method of treating a subject with a mesothelioma, the method comprising the step of administering to the subject an immunogenic composition comprising a nucleotide molecule encoding (a) a WT1 protein; or (b) a fragment of a WT1 protein, thereby treating a subject with a mesothelioma. In another embodiment, the mesothelioma is a malignant mesothelioma. Each possibility represents a separate embodiment of the present invention.

In another embodiment, the present invention provides a method of reducing an incidence of a mesothelioma, or its relapse, in a subject, the method comprising the step of administering to the subject an immunogenic composition comprising (a) a WT1 protein; or (b) a fragment of a WT protein, thereby reducing an incidence of a mesothelioma, or its relapse, in a subject. In another embodiment, the mesothelioma is a malignant mesothelioma. Each possibility represents a separate embodiment of the present invention.

In another embodiment, the present invention provides a method of reducing an incidence of a mesothelioma, or its relapse, in a subject, the method comprising the step of administering to the subject an immunogenic composition comprising a nucleotide molecule encoding (a) a WT1 protein; or (b) a fragment of a WT1 protein, thereby reducing an incidence of a mesothelioma, or its relapse, in a subject. In another embodiment, the mesothelioma is a malignant mesothelioma. Each possibility represents a separate embodiment of the present invention.

In another embodiment, a target cell of an immune response elicited by a method of the present invention presents the WT1 peptide of the present invention, or a corresponding WT1 fragment, on an HLA molecule. In another embodiment, the HLA molecule is an HLA class I molecule. In other embodiments, the HLA molecule is any HLA class I subtype or HLA class I molecule known in the art. In another embodiment, the immune response against the WT1 peptide or fragment is a heteroclitic immune response. Each possibility represents a separate embodiment of the present invention.

In another embodiment, the WT1-expressing cancer is an acute myelogenous leukemia (AML). In another embodiment, the WT1-expressing cancer is associated with a myelodysplastic syndrome (MDS). In another embodiment, the WT1-expressing cancer is an MDS. In another embodiment, the WT1-expressing cancer is a non-small cell lung cancer (NSCLC). In another embodiment, the WT1-expressing cancer is a Wilms' tumor. In another embodiment, the WT1-expressing cancer is a leukemia. In another embodiment, the WT1-expressing cancer is a hematological cancer. In another embodiment, the WT1-expressing cancer is a lymphoma. In another embodiment, the WT1-expressing cancer is a desmoplastic small round cell tumor. In another embodiment, the WT1-expressing cancer is a mesothelioma. In another embodiment, the WT1-expressing cancer is a malignant mesothelioma. In another embodiment, the WT1-expressing cancer is a gastric cancer. In another embodiment, the WT1-expressing cancer is a colon cancer. In another embodiment, the WT1-expressing cancer is a lung cancer. In another embodiment, the WT1-expressing cancer is a breast cancer. In another embodiment, the WT1-expressing cancer is a germ cell tumor. In another embodiment, the WT1-expressing cancer is an ovarian cancer. In another embodiment, the WT1-expressing cancer is a uterine cancer. In another embodiment, the WT1-expressing cancer is a thyroid cancer. In another embodiment, the WT1-expressing cancer is a hepatocellular carcinoma. In another embodiment, the WT1-expressing cancer is a thyroid cancer. In another embodiment, the WT1-expressing cancer is a liver cancer. In another embodiment, the WT1-expressing cancer is a renal cancer. In another embodiment, the WT1-expressing cancer is a kaposi's sarcoma. In another embodiment, the WT1-expressing cancer is a sarcoma. In another embodiment, the WT1-expressing cancer is any other carcinoma or sarcoma.

In another embodiment, the WT1-expressing cancer is a solid tumor. In another embodiment, the solid tumor is associated with a WT1-expressing cancer. In another embodiment, the solid tumor is associated with a myelodysplastic syndrome (MDS). In another embodiment, the solid tumor is associated with a non-small cell lung cancer (NSCLC). In another embodiment, the solid tumor is associated with a lung cancer. In another embodiment, the solid tumor is associated with a breast cancer. In another embodiment, the solid tumor is associated with a colorectal cancer. In another embodiment, the solid tumor is associated with a prostate cancer. In another embodiment, the solid tumor is associated with an ovarian cancer. In another embodiment, the solid tumor is associated with a renal cancer. In another embodiment, the solid tumor is associated with a pancreatic cancer. In another embodiment, the solid tumor is associated with a brain cancer. In another embodiment, the solid tumor is associated with a gastrointestinal cancer. In another embodiment, the solid tumor is associated with a skin cancer. In another embodiment, the solid tumor is associated with a melanoma.

In another embodiment, a cancer or tumor treated by a method of the present invention is suspected to express WT1. In another embodiment, WT1 expression has not been verified by testing of the actual tumor sample. In another embodiment, the cancer or tumor is of a type known to express WT1 in many cases. In another embodiment, the type expresses WT1 in the majority of cases.

Each type of WT1-expressing cancer or tumor, and cancer or tumor suspected to express WT1, represents a separate embodiment of the present invention.

Any embodiments enumerated herein, regarding peptides, vaccines and compositions of this invention can be employed in any of the methods of this invention, and each represents an embodiment thereof.

In another embodiment, multiple peptides of this invention are used to stimulate an immune response in methods of the present invention.

As provided herein, peptides of the present invention elicit antigen-specific $CD8^+$ T cell responses (Examples 1-2) and $CD4^+$ T cell responses (Examples 3-4). $CD4^+$ T cells recognize peptides bound to the HLA class II molecule on APC. In another embodiment, antigen-specific $CD4^+$ T cell responses assist in induction and maintenance of $CD8^+$ cytotoxic T cell (CTL) responses. In another embodiment, activated $CD4^+$ cells enhance immunity by licensing dendritic cells, thereby sustaining the activation and survival of the cytotoxic T cells. In another embodiment, activated $CD4^+$ T cells induce tumor cell death by direct contact with the tumor cell or by activation of the apoptosis pathway. Mesothelioma tumor cells, for example, are able to process and present antigens in the context of HLA class I and class II molecules.

In another embodiment, vaccines of the present invention have the advantage of activating or eliciting both $CD4^+$ and $CD8^+$ T cells that recognize WT1 antigens. In another embodiment, activation or eliciting both $CD4^+$ and $CD8^+$ T cells provides a synergistic anti-WT1 immune response, relative to activation of either population alone.

The methods disclosed herein will be understood by those in the art to enable design of other WT1-derived peptides. The methods further enable design of peptides binding to other HLA molecules. The methods further enable design of vaccines combining WT1-derived peptides of the present invention. Each possibility represents a separate embodiment of the present invention.

In another embodiment, vaccines of the present invention have the advantage of activating or eliciting WT1-specific $CD4^+$ T cells containing a variety of different HLA class II alleles. In another embodiment, the vaccines have the advantage of activating or eliciting WT1-specific $CD4^+$ T cells in a substantial proportion of the population (e.g. in different embodiments, 50%, 55%, 60%, 65%, 70%, 75%, 80%. 85%, 90%, 95%, or greater than 95%). In another embodiment, the vaccines activate or elicit WT1-specific $CD4^+$ T cells in a substantial proportion of a particular population (e.g. American Caucasians). Each possibility represents a separate embodiment of the present invention.

In another embodiment, methods of the present invention provide for an improvement in an immune response that has already been mounted by a subject. In another embodiment, methods of the present invention comprise administering the peptide, composition, or vaccine 2 or more times. In another embodiment, the peptides are varied in their composition, concentration, or a combination thereof. In another embodiment, the peptides provide for the initiation of an immune response against an antigen of interest in a subject who has not yet initiated an immune response against the antigen. In another embodiment, the CTL that are induced proliferate in response to presentation of the peptide on the APC or cancer cell. In other embodiments, reference to modulation of the immune response involves, either or both the humoral and cell-mediated arms of the immune system, which is accompanied by the presence of Th2 and Th1 T helper cells, respectively, or in another embodiment, each arm individually.

In other embodiments, the methods affecting the growth of a tumor result in (1) the direct inhibition of tumor cell division, or (2) immune cell mediated tumor cell lysis, or both, which leads to a suppression in the net expansion of tumor cells.

Inhibition of tumor growth by either of these two mechanisms can be readily determined by one of ordinary skill in the art based upon a number of well known methods. In another embodiment, tumor inhibition is determined by measuring the actual tumor size over a period of time. In another embodiment, tumor inhibition can be determined by estimating the size of a tumor (over a period of time) utilizing methods well known to those of skill in the art. More specifically, a variety of radiologic imaging methods (e.g., single photon and positron emission computerized tomography; see generally, "Nuclear Medicine in Clinical Oncology," Winkler, C. (ed.)

Springer-Verlag, New York, 1986), can be utilized to estimate tumor size. Such methods can also utilize a variety of imaging agents, including for example, conventional imaging agents (e.g., Gallium-67 citrate), as well as specialized reagents for metabolite imaging, receptor imaging, or immunologic imaging (e.g., radiolabeled monoclonal antibody specific tumor markers). In addition, non-radioactive methods such as ultrasound (see, "Ultrasonic Differential Diagnosis of Tumors", Kossoff and Fukuda, (eds.), Igaku-Shoin, New York, 1984), can also be utilized to estimate the size of a tumor.

In addition to the in vivo methods for determining tumor inhibition discussed above, a variety of in vitro methods can be utilized in order to predict in vivo tumor inhibition. Representative examples include lymphocyte mediated anti-tumor cytolytic activity determined for example, by a $^{51}$Cr release assay (Examples), tumor dependent lymphocyte proliferation (Ioannides, et al., J. Immunol. 146(5):1700-1707, 1991), in vitro generation of tumor specific antibodies (Herlyn, et al., J. Immunol. Meth. 73:157-167, 1984), cell (e.g., CTL, helper T-cell) or humoral (e.g., antibody) mediated inhibition of cell growth in vitro (Gazit, et al., Cancer Immunol Immunother 35:135-144, 1992), and, for any of these assays, determination of cell precursor frequency (Vose, Int. J. Cancer 30:135-142 (1982), and others.

In another embodiment, methods of suppressing tumor growth indicate a growth state that is curtailed compared to growth without contact with, or exposure to a peptide of this invention. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth refers, in other embodiments, to slowing, delaying, or stopping tumor growth, or to tumor shrinkage. Each possibility represents a separate embodiment of the present invention.

In another embodiment of methods and compositions of the present invention, WT1 expression is measured. In another embodiment, WT1 transcript expression is measured. In another embodiment, WT1 protein levels in the tumor are measured. Each possibility represents a separate embodiment of the present invention.

Methods of determining the presence and magnitude of an immune response are well known in the art. In another embodiment, lymphocyte proliferation assays, wherein T cell uptake of a radioactive substance, e.g. $^3$H-thymidine is measured as a function of cell proliferation. In other embodiments, detection of T cell proliferation is accomplished by measuring increases in interleukin-2 (IL-2) production, Ca$^{2+}$ flux, or dye uptake, such as 3-(4,5-dimethylthiazol-2-yl)-2,5-diphenyl-tetrazolium. Each possibility represents a separate embodiment of the present invention.

In another embodiment, CTL stimulation is determined by means known to those skilled in the art, including, detection of cell proliferation, cytokine production and others. Analysis of the types and quantities of cytokines secreted by T cells upon contacting ligand-pulsed targets can be a measure of functional activity. Cytokines can be measured by ELISA or ELISPOT assays to determine the rate and total amount of cytokine production. (Fujihashi K. et al. (1993) J. Immunol. Meth. 160:181; Tanguay S. and Killion J. J. (1994) Lymphokine Cytokine Res. 13:259).

In another embodiment, CTL activity is determined by $^{51}$Cr-release lysis assay. Lysis of peptide-pulsed $^{51}$Cr-labeled targets by antigen-specific T cells can be compared for target cells pulsed with control peptide. In another embodiment, T cells are stimulated with a peptide of this invention, and lysis of target cells expressing the native peptide in the context of MHC can be determined. The kinetics of lysis as well as overall target lysis at a fixed timepoint (e.g., 4 hours) are used, in another embodiment, to evaluate ligand performance. (Ware C. F. et al. (1983) J Immunol 131: 1312).

Methods of determining affinity of a peptide for an HLA molecule are well known in the art. In another embodiment, affinity is determined by TAP stabilization assays (Examples).

In another embodiment, affinity is determined by competition radioimmunoassay. In another embodiment, the following protocol is utilized. Target cells are washed two times in PBS with 1% bovine serum albumin (BSA; Fisher Chemicals, Fairlawn, N.J.). Cells are resuspended at 10$^7$/ml on ice, and the native cell surface bound peptides are stripped for 2 minutes at 0° C. using citrate-phosphate buffer in the presence of 3 mg/ml beta$_2$ microglobulin. The pellet is resuspended at 5×10$^6$ cells/ml in PBS/1% BSA in the presence of 3 mg/ml beta$_2$ microglobulin and 30 mg/ml deoxyribonuclease, and 200 ml aliquots are incubated in the presence or absence of HLA-specific peptides for 10 min at 20° C., then with $^{125}$I-labeled peptide for 30 min at 20° C. Total bound $^{125}$I is determined after two washes with PBS/2% BSA and one wash with PBS. Relative affinities are determined by comparison of escalating concentrations of the test peptide versus a known binding peptide.

In another embodiment, a specificity analysis of the binding of peptide to HLA on surface of live cells (e.g. SKLY-16 cells) is conducted to confirm that the binding is to the appropriate HLA molecule and to characterize its restriction. This includes, in another embodiment, competition with excess unlabeled peptides known to bind to the same or disparate HLA molecules and use of target cells which express the same or disparate HLA types. This assay is performed, in another embodiment, on live fresh or 0.25% paraformaldehyde-fixed human PBMC, leukemia cell lines and EBV-transformed T-cell lines of specific HLA types. The relative avidity of the peptides found to bind MHC molecules on the specific cells are assayed by competition assays as described above against $^{125}$I-labeled peptides of known high affinity for the relevant HLA molecule, e.g., tyrosinase or HBV peptide sequence.

In another embodiment, an HLA class II-binding peptide of methods and compositions of the present invention is longer than the minimum length for binding to an HLA class II molecule, which is, in another embodiment, about 12 AA. In another embodiment, increasing the length of the HLA class II-binding peptide enables binding to more than one HLA class II molecule. In another embodiment, increasing the length enables binding to an HLA class II molecule whose binding motif is not known. In another embodiment, increasing the length enables binding to an HLA class I molecule. In another embodiment, the binding motif of the HLA class I molecule is known. In another embodiment, the binding motif of the HLA class I molecule is not known. Each possibility represents a separate embodiment of the present invention.

In another embodiment, the peptides utilized in methods and compositions of the present invention comprise a non-classical amino acid such as: 1,2,3,4-tetrahydroisoquinoline-3-carboxylate (Kazmierski et al. (1991) J. Am. Chem. Soc. 113:2275-2283); (2S,3S)-methyl-phenylalanine, (2S,3R)-methyl-phenylalanine, (2R,3S)-methyl-phenylalanine and (2R,3R)-methyl-phenylalanine (Kazmierski and Hruby (1991) Tetrahedron Lett. 32(41): 5769-5772); 2-aminotetrahydronaphthalene-2-carboxylic acid (Landis (1989) Ph.D. Thesis, University of Arizona); hydroxy-1,2,3,4-tetrahydroisoquinoline-3-carboxylate (Miyake et al. (1984) J.

Takeda Res. Labs. 43:53-76) histidine isoquinoline carboxylic acid (Zechel et al. (1991) Int. J. Pep. Protein Res. 38(2): 131-138); and HIC (histidine cyclic urea), (Dharanipragada et al. (1993) Int. J. Pep. Protein Res. 42(1):68-77) and ((1992) Acta. Crst., Crystal Struc. Comm. 48(IV):1239-124).

In another embodiment, a peptide of this invention comprises an AA analog or peptidomimetic, which, in other embodiments, induces or favors specific secondary structures. Such peptides comprise, in other embodiments, the following: LL-Acp (LL-3-amino-2-propenidone-6-carboxylic acid), a β-turn inducing dipeptide analog (Kemp et al. (1985) J. Org. Chem. 50:5834-5838); β-sheet inducing analogs (Kemp et al. (1988) Tetrahedron Lett. 29:5081-5082); β-turn inducing analogs (Kemp et al. (1988) Tetrahedron Lett. 29:5057-5060); alpha-helix inducing analogs (Kemp et al. (1988) Tetrahedron Lett. 29:4935-4938); gamma-turn inducing analogs (Kemp et al. (1989) J. Org. Chem. 54:109:115); analogs provided by the following references: Nagai and Sato (1985) Tetrahedron Lett. 26:647-650; and DiMaio et al. (1989) J. Chem. Soc. Perkin Trans. p. 1687; a Gly-Ala turn analog (Kahn et al. (1989) Tetrahedron Lett. 30:2317); amide bond isostere (Jones et al. (1988) Tetrahedron Lett. 29(31): 3853-3856); tretrazol (Zabrocki et al. (1988) J. Am. Chem. Soc. 110:5875-5880); DTC (Samanen et al. (1990) Int. J. Protein Pep. Res. 35:501:509); and analogs taught in Olson et al. (1990) J. Am. Chem. Sci. 112:323-333 and Garvey et al. (1990) J. Org. Chem. 55(3):936-940. Confoiniationally restricted mimetics of beta turns and beta bulges, and peptides containing them, are described in U.S. Pat. No. 5,440,013, issued Aug. 8, 1995 to Kahn.

In other embodiments, a peptide of this invention is conjugated to one of various other molecules, as described hereinbelow, which can be via covalent or non-covalent linkage (complexed), the nature of which varies, in another embodiment, depending on the particular purpose. In another embodiment, the peptide is covalently or non-covalently complexed to a macromolecular carrier, (e.g. an immunogenic carrier), including, but not limited to, natural and synthetic polymers, proteins, polysaccharides, polypeptides (amino acids), polyvinyl alcohol, polyvinyl pyrrolidone, and lipids. In another embodiment, a peptide of this invention is linked to a substrate. In another embodiment, the peptide is conjugated to a fatty acid, for introduction into a liposome (U.S. Pat. No. 5,837,249). In another embodiment, a peptide of the invention is complexed covalently or non-covalently with a solid support, a variety of which are known in the art. In another embodiment, linkage of the peptide to the carrier, substrate, fatty acid, or solid support serves to increase an elicited an immune response.

In other embodiments, the carrier is thyroglobulin, an albumin (e.g. human serum albumin), tetanus toxoid, polyamino acids such as poly (lysine: glutamic acid), an influenza protein, hepatitis B virus core protein, keyhole limpet hemocyanin, an albumin, or another carrier protein or carrier peptide; hepatitis B virus recombinant vaccine, or an APC. Each possibility represents a separate embodiment of the present invention.

In another embodiment, the term "amino acid" (AA) refers to a natural or, in another embodiment, an unnatural or synthetic AA, and can include, in other embodiments, glycine, D- or L optical isomers, AA analogs, peptidomimetics, or combinations thereof.

In another embodiment, the terms "cancer," "neoplasm," "neoplastic" or "tumor," are used interchangeably and refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. In another embodiment, a tumor is detectable on the basis of tumor mass; e.g., by such procedures as CAT scan, magnetic resonance imaging (MRI), X-ray, ultrasound or palpation, and in another embodiment, is identified by biochemical or immunologic findings, the latter which is used to identify cancerous cells, as well, in other embodiments.

Methods for synthesizing peptides are well known in the art. In another embodiment, the peptides of this invention are synthesized using an appropriate solid-state synthetic procedure (see for example, Steward and Young, *Solid Phase Peptide Synthesis*, Freemantle, San Francisco, Calif. (1968); Merrifield (1967) Recent Progress in Hormone Res 23: 451). The activity of these peptides is tested, in other embodiments, using assays as described herein.

In another embodiment, the peptides of this invention are purified by standard methods including chromatography (e.g., ion exchange, affinity, and sizing column chromatography), centrifugation, differential solubility, or by any other standard technique for protein purification. In another embodiment, immuno-affinity chromatography is used, whereby an epitope is isolated by binding it to an affinity column comprising antibodies that were raised against that peptide, or a related peptide of the invention, and were affixed to a stationary support.

In another embodiment, affinity tags such as hexa-His (Invitrogen), Maltose binding domain (New England Biolabs), influenza coat sequence (Kolodziej et al. (1991) Meth. Enzymol. 194:508-509), glutathione-S-transferase, or others, are attached to the peptides of this invention to allow easy purification by passage over an appropriate affinity column. Isolated peptides can also be physically characterized, in other embodiments, using such techniques as proteolysis, nuclear magnetic resonance, and x-ray crystallography.

In another embodiment, the peptides of this invention are produced by in vitro translation, through known techniques, as will be evident to one skilled in the art. In another embodiment, the peptides are differentially modified during or after translation, e.g., by phosphorylation, glycosylation, cross-linking, acylation, proteolytic cleavage, linkage to an antibody molecule, membrane molecule or other ligand, (Ferguson et al. (1988) Ann. Rev. Biochem. 57:285-320).

In another embodiment, the peptides of this invention further comprise a detectable label, which in another embodiment, is fluorescent, or in another embodiment, luminescent, or in another embodiment, radioactive, or in another embodiment, electron dense. In other embodiments, the dectectable label comprises, for example, green fluorescent protein (GFP), DS-Red (red fluorescent protein), secreted alkaline phosphatase (SEAP), beta-galactosidase, luciferase, $^{32}P$ $^{125}I$, $^3H$ and $^{14}C$, fluorescein and its derivatives, rhodamine and its derivatives, dansyl and umbelliferone, luciferin or any number of other such labels known to one skilled in the art. The particular label used will depend upon the type of immunoassay used.

In another embodiment, a peptide of this invention is linked to a substrate, which, in another embodiment, serves as a carrier. In another embodiment, linkage of the peptide to a substrate serves to increase an elicited an immune response.

In another embodiment, peptides of this invention are linked to other molecules, as described herein, using conventional cross-linking agents such as carbodimides. Examples of carbodimides are 1-cyclohexyl-3-(2-morpholinyl-(4-ethyl)carbodiimide (CMC), 1-ethyl-3-(3-dimethyaminopropyl)carbodiimide (EDC) and 1-ethyl-3-(4-azonia-44-dimethylpentyl)carbodiimide.

In other embodiments, the cross-linking agents comprise cyanogen bromide, glutaraldehyde and succinic anhydride. In general, any of a number of homo-bifunctional agents including a homo-bifunctional aldehyde, a homo-bifunctional epoxide, a homo-bifunctional imido-ester, a homo-bifunctional N-hydroxysuccinimide ester, a homo-bifunctional maleimide, a homo-bifunctional alkyl halide, a homo-bifunctional pyridyl disulfide, a homo-bifunctional aryl halide, a homo-bifunctional hydrazide, a homo-bifunctional diazonium derivative and a homo-bifunctional photoreactive compound can be used. Also envisioned, in other embodiments, are hetero-bifunctional compounds, for example, compounds having an amine-reactive and a sulfhydryl-reactive group, compounds with an amine-reactive and a photoreactive group and compounds with a carbonyl-reactive and a sulfhydryl-reactive group.

In other embodiments, the homo-bifunctional cross-linking agents include the bifunctional N-hydroxysuccinimide esters dithiobis(succinimidylpropionate), disuccinimidyl suberate, and disuccinimidyl tartarate; the bifunctional imido-esters dimethyl adipimidate, dimethyl pimelimidate, and dimethyl suberimidate; the bifunctional sulfhydryl-reactive crosslinkers 1,4-di-[3'-(2'-pyridyldithio)propionamido] butane, bismaleimidohexane, and bis-N-maleimido-1,8-octane; the bifunctional aryl halides 1,5-difluoro-2,4-dinitrobenzene and 4,4'-difluoro-3,3'-dinitrophenylsulfone; bifunctional photoreactive agents such as bis-[b-(4-azidosalicylamido)ethyl]disulfide; the bifunctional aldehydes formaldehyde, malondialdehyde, succinaldehyde, glutaraldehyde, and adipaldehyde; a bifunctional epoxide such as 1,4-butaneodiol diglycidyl ether; the bifunctional hydrazides adipic acid dihydrazide, carbohydrazide, and succinic acid dihydrazide; the bifunctional diazoniums o-tolidine, diazotized and bis-diazotized benzidine; the bifunctional alkylhalides N1N'-ethylene-bis(iodoacetamide), N1N'-hexamethylene-bis(iodoacetamide), N1N'-undecamethylene-bis(iodoacetamide), as well as benzylhalides and halomustards, such as a1a'-diiodo-p-xylene sulfonic acid and tri(2-chloroethyl) amine, respectively.

In other embodiments, hetero-bifunctional cross-linking agents used to link the peptides to other molecules, as described herein, include, but are not limited to, SMCC (succinimidyl-4-(N-maleimidomethyl)cyclohexane-1-carboxylate), MB S (m-maleimidobenzoyl-N-hydroxysuccinimide ester), SIAB (N-succinimidyl(4-iodoacteyl)aminobenzoate), SMPB (succinimidyl-4-(p-maleimidophenyl)butyrate), GMBS (N-(.gamma.-maleimidobutyryloxy)succinimide ester), MPBH (4-(4-N-maleimidopohenyl)butyric acid hydrazide), M2C2H (4-(N-maleimidomethyl)cyclohexane-1-carboxyl-hydrazide), SMPT (succinimidyloxycarbonyl-a-methyl-a-(2-pyridyldithio)toluene), and SPDP (N-succinimidyl 3-(2-pyridyldithio)propionate).

In another embodiment, the peptides of the invention are formulated as non-covalent attachment of monomers through ionic, adsorptive, or biospecific interactions. Complexes of peptides with highly positively or negatively charged molecules can be accomplished, in another embodiment, through salt bridge formation under low ionic strength environments, such as in deionized water. Large complexes can be created, in another embodiment, using charged polymers such as poly-(L-glutamic acid) or poly-(L-lysine), which contain numerous negative and positive charges, respectively. In another embodiment, peptides are adsorbed to surfaces such as microparticle latex beads or to other hydrophobic polymers, forming non-covalently associated peptide-superantigen complexes effectively mimicking cross-linked or chemically polymerized protein, in other embodiments. In another embodiment, peptides are non-covalently linked through the use of biospecific interactions between other molecules. For instance, utilization of the strong affinity of biotin for proteins such as avidin or streptavidin or their derivatives could be used to form peptide complexes. The peptides, according to this aspect, and in another embodiment, can be modified to possess biotin groups using common biotinylation reagents such as the N-hydroxysuccinimidyl ester of D-biotin (NHS-biotin), which reacts with available amine groups.

In another embodiment, a peptide of the present invention is linked to a carrier. In another embodiment, the carrier is KLH. In other embodiments, the carrier is any other carrier known in the art, including, for example, thyroglobulin, albumins such as human serum albumin, tetanus toxoid, polyamino acids such as poly (lysine:glutamic acid), influenza, hepatitis B virus core protein, hepatitis B virus recombinant vaccine and the like. Each possibility represents a separate embodiment of the present invention.

In another embodiment, the peptides of this invention are conjugated to a lipid, such as P3 CSS. In another embodiment, the peptides of this invention are conjugated to a bead.

In another embodiment, the compositions of this invention further comprise immunomodulating compounds. In other embodiments, the immunomodulating compound is a cytokine, chemokine, or complement component that enhances expression of immune system accessory or adhesion molecules, their receptors, or combinations thereof. In some embodiments, the immunomodulating compound include interleukins, for example interleukins 1 to 15, interferons alpha, beta or gamma, tumour necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MIP-1a and MIP-1b, complement components, or combinations thereof. In other embodiments, the immunomodulating compound stimulate expression, or enhanced expression of OX40, OX40L (gp34), lymphotactin, CD40, CD40L, B7.1, B7.2, TRAP, ICAM-1, 2 or 3, cytokine receptors, or combination thereof.

In another embodiment, the immunomodulatory compound induces or enhances expression of co-stimulatory molecules that participate in the immune response, which include, in some embodiments, CD40 or its ligand, CD28, CTLA-4 or a B7 molecule. In another embodiment, the immunomodulatory compound induces or enhances expression of a heat stable antigen (HSA) (Liu Y. et al. (1992) J. Exp. Med. 175:437-445), chondroitin sulfate-modified MHC invariant chain (Ii-CS) (Naujokas M. F. et al. (1993) Cell 74:257-268), or an intracellular adhesion molecule 1 (ICAM-1) (Van R. H. (1992) Cell 71:1065-1068), which assists, in another embodiment, co-stimulation by interacting with their cognate ligands on the T cells.

In another embodiment, the composition comprises a solvent, including water, dispersion media, cell culture media, isotonic agents and the like. In another embodiment, the solvent is an aqueous isotonic buffered solution with a pH of around 7.0. In another embodiment, the composition comprises a diluent such as water, phosphate buffered saline, or saline. In another embodiment, the composition comprises a solvent, which is non-aqueous, such as propyl ethylene glycol, polyethylene glycol and vegetable oils.

In another embodiment, the composition is formulated for administration by any of the many techniques known to those of skill in the art. For example, this invention provides for administration of the pharmaceutical composition parenterally, intravenously, subcutaneously, intradermally, intramucosally, topically, orally, or by inhalation.

In another embodiment, the vaccine comprising a peptide of this invention further comprises a cell population, which, in another embodiment, comprises lymphocytes, monocytes, macrophages, dendritic cells, endothelial cells, stem cells or combinations thereof, which, in another embodiment are autologous, syngeneic or allogeneic, with respect to each other. In another embodiment, the cell population comprises a peptide of the present invention. In another embodiment, the cell population takes up the peptide. Each possibility represents a separate embodiment of the present invention.

In another embodiment, the cell populations of this invention are obtained from in vivo sources, such as, for example, peripheral blood, leukophoresis blood product, apheresis blood product, peripheral lymph nodes, gut associated lymphoid tissue, spleen, thymus, cord blood, mesenteric lymph nodes, liver, sites of immunologic lesions, e.g. synovial fluid, pancreas, cerebrospinal fluid, tumor samples, granulomatous tissue, or any other source where such cells can be obtained. In another embodiment, the cell populations are obtained from human sources, which are, in other embodiments, from human fetal, neonatal, child, or adult sources. In another embodiment, the cell populations of this invention are obtained from animal sources, such as, for example, porcine or simian, or any other animal of interest. In another embodiment, the cell populations of this invention are obtained from subjects that are normal, or in another embodiment, diseased, or in another embodiment, susceptible to a disease of interest.

In another embodiment, the cell populations of this invention are separated via affinity-based separation methods. Techniques for affinity separation include, in other embodiments, magnetic separation, using antibody-coated magnetic beads, affinity chromatography, cytotoxic agents joined to a monoclonal antibody or use in conjunction with a monoclonal antibody, for example, complement and cytotoxins, and "panning" with an antibody attached to a solid matrix, such as a plate, or any other convenient technique. In other embodiment, separation techniques include the use of fluorescence activated cell sorters, which can have varying degrees of sophistication, such as multiple color channels, low angle and obtuse light scattering detecting channels, impedance channels, etc. In other embodiments, any technique that enables separation of the cell populations of this invention can be employed, and is to be considered as part of this invention.

In another embodiment, the dendritic cells are from the diverse population of morphologically similar cell types found in a variety of lymphoid and non-lymphoid tissues, qualified as such (Steinman (1991) Ann. Rev. Immunol. 9:271-296). In another embodiment, the dendritic cells used in this invention are isolated from bone marrow, or in another embodiment, derived from bone marrow progenitor cells, or, in another embodiment, from isolated from/derived from peripheral blood, or in another embodiment, derived from, or are a cell line.

In another embodiment, the cell populations described herein are isolated from the white blood cell fraction of a mammal, such as a murine, simian or a human (See, e.g., WO 96/23060). The white blood cell fraction can be, in another embodiment, isolated from the peripheral blood of the mammal.

Methods of isolating dendritic cells are well known in the art. In another embodiment, the DC are isolated via a method which includes the following steps: (a) providing a white blood cell fraction obtained from a mammalian source by methods known in the art such as leukophoresis; (b) separating the white blood cell fraction of step (a) into four or more subfractions by countercurrent centrifugal elutriation; (c) stimulating conversion of monocytes in one or more fractions from step (b) to dendritic cells by contacting the cells with calcium ionophore, GM-CSF and IL-13 or GM-CSF and IL-4, (d) identifying the dendritic cell-enriched fraction from step (c); and (e) collecting the enriched fraction of step (d), preferably at about 4° C.

In another embodiment, the dendritic cell-enriched fraction is identified by fluorescence-activated cell sorting, which identifies at least one of the following markers: HLA-DR, HLA-DQ, or B7.2, and the simultaneous absence of the following markers: CD3, CD14, CD16, 56, 57, and CD 19, 20.

In another embodiment, the cell population comprises lymphocytes, which are, in another embodiment, T cells, or in another embodiment, B cells. The T cells are, in other embodiments, characterized as NK cells, helper T cells, cytotoxic T lymphocytes (CTL), TILs, naïve T cells, or combinations thereof. It is to be understood that T cells which are primary, or cell lines, clones, etc. are to be considered as part of this invention. In another embodiment, the T cells are CTL, or CTL lines, CTL clones, or CTLs isolated from tumor, inflammatory, or other infiltrates.

In another embodiment, hematopoietic stem or early progenitor cells comprise the cell populations used in this invention. In another embodiment, such populations are isolated or derived, by leukaphoresis. In another embodiment, the leukapheresis follows cytokine administration, from bone marrow, peripheral blood (PB) or neonatal umbilical cord blood. In another embodiment, the stem or progenitor cells are characterized by their surface expression of the surface antigen marker known as $CD34^+$, and exclusion of expression of the surface lineage antigen markers, Lin−.

In another embodiment, the subject is administered a peptide, composition or vaccine of this invention, in conjunction with bone marrow cells. In another embodiment, the administration together with bone marrow cells embodiment follows previous irradiation of the subject, as part of the course of therapy, in order to suppress, inhibit or treat cancer in the subject.

In another embodiment, the phrase "contacting a cell" or "contacting a population" refers to a method of exposure, which can be, in other embodiments, direct or indirect. In another embodiment, such contact comprises direct injection of the cell through any means well known in the art, such as microinjection. It is also envisaged, in another embodiment, that supply to the cell is indirect, such as via provision in a culture medium that surrounds the cell, or administration to a subject, via any route well known in the art, and as described herein.

In another embodiment, CTL generation of methods of the present invention is accomplished in vivo, and is effected by introducing into a subject an antigen presenting cell contacted in vitro with a peptide of this invention (See for example Paglia et al. (1996) J. Exp. Med. 183:317-322).

In another embodiment, the peptides of methods and compositions of the present invention are delivered to APC. In another embodiment, the peptide-pulsed APC are administered to a subject to elicit and immune response or treat or inhibit growth or recurrence of a tumor. Each possibility represents a separate embodiment of the present invention.

In another embodiment, the peptides are delivered to APC in the form of cDNA encoding the peptides. In another embodiment, the term "antigen-presenting cells" (APC) refers to dendritic cells (DC), monocytes/macrophages, B lymphocytes or other cell type(s) expressing the necessary MHC/co-stimulatory molecules, which effectively allow for T cell recognition of the presented peptide. In another embodiment, the APC is a cancer cell. Each possibility represents a separate embodiment of the present invention.

In another embodiment, the CTL are contacted with 2 or more APC populations. In another embodiment, the 2 or more APC populations present different peptides. Each possibility represents a separate embodiment of the present invention.

In another embodiment, techniques that lead to the expression of antigen in the cytosol of APC (e.g. DC) are used to deliver the peptides to the APC. Methods for expressing antigens on APC are well known in the art. In another embodiment, the techniques include (1) the introduction into the APC of naked DNA encoding a peptide of this invention, (2) infection of APC with recombinant vectors expressing a peptide of this invention, and (3) introduction of a peptide of this invention into the cytosol of an APC using liposomes. (See Boczkowski D. et al. (1996) J. Exp. Med. 184:465-472; Rouse et al. (1994) J. Virol. 68:5685-5689; and Nair et al. (1992) J. Exp. Med. 175:609-612).

In another embodiment, foster APC such as those derived from the human cell line 174xCEM.T2, referred to as T2, which contains a mutation in its antigen processing pathway that restricts the association of endogenous peptides with cell surface MHC class I molecules (Zweerink et al. (1993) J. Immunol. 150:1763-1771), are used, as exemplified herein.

In another embodiment, as described herein, the subject is exposed to a peptide, or a composition/cell population comprising a peptide of this invention, which differs from the native protein expressed, wherein subsequently a host immune cross-reactive with the native protein/antigen develops.

In another embodiment, the subject, as referred to in any of the methods or embodiments of this invention is a human. In other embodiments, the subject is a mammal, which can be a mouse, rat, rabbit, hamster, guinea pig, horse, cow, sheep, goat, pig, cat, dog, monkey, or ape. Each possibility represents a separate embodiment of the present invention.

In another embodiment, peptides, vaccines, and compositions of this invention stimulate an immune response that results in tumor cell lysis.

In another embodiment, any of the methods described herein is used to elicit CTL, which are elicited in vitro. In another embodiment, the CTL are elicited ex-vivo. In another embodiment, the CTL are elicited in vitro. The resulting CTL, are, in another embodiment, administered to the subject, thereby treating the condition associated with the peptide, an expression product comprising the peptide, or a homologue thereof. Each possibility represents a separate embodiment of the present invention.

In another embodiment, the method entails introduction of the genetic sequence that encodes the peptides of this invention using, e.g., one or more nucleic acid delivery techniques. Nucleic acids of the invention include, in another embodiment, DNA, RNA and mixtures of DNA and RNA, alone or in conjunction with non-nucleic acid components. In another embodiment, the method comprises administering to the subject a vector comprising a nucleotide sequence, which encodes a peptide of the present invention (Tindle, R. W. et al. Virology (1994) 200:54). In another embodiment, the method comprises administering to the subject naked DNA which encodes a peptide, or in another embodiment, two or more peptides of this invention (Nabel, et al. PNAS-USA (1990) 90: 11307). In another embodiment, multi-epitope, analogue-based cancer vaccines are utilized (Fikes et al, Design of multi-epitope, analogue-based cancer vaccines. Expert Opin Biol Ther. 2003 September; 3(6):985-93). Each possibility represents a separate embodiment of the present invention.

Nucleic acids can be administered to a subject via any means as is known in the art, including parenteral or intravenous administration, or in another embodiment, by means of a gene gun. In another embodiment, the nucleic acids are administered in a composition, which correspond, in other embodiments, to any embodiment listed herein.

Vectors for use according to methods of this invention can comprise any vector that facilitates or allows for the expression of a peptide of this invention. Vectors comprises, in some embodiments, attenuated viruses, such as vaccinia or fowlpox, such as described in, e.g., U.S. Pat. No. 4,722,848, incorporated herein by reference. In another embodiment, the vector is BCG (Bacille Calmette Guerin), such as described in Stover et al. (Nature 351:456-460 (1991)). A wide variety of other vectors useful for therapeutic administration or immunization of the peptides of the invention, e.g., *Salmonella typhi* vectors and the like, will be apparent to those skilled in the art from the description herein.

In another embodiment, the vector further encodes for an immunomodulatory compound, as described herein. In another embodiment, the subject is administered an additional vector encoding same, concurrent, prior to or following administration of the vector encoding a peptide of this invention to the subject.

In another embodiment, the peptides, compositions and vaccines of this invention are administered to a subject, or utilized in the methods of this invention, in combination with other anti-cancer compounds and chemotherapeutics, including monoclonal antibodies directed against alternate cancer antigens, or, in another embodiment, epitopes that consist of an AA sequence which corresponds to, or in part to, that from which the peptides of this invention are derived.

Various embodiments of dosage ranges are contemplated by this invention. In another embodiment, the dosage is 20 µg per peptide per day. In another embodiment, the dosage is 10 µg/peptide/day. In another embodiment, the dosage is 30 µg/peptide/day. In another embodiment, the dosage is 40 µg/peptide/day. In another embodiment, the dosage is 60 µg/peptide/day. In another embodiment, the dosage is 80 µg/peptide/day. In another embodiment, the dosage is 100 µg/peptide/day. In another embodiment, the dosage is 150 µg/peptide/day. In another embodiment, the dosage is 200 µg/peptide/day. In another embodiment, the dosage is 300 µg/peptide/day. In another embodiment, the dosage is 400 µg/peptide/day. In another embodiment, the dosage is 600 µg/peptide/day. In another embodiment, the dosage is 800 µg/peptide/day. In another embodiment, the dosage is 1000 µg/peptide/day. In another embodiment, the dosage is 1500 µg/peptide/day. In another embodiment, the dosage is 2000 µg/peptide/day.

In another embodiment, the dosage is 10 µg/peptide/dose. In another embodiment, the dosage is 30 µg/peptide/dose. In another embodiment, the dosage is 40 µg/peptide/dose. In another embodiment, the dosage is 60 µg/peptide/dose. In another embodiment, the dosage is 80 µg/peptide/dose. In another embodiment, the dosage is 100 µg/peptide/dose. In another embodiment, the dosage is 150 µg/peptide/dose. In another embodiment, the dosage is 200 µg/peptide/dose. In another embodiment, the dosage is 300 µg/peptide/dose. In another embodiment, the dosage is 400 µg/peptide/dose. In another embodiment, the dosage is 600 µg/peptide/dose. In another embodiment, the dosage is 800 µg/peptide/dose. In another embodiment, the dosage is 1000 µg/peptide/dose. In another embodiment, the dosage is 1500 µg/peptide/dose. In another embodiment, the dosage is 2000 µg/peptide/dose.

In another embodiment, the dosage is 10-20 µg/peptide/dose. In another embodiment, the dosage is 20-30 µg/peptide/dose. In another embodiment, the dosage is 20-40 µg/peptide/dose. In another embodiment, the dosage is 30-60 µg/peptide/dose. In another embodiment, the dosage is 40-80 µg/peptide/dose. In another embodiment, the dosage is 50-100 µg/peptide/dose. In another embodiment, the dosage is 50-150 µg/peptide/dose. In another embodiment, the dosage is 100-200 µg/peptide/dose. In another embodiment, the dosage is 200-300 µg/peptide/dose. In another embodiment, the dosage is 300-400 µg/peptide/dose. In another embodiment, the dosage is 400-600 µg/peptide/dose. In another embodiment, the dosage is 500-800 µg/peptide/dose. In another embodiment, the dosage is 800-1000 µg/peptide/dose. In another embodiment, the dosage is 1000-1500 µg/peptide/dose. In another embodiment, the dosage is 1500-2000 µg/peptide/dose.

In another embodiment, the total amount of peptide per dose or per day is one of the above amounts. In another embodiment, the total peptide dose per dose is one of the above amounts.

Each of the above doses represents a separate embodiment of the present invention.

EXPERIMENTAL DETAILS SECTION

Example 1

Binding of HLA-A0201 and -A0301 by Synthetic Peptide Analogues Derived from WT1

Materials and Experimental Methods

Peptides

Peptides were synthesized by Genemed Synthesis Inc, CA using fluorenylmethoxycarbonyl chemistry and solid phase synthesis, and were purified by high pressure liquid chromatography (HPLC). The quality of the peptides was assessed by HPLC analysis, and the expected molecular weight was measured using matrix-assisted laser desorption mass spectrometry. Peptides were sterile and >90% pure. The peptides were dissolved in DMSO and diluted in PBS at pH 7.4 or saline solution to yield a concentration of 5 milligrams per milliliter (mg/ml) and were stored at −80° C. For in vitro experiments, an irrelevant control peptide, HLA A24 consensus, was used.

Peptide Sequence Analysis

Peptide sequence analysis was performed using 2 databases. The first was the software of the Bioinformatics & Molecular Analysis Section (National Institutes of Health, Washington, D.C.) (Parker K C et al, Scheme for ranking potential HLA-A2 binding peptides based on independent binding of individual peptide side-chains. J Immunol 152: 163-175, 1994), which ranks 9-mer or 10-mer peptides on a predicted half-time dissociation coefficient from HLA class I molecules. The second database, SYFPEITHI prediction software, is described in Rammensee H G et al (SYFPEITHI: database for MHC ligands and peptide motifs. Immunogenetics 50: 213-219, 1999). Irrelevant control peptides used for in vitro experiments were: RAS (TEYKLVVVGAPGVGK-SALTIQ; SEQ ID No: 46) or CML b2a2 (VHSIPLTINKEE-ALQRPVASDFE; SEQ ID No: 47) for Class II, and HIV pol (ILKEPVHGV; SEQ ID No: 48) or CML F (YLKALQRPY; SEQ ID No: 49) for Class I.

Cell Lines

Cell lines were cultured in RPMI 1640 medium supplemented with 5% FCS, penicillin, streptomycin, 2 mM glutamine and 2-mercaptoethanol at 37° C. in humidified air containing 5% $CO_2$. T2 is a human cell line lacking TAP1 and TAP2 and therefore unable to present peptides derived from cytosolic proteins. Raji cells are a human Burkitt lymphoma cells that exhibit a high level of TAP expression.

Human mesothelioma cell lines studied included: sarcomatoid (VAMT, H2373, H28), epithelioid (H2452) and biphasic (JMN, MSTO and H-Meso1A). Cell lines were obtained from the following sources: H-Meso1A: NCI, Bethesda, Md.; JMN and VAMT: Dr. Sirotnak, Memorial Sloan Kettering Cancer Center (MSKCC); H-2452 and H2373: Dr. Pass, Karmanos Cancer Institute, Wayne State University, Detroit, Mich.; H28 and MSTO: American Type Culture Collection (ATCC, Manassas, Va.). Cell lines were maintained in media recommended by the suppliers and incubated in a humidified incubator with 5% $CO_2$.

Mesothelioma cell lines Meso 11, Meso 34, Meso 37, Meso 47 and Meso 56 were obtained from Dr. M Gregoire (Institute of Biology, Nantes, France) and cultured in RPMI 1640 (Life Technologies)+10% fetal calf serum (FCS), 1% penicillin-streptomycin, and 1% L-glutamine. All cells were HLA typed by the Department of Cellular Immunology at MSKCC. Melanoma cell line Mewo (WT1$^-$ A201$^+$) was obtained from the ATCC. SKRC-52 renal cell carcinoma was obtained from L. Old of the Ludwig Institute. Leukemia cell lines were cultured in RPMI 1640+10% FCS, 1% penicillin-streptomycin, 2 mM glutamine and 2-mercaptoethanol at 37° C./5% $CO_2$. LAMA81, BV173 and 697, Ph$^+$ leukemias that are all WT1$^+$ and A0201$^+$, were provided by Dr. H J Stauss (University College London). SKLY-16 is a human B cell lymphoma (WT1, A0201$^+$); K562, RwLeu4 and HL60, all WT1$^+$ leukemias, were obtained from the ATCC.

T2 Assay for Peptide Binding and Stabilization of HLA A0201 Molecules

T2 cells (TAP$^-$, HLA-A0201$^+$) were incubated overnight at 27° C. at a concentration of 1×10$^6$ cells/ml in FCS-free RPMI medium supplemented with 5 µg/ml human $β_2$m (Sigma, St Louis, Mo.) in the absence (negative control) or presence of either a positive reference tyrosinase peptide or test peptides at various final concentrations (50, 10, 1, and 0.1 micrograms (µg)/ml). Following a 4-hour incubation with 5 µg/ml brefeldin A (Sigma), T2 cells were labeled for 30 minutes at 4° C. with a saturating concentration of anti-HLA-A2.1 (BB7.2) mAb, then washed twice. Cells were then incubated for 30 minutes, 4° C. with a saturating concentration of FITC-conjugated goat IgG F(ab')$_2$ anti-mouse Ig (Caltag, San Francisco, Calif.), washed twice, fixed in PBS/1% paraformaldehyde and analyzed using a FACS Calibur® cytofluorometer (Becton Dickinson, Immunocytometry Systems, San Jose, Calif.).

The mean intensity of fluorescence (MIF) observed for each peptide concentration (after dividing by the MIF in the absence of peptide) was used as an indication of peptide binding and expressed as a "fluorescence index." Stabilization assays were performed similarly. Following initial evaluation of peptide binding at time 0, cells were washed in RPMI complete medium to remove free peptides and incubated in the continuous presence of 0.5 µg/ml brefeldin-A for 2, 4, 6 or 8 hours.

The number of stable peptide-HLA-A2.1 complexes was estimated as described above by immunofluorescence. The half time of complexes is an estimate of the time required for a 50% reduction of the MIF value at time=0.

Results

Peptides having predicted affinity for HLA-A0201 and HLA-A0301 molecules were identified from the WT1 sequence. These WT-1 native peptides were modified to generate heteroclitic peptides with increased predicted binding to HLA-A0201 and HLA-A0301 molecules, as shown in Tables 1-2. Several of the heteroclitic peptides significantly stabilized HLA-A0201 and HLA-A0301 molecules in thermostabilization assays using a TAP ½ negative cell line (T2) and Raji HLA-A0301 cells. Specifically, WT1-A1, B1, and C1 exhibited similar or increased binding compared to the corresponding native peptides WT1-A, B, and C. WT1-D1 exhibited similar or increased binding compared to corresponding native peptide WT1-D (FIG. 1A). A comparison of HLA A0301 binding of A3 WT1-A, -B, -C, and -D with each of their respective three analogues demonstrated similar binding (FIGS. 1B-5E).

Thus, heteroclitic WT1 peptides of the present invention exhibit enhanced binding to HLA class I molecules.

TABLE 1

HLA 0201-binding native peptides from WT-1 and synthetic analogues

| Name | Sequence | SEQ ID NO: | BIMAS score |
|---|---|---|---|
| WT-1 A (native) | RMFPNAPYL | 5 | 313 |
| WT-1 A1 (ANALOGUE) | YMFPNAPYL | 6 | 1444 |
| WT-1 B (native) | SLGEQQYSV | 7 | 285 |
| WT-1 B1 (ANALOGUE) | YLGEQQYSV | 8 | 1311 |
| WT-1 C (native) | ALLPAVPSL | 9 | 181 |
| WT-1 C1 (ANALOGUE) | YLLPAVPSL | 10 | 836 |
| WT-1 D (native) | NLGATLKGV | 11 | 159 |
| WT-1 D1 (ANALOGUE) | YLGATLKGV | 12 | 735 |
| WT-1 E (native) | DLNALLPAV | 13 | 11 |
| WT-1 E1 (ANALOGUE) | YLNALLPAV | 14 | 735 |
| WT-1 F (native) | GVFRGIQDV | 15 | 51 |
| WT-1 F1 (ANALOGUE) | GLRRGIQDV | 16 | 591 |
| WT-1 G (native) | KRYFKLSHL | 17 | 1 |
| WT-1 G1 (ANALOGUE) | KLYFKLSHL | 18 | 550 |
| WT-1 H (native) | ALLLRTPYS | 19 | 1 |
| WT-1 H1 (ANALOGUE) | ALLLRTPYV | 20 | 1415 |
| WT-1 J (native) | CMTWNQMNL | 21 | 15 |
| WT-1 J1 (ANALOGUE) | YMTWNQMNL | 22 | 70 |

TABLE 2

HLA 0201-binding native peptides from WT-1 and synthetic analogues

| Name | Sequence | SEQ ID | BIMAS score |
|---|---|---|---|
| A3 WT-1 A (native) | NMHQRNMTK | 23 | 40 |
| A3 WT-1 A1 (ANALOGUE) | NMYQRNMTK | 24 | 200 |
| A3 WT-1 A2 (ANALOGUE) | NMHQRVMTK | 25 | 120 |
| A3 WT-1 A3 (ANALOGUE) | NMYQRVMTK | 26 | 600 |
| A3 WT-1 B (native) | QMNLGATLK | 27 | 20 |
| A3 WT-1 B1 (ANALOGUE) | QMYLGATLK | 28 | 100 |
| A3 WT-1 B2 (ANALOGUE) | QMNLGVTLK | 29 | 60 |
| A3 WT-1 B3 (ANALOGUE) | QMYLGVTLK | 30 | 300 |
| A3 WT-1 C (native) | FMCAYPGCNK | 31 | 30 |
| A3 WT-1 C1 (ANALOGUE) | FMYAYPGCNK | 32 | 150 |
| A3 WT-1 C2 (ANALOGUE) | FMCAYPFCNK | 33 | 90 |
| A3 WT-1 C3 (ANALOGUE) | FMYAYPFCNK | 34 | 450 |
| A3 WT-1 D (native) | KLSHLQMHSR | 35 | 18 |
| A3 WT-1 D1 (ANALOGUE) | KLYHLQMHSR | 36 | 90 |
| A3 WT-1 D2 (ANALOGUE) | KLSHLQMHSK | 37 | 90 |
| A3 WT-1 D3 (ANALOGUE) | KLYHLQMHSK | 38 | 450 |

Example 2

Induction of Immune Responses Against Synthetic Peptide Analogues Derived from WT1

Materials and Experimental Methods

Peptide Stimulations

PBMC were purified from HLA-A0201 positive healthy donors and CML patients by centrifugation in Ficoll-Paque centrifugation medium (Amersham Biosciences). Peripheral blood dendritic cells (DC) were generated as follows: Monocyte-enriched PBMC fractions were isolated, using a plastic adherence technique, from total PBMC. Plastic-adherent cells were cultured further in RPMI 1640 medium (Invitrogen) with 1-5% autologous plasma, 1000 units per milliliter (U/mL) recombinant human interleukin (IL)-4 (Schering-Plough, N.J.), and 1000 U/mL recombinant human granulocyte-macrophage colony-stimulating factor (GM-CSF) (Immunex, Seattle).

On days 2 and 4 of incubation, fresh culture medium supplemented with IL-4 and GM-CSF was added. On day 6, half of the medium was exchanged for culture medium containing IL-4, GM-CSF, 10 ng/mL recombinant human tumor necrosis factor (TNF)-alpha (R&D system) and 500 ng/ml trimeric soluble CD40L (Immunex, Seattle). On day 9, cells were harvested and used as APC for antigen stimulation. The cells expressed DC-associated antigens, such as CD80, CD83, CD86, and HLA class I and class II on their cell surfaces.

T lymphocytes were isolated from the same donors by use of negative selection by depletion with an anti-CD11b, anti-CD56 and CD19 monoclonal antibody (Miltenyi, Calif.).

1×10^6 T lymphocytes were cultured with 1×10^5 autologous DC in RPMI 1640 containing 5% heat-inactivated human autologous plasma with 10 μg/mL peptide and 2 μg/ml β₂ microglobulin, 5 ng/mL recombinant human IL-7 (Genzyme), and 0.1 ng/ml IL-12 in 24 well plates.

After culture for 3 days, 20 U/ml of recombinant IL-2 (Sandoz Pharmaceutical) was added. After 10 days, 1×10^6 cells were stimulated again by adding 2×10^5 autologous magnetically isolated CD14+ monocytes together with 10 ng/ml IL-7, 20 U/ml IL-2, and 10 μg/mL peptide. In some cases, after culture for another 7 days, the cells were stimulated a third time in the same manner. After the last stimulation, CD8+ T cells were isolated magnetically, and cytotoxicity and gamma-IFN secretion were determined.

Results

Figure 2A:
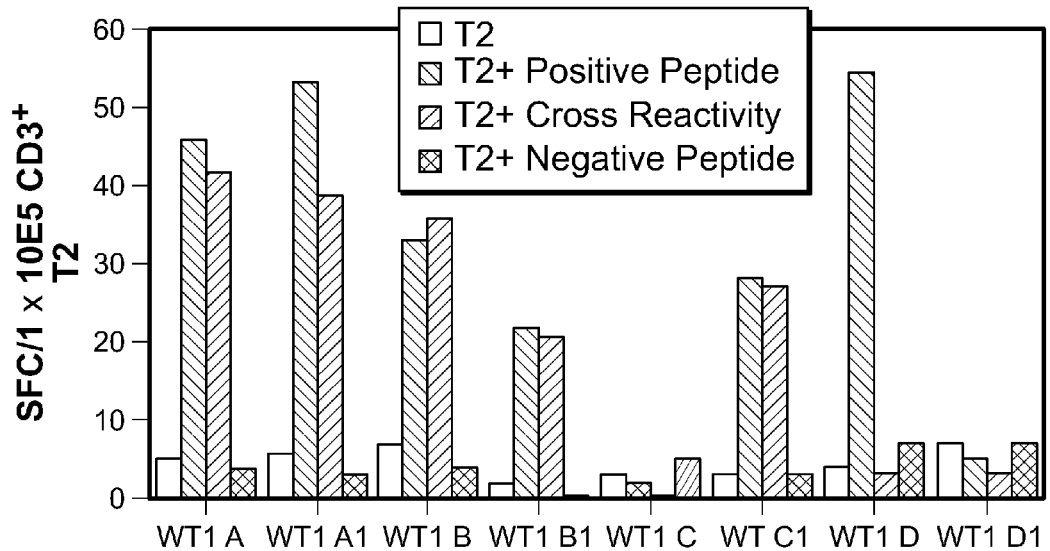
FIG. 2: CD8+/CD3+ gamma interferon (IFN) ELISPOT (A) and cytotoxicity (B) from healthy HLA A0201 donors against T2 cells pulsed with the following peptides: 1$^{st}$ bar in each series: no peptide; 2$^{nd}$ bar: same peptide used for stimulation; 3$^{rd}$ bar: corresponding native peptide; 4$^{th}$ bar: negative control peptide. X axis: peptides used for stimulations. Experiments were performed in triplicate and confirmed 3-5 times.
Figure 2B:
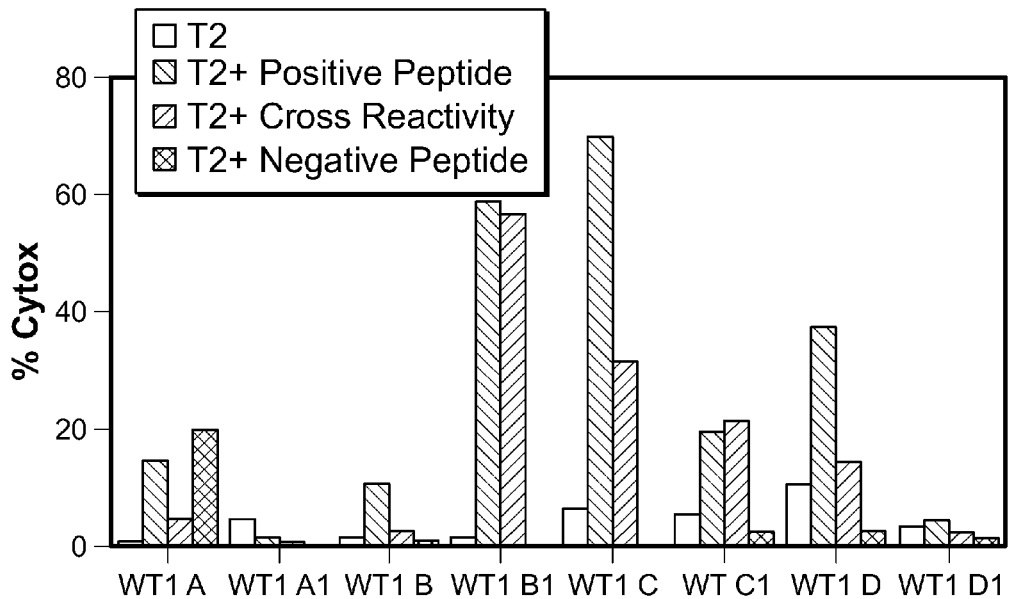
Figure 3A:
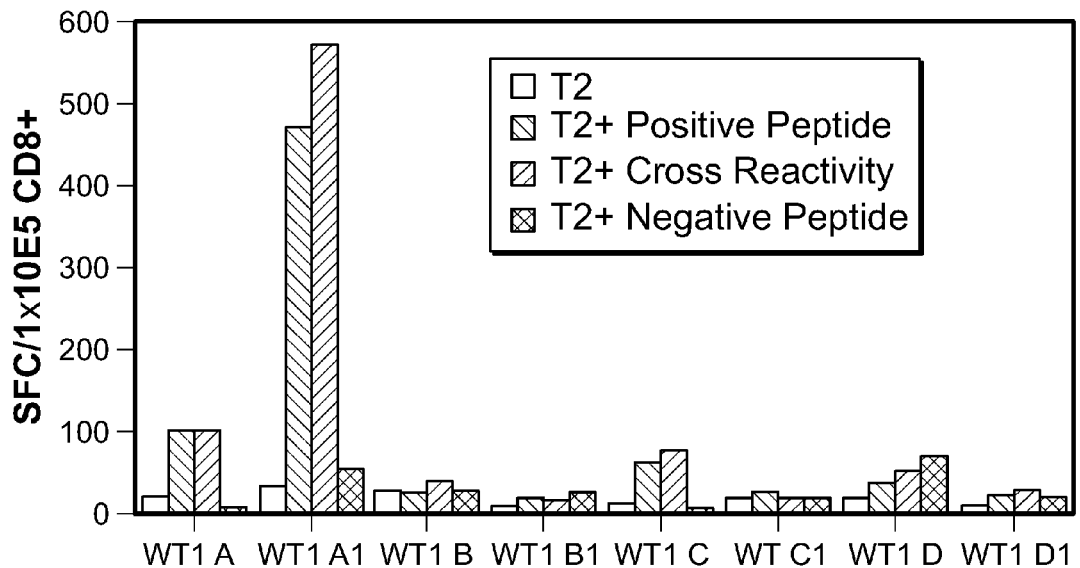
FIG. 3: CD8+ (A) and CD3+ (B-D) gamma IFN ELISPOT from healthy HLA A0201 donors using the indicated peptides-assignment of bars in each series is the same as for FIG. 2. Each subfigure in B-D represents a separate repetition of the experiment.
Figure 3B:
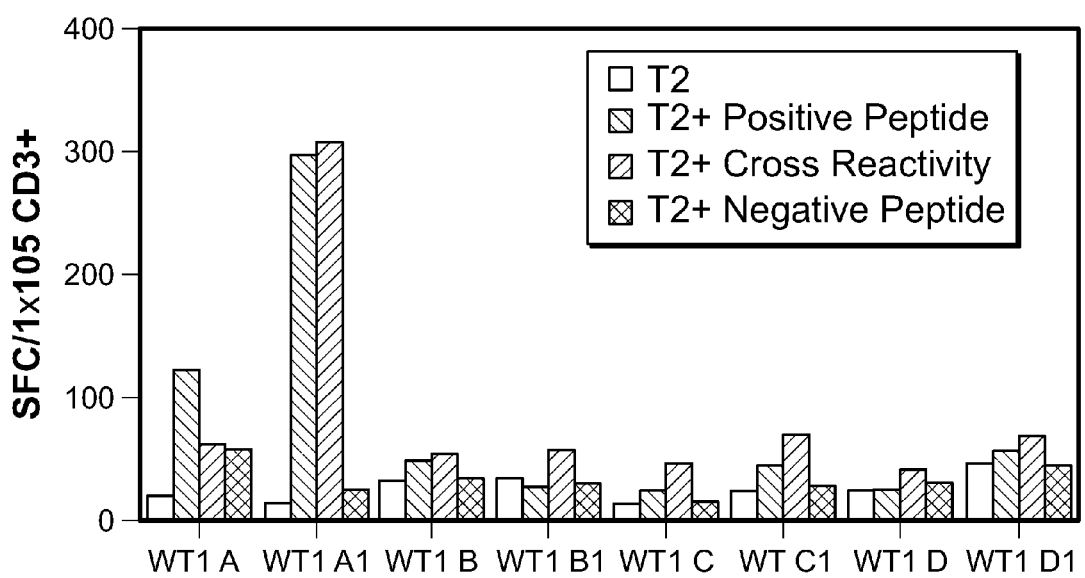
Figure 3C:
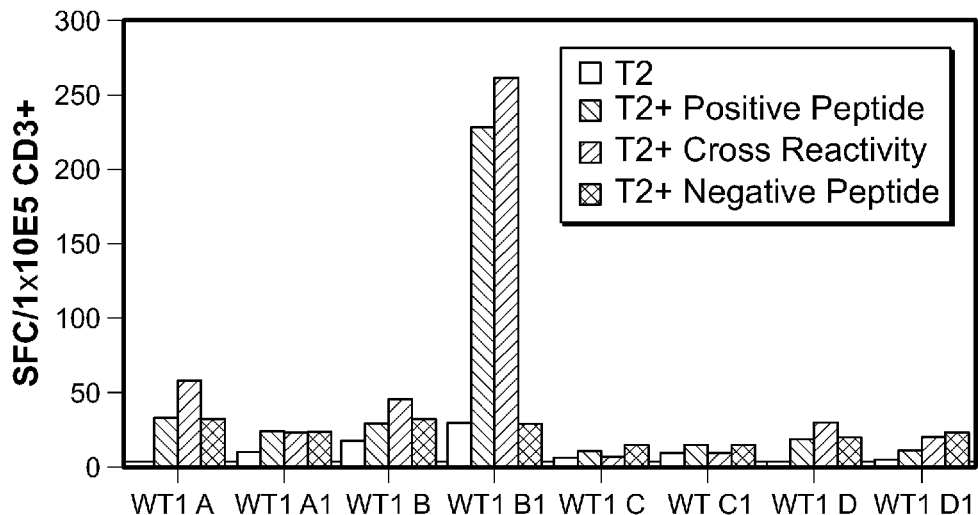
Figure 3D:
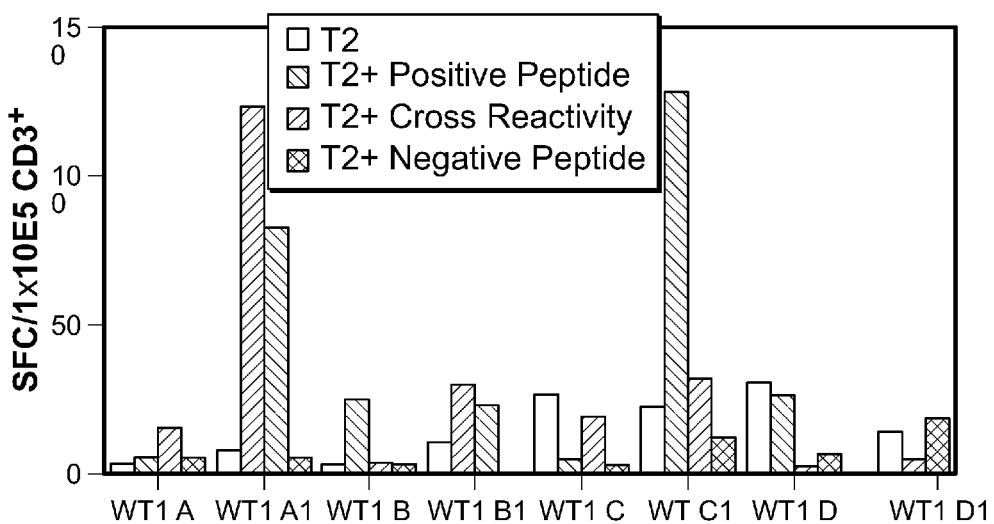
Figure 4A:
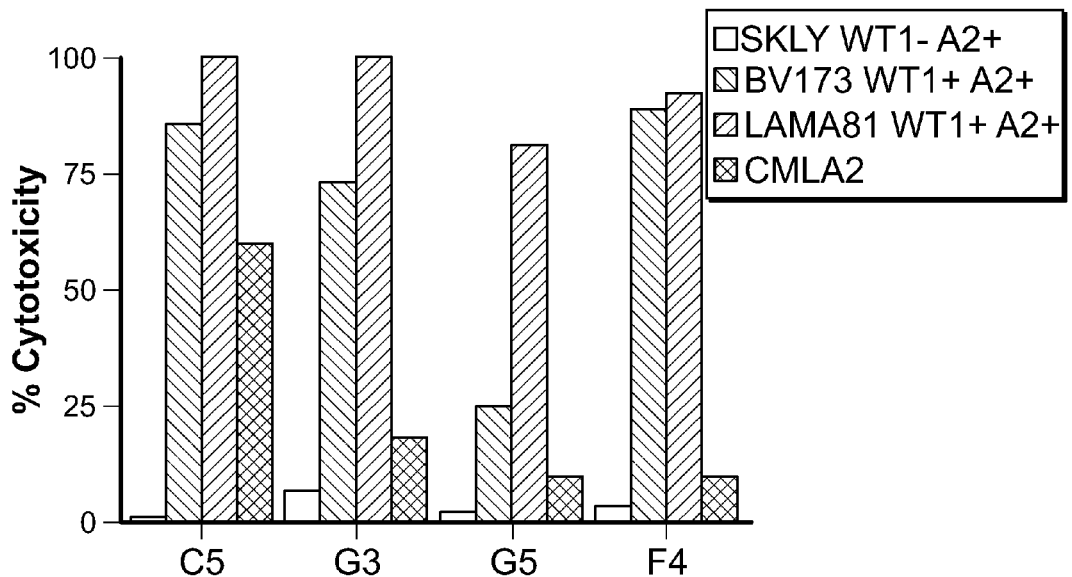
FIG. 4: Cytotoxicity assays using CD8+ T cells stimulated with synthetic WT-1 A1 peptides from a HLA A0201 donor against HLA-matched CML blasts presenting native peptide sequences. A. Bar graphs of results. 1$^{st}$ bar in each series: SKLY-16 (WT1−); 2$^{nd}$ bar: BV173 (WT1+); 3$^{rd}$ bar: LAMA81 (WT1+); 4$^{th}$ bar: CMLA (additional negative control). B. Killing curves. Squares: SKLY-16. Diamonds: 697 cells. G3, F4, C5, and G5 are T-cell clones generated from a healthy HLA-A0201 donor after multiple stimulations in vitro. Y axis:percentage of cytotoxicity. X axis:T cell:target cell ratio.
Figure 4B:
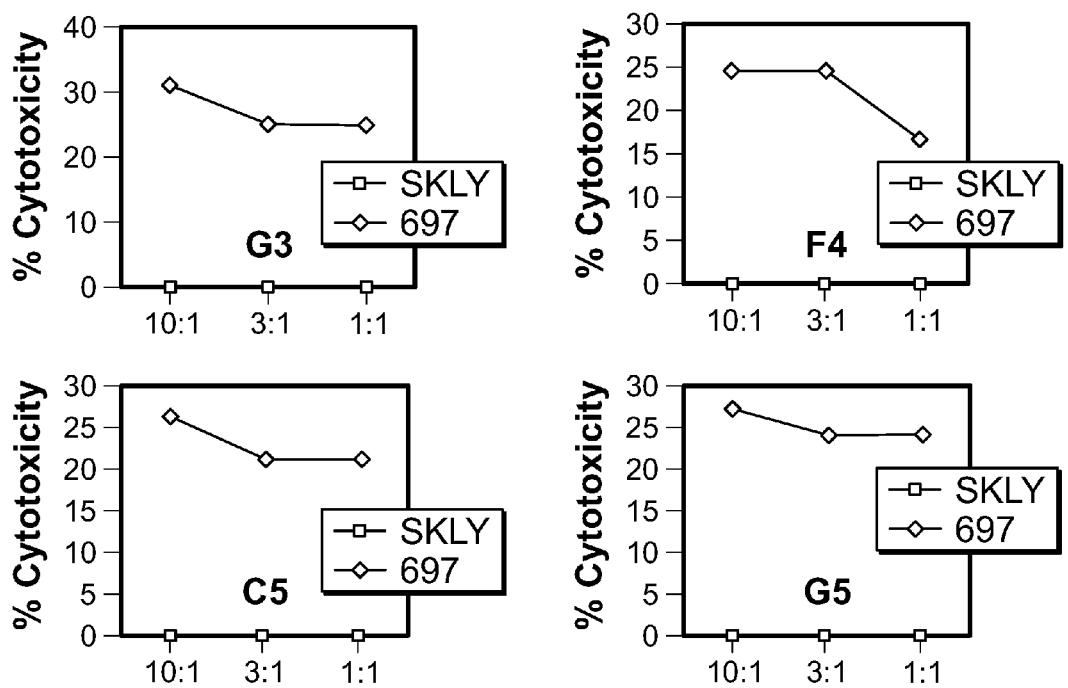

To determine the ability of heteroclitic WT1 peptides to generate immune responses against native and heteroclitic WT peptides, the CD3+ PBMC subpopulation of a healthy donor was isolated and stimulated with autologous monocyte-derived, peptide-pulsed DC, then re-stimulated with peptide-pulsed CD14+ monocytes. The presence of activated, antigen-specific T cells was then determined using pulsed, HLA-matched leukemic cell lines. Several analogue peptides generated greater immune responses (i.e. increased T cell precursor frequency, in comparison with the native peptides) by IFN, gamma ELISPOT (FIG. 2A) and chromium release assay (FIG. 2B). Similar results were observed using CD3+ (FIGS. 3B-D) and CD8+ (FIG. 3A) subpopulations of donors. Moreover, CD8+ T cells stimulated with the heteroclitic WT1 peptides cross-reacted with the native WT1 peptides and were able to lyse HLA-matched CML blasts (FIGS. 4A-B).

Thus, heteroclitic WT1 peptides of the present invention are able to generate T cells that (a) secrete inflammatory cytokines and (b) perform cytolysis in response to cells presenting WT1 peptides. In addition, the T cells generated by the heteroclitic WT1 peptides recognize both native and heteroclitic WT1 peptides Example 3

Selection of Synthetic WT1 Peptides that Bind HLA Class II Molecules

In order to identify WT1 peptides that bind to many different HLA class II molecules with relatively high affinities, allele frequencies of HLA-DRB in the North American Caucasian population were determined, using the NCBI MHC database (Wheeler D L et al, Database resources of the National Center for Biotechnology Information. Nucleic Acids Res. 2005 Jan. 1; 33:D39-45; Wheeler D L et al, Database resources of the National Center for Biotechnology Information. Nucleic Acids Res. 2006 Jan. 1; 34:D173-80). Using the SYFPEITHI epitope prediction algorithm, 2 peptides predicted to bind HLA-DRB molecules with relatively high affinities were identified from WT1 (Table 3).

TABLE 3

WT1 native peptides predicted binding to HLA-DR alleles based on SYFPEITHI algorithm (0 (low)-28 (high)).

| Peptide identifier | SEQ ID No: | DRB 101 | DRB 301 | DRB 401 | DRB 701 | DRB 1101 | DRB 1501 |
|---|---|---|---|---|---|---|---|
| Allele frequency | | 17.9% | 18.6% | 13.8% | 25.5% | 10.4% | 15.9% |
| 427 | 1 | 15 | 7 | 12 | 8 | 7 | 4 |
| 423 | 2 | 15 | 17 | 20 | 14 | 10 | 24 |
| 331 | 3 | 28 | 2 | 28 | 18 | 25 | 10 |
| 328 | 4 | 28 | 11 | 28 | 18 | 25 | 20 |

AA sequences of the peptides in Table 3 are LVRHHNMHQRNMTKL (427); RSDELVRHHNMHQRNMTKL (423); NKRYFKLSHLQMHSR (331); and PGCNKRYFKLSHLQMHSRKHTG (328).

Thus, HLA class II-binding WT1 peptides of the present invention bind to HLA class II molecules in a large percentage of the population.

Example 4

HLA Class II Molecule-Binding, WT1 Peptides Stimulate CD4+ T Cells

Materials and Experimental Methods (This and Subsequent Examples)

Preparation of DC and CD4+ Effector Cells

PBMC were Ficoll-purified from blood and resuspended at 5×10^6/ml in Ex-Vivo-15® medium (BioWhittaker, Walkersville, Md.) containing 1% autologous plasma. After a 2-hour incubation at 37° C., the non-adherent fraction was harvested and washed repeatedly with PBS, then resuspended in media containing 1×10³ IU/ml GM-CSF and 0.0032 IU/ml IL-4. On day 2 and 4, the same media was added as re-feed (i.e., ½ the volume of media, containing enough cytokines for the entire dish, was added). On day 5, 10 μg/ml of peptide was added.

On day 6, a maturation cocktail of cytokines was added, and cells were cultured for another 48 hours. The maturation cocktail consisted of: 4×10² IU/ml IL-1-beta, 0.0032 IU/ml IL-4, 1×10³ IU/ml IL-6, 1×10³ IU/ml GMCSF, 10 μg/ml TNF-alpha, and 1 μg/ml PGE2.

On day 7, DC were harvested and washed twice with RPMI, counted, aliquoted and resuspended at 1×10⁶/ml in X-vivo 15® media (without serum). Peptides were added to a final concentration of 10 μg/ml, and incubated for 2 h, 37° C. and 5% CO₂, gently re-suspending every 15 minutes, then washed twice in HESS and re-suspended in RPMI+5% autologous plasma at an appropriate concentration depending on the number of effectors isolated in the next step.

In addition, on day 7, additional PBMC were used to generate additional DC and CD3+ cells. DC were isolated from the adherent fraction and prepared as described above for the second stimulation of the effector cells on day 14. CD3+ cells were isolated from the non-adherent fraction by negative selection and stimulated with the previously prepared DC by re-suspending the CD3+ cells at a concentration of 2×10⁶ cells/ml in RPMI+5% autologous plasma, and adding DC at an effector:DC ratio of 20:1 and 10 ng/ml IL-15. Cells were then plated in 2 ml and co-incubated at 37° C. and 5% CO₂ for 1 week.

On day 14, the CD3+ cells were stimulated a second time with the second batch of DC in the same manner, except that 1×10⁶ cells/ml were mixed with DC at an effector:DC ratio of 50:1. On day 18, the same media was added as re-feed. On day 20, the DC from the previous generation were defrosted and incubated in maturation cytokines in X-vivo 15® media. On day 21, the ELISPOT assay was conducted.
ELISPOT Assay Plates were pre-wet with 30 µl/well 70% alcohol, shaking the plates to ensure coverage of the entire surface area, washed 3 times with 150 µl/well sterile PBS, then incubated overnight at 4° C. with 10 µg/ml coating antibody (anti-INF clone) in PBS, 100 µl/well, wrapped in aluminum foil. Plates were then washed 2 times with 150 µl/well PBS and 1 time with RPMI/10% autologous plasma (AP), then blocked with 150 µl/well RPMI/5% AP for 2 hours at 37° C. PBMC were suspended in RPMI/5% AP at $1\times10^6$/ml. $1\times10^5$ cells and 2 µg of the appropriate peptides were added per well, and the volume brought up to 200 µl/well with media. 1 µl/well of 2.5 mg/ml stock of PHA was added to the control wells. Plates were wrapped in aluminum foil and incubated for 20 hours at 37° C.

To develop, plates were washed 3 times with PBS/0.05% Tween 2 and 3 times with PBS. 100 µl/well anti-INF-gamma-Biotin (Clone 7-B6-1), diluted 1:500 in PBS/0.5% BSA, was added, and plates were incubated for 2 hours at 37° C. After 1 hour and 30 minutes, Avidin-peroxidase Complex (ABC) (Vectastain Elite Kit, Vector) was prepared by adding 1 drop of reagent A and 1 drop of reagent B to 10 ml of PBS/0.1% Tween20, and was stored at room temperature (rt) wrapped in aluminum foil. Plates were washed 3 times with PBS/0.05% Tween and 3 times with PBS, then 100 µl/well of Avidin-peroxidase Complex was added and plates incubated for 1 hour at rt wrapped in aluminum foil, then washed 3 times with PBS/0.05% Tween-20, followed by 3 times with PBS. 100 µl/well of substrate was added, plates were incubated for 4 minutes at rt in the dark, and the reaction was stopped with water. Wells were dried and plates stored overnight in the dark at rt. Spot numbers were automatically determined with the use of a computer-assisted video image analyzer with KS ELISPOT 4.0 software (Carl Zeiss Vision, Germany).
Preparation of Substrate To prepare solution #1: (acetate buffer), 23.4 ml dd $H_2O$, 2.3 ml 0.1 N Acetic Acid, and 5.5 ml 0.1N Sodium Acetate were mixed. To prepared solution #2, 1 tablet of AEC (Sigma) was dissolved in 2.5 ml of dimethylformamide. Then 1.25 ml of solution #2 was mixed with 23.7 ml of solution #1, 13 µl of 30% $H_2O_2$ was added, and the resulting solution mixed well and filtered using a 0.45 µm filter.
Cross Priming Experiments A $CD3^+$ in vitro stimulation was performed as described above. $2\times10^6$ immature DCs were incubated with total cellular lysate from $2\times10^6$ tumor cells that was previously prepared by 3 freeze/thaw cycles. Following an 18 hour incubation, maturation cytokines were added to the DCs as described above. $CD3^+$ cells were stimulated 3 times with these autologous mature DCs, after which T cells were tested in an IFN-gamma ELISPOT assay for reactivity against autologous, mature DCs that had been pulsed with individual $CD4^+$ peptides when in the immature state. These DCs were exposed to peptide again during the ELISPOT assay as described above.
Chromium 51 Cytotoxicity Assay The presence of specific CTL was measured in a standard 4 h-chromium release assay. Target cells were pulsed with 10 microgram (mcg)/ml of synthetic peptides overnight at 37° C. and labeled with 300 µCi of $Na_2^{51}CrO_4$ (NEN Life Science Products, Inc., Boston, Mass.). After extensive washing, target cells were incubated with T cells at an E:T ratio ranging from 100:1 to 10:1. All conditions were performed in triplicate. Plates were incubated for 4 hours at 37° C. in 5% $CO_2$. Supernatant fluids were harvested and radioactivity was measured in a gamma counter. Percent specific lysis was determined from the following formula: $100\times[$(experimental release minus spontaneous release)/(maximum release minus spontaneous release)$]$. Maximum release was determined by lysis of radiolabeled targets in 2.5% Triton X-100.
Statistics Statistical analyses were performed on Statview software (SAS Institute, Cary, N.C.) using a two-tailed unpaired t-test, with the level of statistical significance set at 0.05.

Results

To determine the ability of the HLA class II-binding WT1 peptides of the present invention to stimulate $CD4^+$ T cells, $CD4^+$ PBMC subpopulations of healthy donors were isolated and stimulated with autologous monocyte-derived, peptide-pulsed DC, then re-stimulated with peptide-pulsed $CD14^+$ monocytes. Peptide 328, and to a slightly less extent peptide 423, stimulated a significant peptide-specific CD4+ T cell response in a variety of donors with different HLA-DRB1 types, as shown by IFN-γ ELISPOT (FIG. 5). As expected, cells stimulated with RAS (irrelevant control peptide) or with APC alone did not produce IFN-γ over background levels.

Thus, HLA class II-binding WT1 peptides of the present invention are able to stimulate T cells that recognize cells presenting WT1 peptides.

Example 5

WT1-Expressing Cells Process and Present Peptides of the Present Invention

Figure 6A:
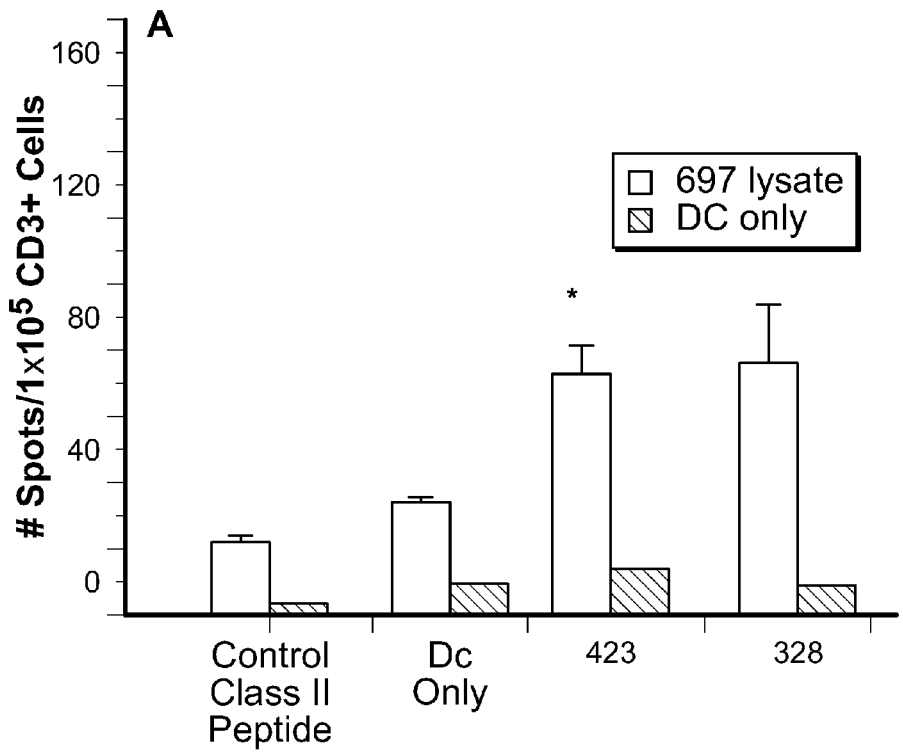
FIG. 6. Peptides of the present invention are processed, presented, and recognized by human T cells. A. CD3+ T cells from an HLA A0201/301 DRB1*1301/1302 healthy donor were stimulated with autologous DCs previously incubated with 697 tumor lysates, then challenged in an IFN-gamma ELISPOT assay with autologous DCs previously incubated with either 697 tumor lysate, individual WT1 peptides, control peptides or unpulsed DCs (X axis). B. CD3+ T cells from an HLA A0201/101, DRB1*0301/1601 healthy donor were stimulated with autologous DCs previously incubated with tumor lysates from either JMN (Black Bars), or MeWo (White Bars). T cells were challenged in an IFN-gamma ELISPOT assay with autologous DCs previously incubated with JMN or MeWo tumor lysates, individual WT1DR peptides, or control class II peptide (X axis). Hatched bars: background level of spots from autologous DCs incubated in the absence of T cells. *–P<0.05 compared to control peptides. Y axis: number of spots per 1×10⁵ CD3+ cells.
Figure 6B:
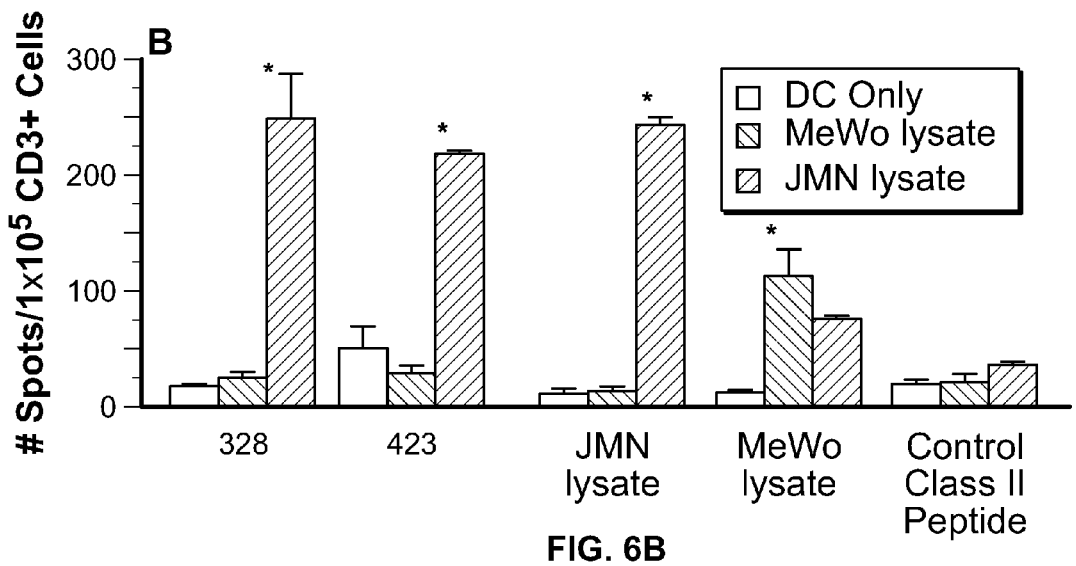

Cross-priming studies were performed to determine whether WT1-expressing cells process and present peptides of the present invention or the corresponding native peptides. Total tumor lysates were prepared from 3 different cell lines: 697 ($WT1^+$, HLA $A0201^+$), an e1a2 leukemia cell line; JMN ($WT1^+$, HLA $A0201^+$) a biphasic mesothelioma cell line, and as a control, MeWo ($WT1^-$, HLA $A0201^+$), a malignant melanoma cell line. DCs from healthy $A0201^+$ donors were incubated for 18 hours with the tumor lysates and used to stimulate autologous $CD3^+$ T cells. Following 3 stimulations, the T cells were tested for their reactivity to autologous DCs pulsed with the WT1 peptides. T cells that had been stimulated with $WT1^+$ tumor lysates recognized the individual HLA class II peptides (FIG. 6A-B), while T cells stimulated by DCs pulsed with MeWo lysate did not stimulate WT1-specific T cells. As a positive control, 697 lysate was used in the ELISPOT; this yielded spot numbers approximately equal to 423 and 328. These experiments were repeated in 5 separate donors. Stimulated T cells recognized WT1DR peptide 328 in 3/5 experiments and WT1DR 427 in all experiments. Therefore, despite the low expression of WT1 transcript in the mesothelioma cell lines (see below), WT1 CD4 epitopes of the present invention were processed and presented by HLA class II molecules of mesothelioma cells.

These findings show that peptides of the present invention are (a) taken up and presented by APC in an antigenic form; and (b) are presented by APC exposed to WT1-expressing tumor cells; and (c) APC exposed to WT1 122 and 122A1 peptides elicit the formation of T cells that recognize WT1-expressing tumor cells. Thus, WT1-expressing cells, including mesothelioma and leukemia cells, process and present peptides of the present invention or the corresponding native peptides.

Example 6

Figure 7:
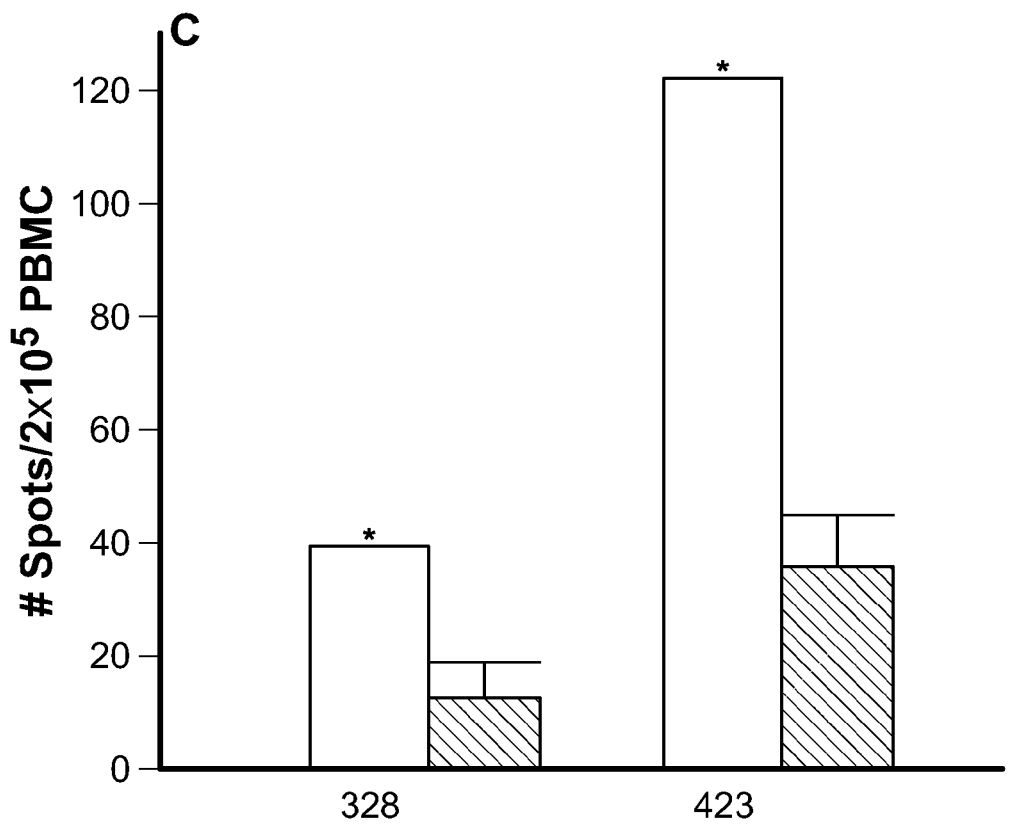
FIG. 7. CD3+ gamma interferon ELISPOT against Mesothelioma cell lines. Total PBMCs from an HLA-A0201 donor were stimulated twice with the different WT1DR peptides, then T cells were challenged in an IFN-gamma ELISPOT assay with the following: Mesothelioma H-Meso1A cell line (Black Bars; WT1+, A0201+); control melanoma MeWo cell line (WT1–, A0201+; Grey Bars). *–p≤0.01 compared to MeWo controls. Y axis: number of spots per 2×10⁵ PBMCs. X axis: peptide used for T cell stimulation.

Antigen-Specific CD4+ T Cells Generated by Peptides of the Present Invention Recognize WT1-Expressing Tumor Cells To test whether antigen-specific CD4+ T cells generated by peptides of the present invention recognize WT1-expressing tumor cells, peptide-stimulated T cells were challenged in an IFN-gamma ELISPOT with WT-1+ and -negative tumor cells. A sufficient amount of WT1 peptide was presented on the surface of the WT1+ mesothelioma tumor cell for T cells stimulated with individual WT1DR peptides to recognize mesothelioma tumor cells, compared to the control WT1 negative melanoma cells (FIG. 7). Thus, vaccination with peptides of the present invention results in generation of antigen-specific T cells with activity against WT1-expressing tumors.

Example 7

WT1 Expression in Human Mesothelioma Cell Lines

Materials and Experimental Methods

Quantitative RT-PCR for WT-1 Transcripts

Total RNA was isolated from cell lines by phenol/chloroform extraction. RNA purity was confirmed by absorbance at 260 nm. The RT reaction was adapted from protocols supplied by Applied Biosystems (Foster City, Calif.). Beginning with 1 mcg total RNA, random hexamers and reverse transcriptase were used to isolate cDNA. For the PCR reaction, cDNA was mixed with the following WT1 primers and probe: forward primer (located on exon 7): 5' CAGGCTGCAATAA-GAGATATTTTAAGCT-3' (SEQ ID No: 39); and reverse primer (located on exon 8): 5'-GAAGTCACACTGGTATG-GTTTCTCA-3' (SEQ ID No: 40); Taqman probe (located on exon 7) 5'-CTTACAGATGCACAGCAGGAAGCACACTG-3' (SEQ ID No: 41). The fluorescent WT1 probe 5'-56-FAM/CTTACAGATGCACAGCAGGAAGCACACTG/3BHQ__1/-3 (SEQ ID No: 42) was labeled with 6-carboxyfluorescein phosphoramide (FAM) as reporter dye at the 5'-end and with the quencher dye carboxytetramethylrhodamine (TAMRA) at the 3'-end (Integrated DNA Technologies, Coralville, Iowa). The parameters for the PCR reaction were: 2 minutes at 50° C., 10 min at 95° C.; followed by 50 cycles of 15 s at 95° C. and 60 s at 62° C. Each reaction was performed in triplicate, and discrepancies >1 Ct in 1 of the wells were excluded. The Q-RT-PCR reaction and fluorescence measurements were made on the Applied Biosystems 7500 Real Time® PCR System. Control ABL primers and probes were: forward 5'-TGGAGATAACACTCTAAGCATAACTAAAGGT-3 (SEQ ID No: 43; located on EnF-10030)'; reverse 5'-GATG-TAGTTGCTTGGGACCCA-3' (SEQ ID No: 44; located on ENR-1063); fluorescent probe 5'-/56 FAM/CCATTTTTG-GTTTGGGCTTCACACCATT/3BHQ__1/-3' (SEQ ID No: 45; located on ENPr-1043).

Results

Figure 8:
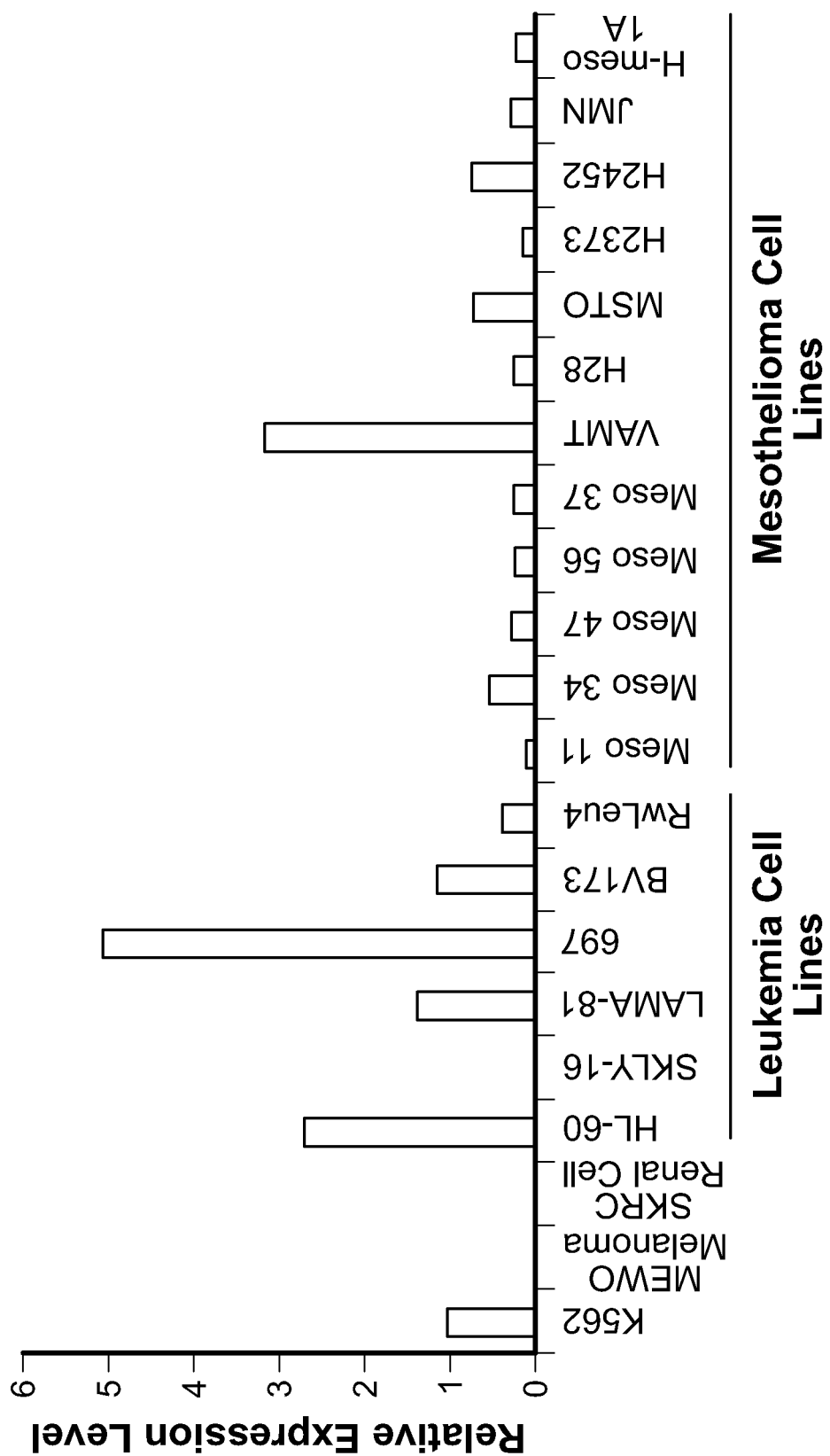
FIG. 8. CD3+ gamma IFN ELISPOT against Mesothelioma cell lines. Total PBMCs from an HLA-A0201 donor were stimulated twice with the different WT1DR peptides, then T cells were challenged in an IFN-gamma ELISPOT assay with the following: Mesothelioma H-Meso1A cell line (Black Bars; WT1+, A0201+); MeWo cell line (WT1–, A0201+; Grey Bars). *–p≤0.01 compared to MeWo controls. Y axis: number of spots per 2×10⁵ PBMCs. X axis: peptide used for T cell stimulation.

To determine WT1 expression levels in mesothelioma, WT1 transcript levels in a number of human mesothelioma cell lines (sarcomatoid, epitheliod and biphasic) were quantified by RT-PCR and compared to various leukemia cell lines with known WT1 expression. 12/12 mesothelioma cell lines expressed WT1 message, in most cases at a lower level than leukemic cell lines (FIG. 8). By contrast, melanoma (MeWo) and lymphoma (SKLY16) cell lines were WT1 negative. SK-RC-52, a human renal cell carcinoma cell line did not express WT1, despite the low expression of WT1 in adult renal podocytes. Flow cytometry analysis confirmed that all the mesothelioma cell lines expressed class II molecules, and some (JMN and H-2452) expressed class I molecules.

Thus, methods of the present invention can be used to induce immune responses and vaccination against mesothelioma cells.

What is claimed is:

1. A method of treating a subject with a WT1-expressing cancer, the method comprising administering to said subject a vaccine comprising (a) an isolated WT1 peptide consisting of the amino acid sequence RSDELVRHHNMHQRNMTKL (SEQ ID No: 2) or PGCNKRYFKLSHLQMHSRKHTG (SEQ ID No: 4) and (b) an adjuvant or a carrier, thereby treating a subject with a WT1-expressing cancer.

2. The method of claim 1, wherein said WT1-expressing cancer is a leukemia, a desmoplastic small round cell tumor, a gastric cancer, a colon cancer, a lung cancer, a breast cancer, a germ cell tumor, an ovarian cancer, a uterine cancer, a thyroid cancer, a liver cancer, a renal cancer, a kaposi's sarcoma, a sarcoma, or a hepatocellular carcinoma.

3. The method of claim 1, wherein said WT1-expressing cancer is a Wilms' tumor, an acute myelogenous leukemia (AML), a myelodysplastic syndrome (MDS), or a non-small cell lung cancer (NSCLC).

4. The method of claim 1, said vaccine comprising (a) an antigen-presenting cell and (b) the peptide sequence of SEQ ID NO: 2 or SEQ ID NO: 4.

5. The method of claim 4, wherein said WT1-expressing cancer is a leukemia, a desmoplastic small round cell tumor, a gastric cancer, a colon cancer, a lung cancer, a breast cancer, a germ cell tumor, an ovarian cancer, a uterine cancer, a thyroid cancer, a liver cancer, a renal cancer, a kaposi's sarcoma, a sarcoma, or a hepatocellular carcinoma.

6. The method of claim 4, wherein said WT1-expressing cancer is a Wilms' tumor, an acute myelogenous leukemia (AML), a myelodysplastic syndrome (MDS), or a non-small cell lung cancer (NSCLC).

7. The method of claim 1, wherein said adjuvant is QS21, Freund's incomplete adjuvant, aluminum phosphate, aluminum hydroxide, BCG, alum, a growth factor, a cytokine, a chemokine, an interleukin, Montanide ISA 51, or GM-CSF.

8. The method of claim 1 wherein the vaccine further comprises an antigen presenting cell.

9. A method of reducing an incidence of a WT1-expressing cancer, or its relapse, in a subject, the method comprising administering to said subject a vaccine comprising (a) an isolated WT1 peptide consisting of the amino acid sequence RSDELVRHHNMHQRNMTKL (SEQ ID No: 2) or PGCNKRYFKLSHLQMHSRKHTG (SEQ ID No: 4) and (b) an adjuvant or a carrier, thereby reducing an incidence of a WT1-expressing cancer, or its relapse, in a subject.

10. The method of claim 9, wherein said WT1-expressing cancer is a leukemia, a desmoplastic small round cell tumor, a gastric cancer, a colon cancer, a lung cancer, a breast cancer, a germ cell tumor, an ovarian cancer, a uterine cancer, a thyroid cancer, a liver cancer, a renal cancer, a kaposi's sarcoma, a sarcoma, or a hepatocellular carcinoma.

11. The method of claim 9, wherein said WT1-expressing cancer is a Wilms' tumor, an acute myelogenous leukemia (AML), a myelodysplastic syndrome (MDS), or a non-small cell lung cancer (NSCLC).

12. The method of claim 9, said vaccine comprising (a) an antigen-presenting cell and (b) the peptide sequence of SEQ ID NO: 2 or SEQ ID NO: 4.

13. The method of claim 12, wherein said WT1-expressing cancer is a leukemia, a desmoplastic small round cell tumor, a gastric cancer, a colon cancer, a lung cancer, a breast cancer, a germ cell tumor, an ovarian cancer, a uterine cancer, a thyroid cancer, a liver cancer, a renal cancer, a kaposi's sarcoma, a sarcoma, or a hepatocellular carcinoma.

14. The method of claim 12, wherein said WT1-expressing cancer is a Wilms' tumor, an acute myelogenous leukemia (AML), a myelodysplastic syndrome (MDS), or a non-small cell lung cancer (NSCLC).

15. The method of claim 9, wherein said adjuvant is QS21, Freund's incomplete adjuvant, aluminum phosphate, aluminum hydroxide, BCG, alum, a growth factor, a cytokine, a chemokine, an interleukin, Montanide ISA 51, or GM-CSF.

16. The method of claim 9 wherein the vaccine further comprises an antigen presenting cell.

17. A method of inducing the formation and proliferation of CTL specific for a WT1-expressing cancer, the method comprising administering to said subject a vaccine comprising (a) an isolated WT1 peptide consisting of the amino acid sequence RSDELVRHHNMHQRNMTKL (SEQ ID No: 2) or PGCNKRYFKLSHLQMHSRKHTG (SEQ ID No: 4) and (b) an adjuvant or a carrier, thereby inducing the formation and proliferation of CTL specific for a WT1-expressing cancer.

18. The method of claim 17, wherein said WT1-expressing cancer is a leukemia, a desmoplastic small round cell tumor, a gastric cancer, a colon cancer, a lung cancer, a breast cancer, a germ cell tumor, an ovarian cancer, a uterine cancer, a thyroid cancer, a liver cancer, a renal cancer, a kaposi's sarcoma, a sarcoma, or a hepatocellular carcinoma.

19. The method of claim 17, wherein said WT1-expressing cancer is a Wilms' tumor, an acute myelogenous leukemia (AML), a myelodysplastic syndrome (MDS), or a non-small cell lung cancer (NSCLC).

20. The method of claim 17, wherein said adjuvant is QS21, Freund's incomplete adjuvant, aluminum phosphate, aluminum hydroxide, BCG, alum, a growth factor, a cytokine, a chemokine, an interleukin, Montanide ISA 51, or GM-CSF.

21. The method of claim 17 wherein the vaccine further comprises an antigen presenting cell.

* * * * *

SEQUENCE LISTING

<160> NUMBER OF SEQ ID NOS: 53

<210> SEQ ID NO 1
<211> LENGTH: 15
<212> TYPE: PRT
<213> ORGANISM: Homo sapiens

<400> SEQUENCE: 1

Leu Val Arg His His Asn Met His Gln Arg Asn Met Thr Lys Leu
1               5                   10                  15

<210> SEQ ID NO 2
<211> LENGTH: 19
<212> TYPE: PRT
<213> ORGANISM: Homo sapiens

<400> SEQUENCE: 2

Arg Ser Asp Glu Leu Val Arg His His Asn Met His Gln Arg Asn Met
1               5                   10                  15

Thr Lys Leu

<210> SEQ ID NO 3
<211> LENGTH: 15
<212> TYPE: PRT
<213> ORGANISM: Homo sapiens

```
<400> SEQUENCE: 3

Asn Lys Arg Tyr Phe Lys Leu Ser His Leu Gln Met His Ser Arg
1               5                   10                  15

<210> SEQ ID NO 4
<211> LENGTH: 22
<212> TYPE: PRT
<213> ORGANISM: Homo sapiens

<400> SEQUENCE: 4

Pro Gly Cys Asn Lys Arg Tyr Phe Lys Leu Ser His Leu Gln Met His
1               5                   10                  15

Ser Arg Lys His Thr Gly
            20

<210> SEQ ID NO 5
<211> LENGTH: 9
<212> TYPE: PRT
<213> ORGANISM: Homo sapiens

<400> SEQUENCE: 5

Arg Met Phe Pro Asn Ala Pro Tyr Leu
1               5

<210> SEQ ID NO 6
<211> LENGTH: 9
<212> TYPE: PRT
<213> ORGANISM: Homo sapiens

<400> SEQUENCE: 6

Tyr Met Phe Pro Asn Ala Pro Tyr Leu
1               5

<210> SEQ ID NO 7
<211> LENGTH: 9
<212> TYPE: PRT
<213> ORGANISM: Homo sapiens

<400> SEQUENCE: 7

Ser Leu Gly Glu Gln Gln Tyr Ser Val
1               5

<210> SEQ ID NO 8
<211> LENGTH: 9
<212> TYPE: PRT
<213> ORGANISM: Homo sapiens

<400> SEQUENCE: 8

Tyr Leu Gly Glu Gln Gln Tyr Ser Val
1               5

<210> SEQ ID NO 9
<211> LENGTH: 9
<212> TYPE: PRT
<213> ORGANISM: Homo sapiens

<400> SEQUENCE: 9

Ala Leu Leu Pro Ala Val Pro Ser Leu
1               5

<210> SEQ ID NO 10
<211> LENGTH: 9
<212> TYPE: PRT
<213> ORGANISM: Homo sapiens
```

```
<400> SEQUENCE: 10

Tyr Leu Leu Pro Ala Val Pro Ser Leu
1               5

<210> SEQ ID NO 11
<211> LENGTH: 9
<212> TYPE: PRT
<213> ORGANISM: Homo sapiens

<400> SEQUENCE: 11

Asn Leu Gly Ala Thr Leu Lys Gly Val
1               5

<210> SEQ ID NO 12
<211> LENGTH: 9
<212> TYPE: PRT
<213> ORGANISM: Homo sapiens

<400> SEQUENCE: 12

Tyr Leu Gly Ala Thr Leu Lys Gly Val
1               5

<210> SEQ ID NO 13
<211> LENGTH: 9
<212> TYPE: PRT
<213> ORGANISM: Homo sapiens

<400> SEQUENCE: 13

Asp Leu Asn Ala Leu Leu Pro Ala Val
1               5

<210> SEQ ID NO 14
<211> LENGTH: 9
<212> TYPE: PRT
<213> ORGANISM: Homo sapiens

<400> SEQUENCE: 14

Tyr Leu Asn Ala Leu Leu Pro Ala Val
1               5

<210> SEQ ID NO 15
<211> LENGTH: 9
<212> TYPE: PRT
<213> ORGANISM: Homo sapiens

<400> SEQUENCE: 15

Gly Val Phe Arg Gly Ile Gln Asp Val
1               5

<210> SEQ ID NO 16
<211> LENGTH: 9
<212> TYPE: PRT
<213> ORGANISM: Homo sapiens

<400> SEQUENCE: 16

Gly Leu Arg Arg Gly Ile Gln Asp Val
1               5

<210> SEQ ID NO 17
<211> LENGTH: 9
<212> TYPE: PRT
<213> ORGANISM: Homo sapiens
```

```
<400> SEQUENCE: 17

Lys Arg Tyr Phe Lys Leu Ser His Leu
1               5

<210> SEQ ID NO 18
<211> LENGTH: 9
<212> TYPE: PRT
<213> ORGANISM: Homo sapiens

<400> SEQUENCE: 18

Lys Leu Tyr Phe Lys Leu Ser His Leu
1               5

<210> SEQ ID NO 19
<211> LENGTH: 9
<212> TYPE: PRT
<213> ORGANISM: Homo sapiens

<400> SEQUENCE: 19

Ala Leu Leu Leu Arg Thr Pro Tyr Ser
1               5

<210> SEQ ID NO 20
<211> LENGTH: 9
<212> TYPE: PRT
<213> ORGANISM: Homo sapiens

<400> SEQUENCE: 20

Ala Leu Leu Leu Arg Thr Pro Tyr Val
1               5

<210> SEQ ID NO 21
<211> LENGTH: 9
<212> TYPE: PRT
<213> ORGANISM: Homo sapiens

<400> SEQUENCE: 21

Cys Met Thr Trp Asn Gln Met Asn Leu
1               5

<210> SEQ ID NO 22
<211> LENGTH: 9
<212> TYPE: PRT
<213> ORGANISM: Homo sapiens

<400> SEQUENCE: 22

Tyr Met Thr Trp Asn Gln Met Asn Leu
1               5

<210> SEQ ID NO 23
<211> LENGTH: 9
<212> TYPE: PRT
<213> ORGANISM: Homo sapiens

<400> SEQUENCE: 23

Asn Met His Gln Arg Asn Met Thr Lys
1               5

<210> SEQ ID NO 24
<211> LENGTH: 9
<212> TYPE: PRT
<213> ORGANISM: Homo sapiens
```

```
<400> SEQUENCE: 24

Asn Met Tyr Gln Arg Asn Met Thr Lys
1               5

<210> SEQ ID NO 25
<211> LENGTH: 9
<212> TYPE: PRT
<213> ORGANISM: Homo sapiens

<400> SEQUENCE: 25

Asn Met His Gln Arg Val Met Thr Lys
1               5

<210> SEQ ID NO 26
<211> LENGTH: 9
<212> TYPE: PRT
<213> ORGANISM: Homo sapiens

<400> SEQUENCE: 26

Asn Met Tyr Gln Arg Val Met Thr Lys
1               5

<210> SEQ ID NO 27
<211> LENGTH: 9
<212> TYPE: PRT
<213> ORGANISM: Homo sapiens

<400> SEQUENCE: 27

Gln Met Asn Leu Gly Ala Thr Leu Lys
1               5

<210> SEQ ID NO 28
<211> LENGTH: 9
<212> TYPE: PRT
<213> ORGANISM: Homo sapiens

<400> SEQUENCE: 28

Gln Met Tyr Leu Gly Ala Thr Leu Lys
1               5

<210> SEQ ID NO 29
<211> LENGTH: 9
<212> TYPE: PRT
<213> ORGANISM: Homo sapiens

<400> SEQUENCE: 29

Gln Met Asn Leu Gly Val Thr Leu Lys
1               5

<210> SEQ ID NO 30
<211> LENGTH: 9
<212> TYPE: PRT
<213> ORGANISM: Homo sapiens

<400> SEQUENCE: 30

Gln Met Tyr Leu Gly Val Thr Leu Lys
1               5

<210> SEQ ID NO 31
<211> LENGTH: 10
<212> TYPE: PRT
<213> ORGANISM: Homo sapiens
```

<400> SEQUENCE: 31

Phe Met Cys Ala Tyr Pro Gly Cys Asn Lys
1               5                   10

<210> SEQ ID NO 32
<211> LENGTH: 10
<212> TYPE: PRT
<213> ORGANISM: Homo sapiens

<400> SEQUENCE: 32

Phe Met Tyr Ala Tyr Pro Gly Cys Asn Lys
1               5                   10

<210> SEQ ID NO 33
<211> LENGTH: 10
<212> TYPE: PRT
<213> ORGANISM: Homo sapiens

<400> SEQUENCE: 33

Phe Met Cys Ala Tyr Pro Phe Cys Asn Lys
1               5                   10

<210> SEQ ID NO 34
<211> LENGTH: 10
<212> TYPE: PRT
<213> ORGANISM: Homo sapiens

<400> SEQUENCE: 34

Phe Met Tyr Ala Tyr Pro Phe Cys Asn Lys
1               5                   10

<210> SEQ ID NO 35
<211> LENGTH: 10
<212> TYPE: PRT
<213> ORGANISM: Homo sapiens

<400> SEQUENCE: 35

Lys Leu Ser His Leu Gln Met His Ser Arg
1               5                   10

<210> SEQ ID NO 36
<211> LENGTH: 10
<212> TYPE: PRT
<213> ORGANISM: Homo sapiens

<400> SEQUENCE: 36

Lys Leu Tyr His Leu Gln Met His Ser Arg
1               5                   10

<210> SEQ ID NO 37
<211> LENGTH: 10
<212> TYPE: PRT
<213> ORGANISM: Homo sapiens

<400> SEQUENCE: 37

Lys Leu Ser His Leu Gln Met His Ser Lys
1               5                   10

<210> SEQ ID NO 38
<211> LENGTH: 10
<212> TYPE: PRT
<213> ORGANISM: Homo sapiens

<400> SEQUENCE: 38

Lys Leu Tyr His Leu Gln Met His Ser Lys
1               5                   10

<210> SEQ ID NO 39
<211> LENGTH: 28
<212> TYPE: DNA
<213> ORGANISM: Artificial
<220> FEATURE:
<223> OTHER INFORMATION: WT1 forward primer, exon 7

<400> SEQUENCE: 39
caggctgcaa taagagatat tttaagct                                28

<210> SEQ ID NO 40
<211> LENGTH: 25
<212> TYPE: DNA
<213> ORGANISM: Artificial
<220> FEATURE:
<223> OTHER INFORMATION: WT1 reverse primer, exon 7

<400> SEQUENCE: 40
gaagtcacac tggtatggtt tctca                                   25

<210> SEQ ID NO 41
<211> LENGTH: 29
<212> TYPE: DNA
<213> ORGANISM: Artificial
<220> FEATURE:
<223> OTHER INFORMATION: Taqman probe, exon 7

<400> SEQUENCE: 41
cttacagatg cacagcagga agcacactg                               29

<210> SEQ ID NO 42
<211> LENGTH: 29
<212> TYPE: DNA
<213> ORGANISM: Artificial
<220> FEATURE:
<223> OTHER INFORMATION: Taqman fluorescent probe, exon 7

<400> SEQUENCE: 42
cttacagatg cacagcagga agcacactg                               29

<210> SEQ ID NO 43
<211> LENGTH: 31
<212> TYPE: DNA
<213> ORGANISM: Artificial
<220> FEATURE:
<223> OTHER INFORMATION: ABL forward primer

<400> SEQUENCE: 43
tggagataac actctaagca taactaaagg t                            31

<210> SEQ ID NO 44
<211> LENGTH: 21
<212> TYPE: DNA
<213> ORGANISM: Artificial
<220> FEATURE:
<223> OTHER INFORMATION: ABL reverse primer

<400> SEQUENCE: 44
gatgtagttg cttgggaccc a                                       21

<210> SEQ ID NO 45
<211> LENGTH: 28
<212> TYPE: DNA
<213> ORGANISM: Artificial
<220> FEATURE:
<223> OTHER INFORMATION: ABL fluorescent probe

<400> SEQUENCE: 45
ccattttggg tttgggcttc acaccatt                                        28

<210> SEQ ID NO 46
<211> LENGTH: 21
<212> TYPE: PRT
<213> ORGANISM: Homo sapiens

<400> SEQUENCE: 46

Thr Glu Tyr Lys Leu Val Val Val Gly Ala Pro Gly Val Gly Lys Ser
1               5                   10                  15

Ala Leu Thr Ile Gln
            20

<210> SEQ ID NO 47
<211> LENGTH: 23
<212> TYPE: PRT
<213> ORGANISM: Homo sapiens

<400> SEQUENCE: 47

Val His Ser Ile Pro Leu Thr Ile Asn Lys Glu Glu Ala Leu Gln Arg
1               5                   10                  15

Pro Val Ala Ser Asp Phe Glu
            20

<210> SEQ ID NO 48
<211> LENGTH: 9
<212> TYPE: PRT
<213> ORGANISM: Homo sapiens

<400> SEQUENCE: 48

Ile Leu Lys Glu Pro Val His Gly Val
1               5

<210> SEQ ID NO 49
<211> LENGTH: 9
<212> TYPE: PRT
<213> ORGANISM: Homo sapiens

<400> SEQUENCE: 49

Tyr Leu Lys Ala Leu Gln Arg Pro Tyr
1               5

<210> SEQ ID NO 50
<211> LENGTH: 449
<212> TYPE: PRT
<213> ORGANISM: Homo sapiens

<400> SEQUENCE: 50

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

```
Gly Ser Leu Gly Gly Pro Ala Pro Pro Ala Pro Pro Pro Pro
     50              55              60

Pro Pro Pro Pro His Ser Phe Ile Lys Gln Glu Pro Ser Trp Gly Gly
 65              70              75              80

Ala Glu Pro His Glu Glu Gln Cys Leu Ser Ala Phe Thr Val His Phe
                 85              90              95

Ser Gly Gln Phe Thr Gly Thr Ala Gly Ala Cys Arg Tyr Gly Pro Phe
                100             105             110

Gly Pro Pro Pro Pro Ser Gln Ala Ser Ser Gly Gln Ala Arg Met Phe
                115             120             125

Pro Asn Ala Pro Tyr Leu Pro Ser Cys Leu Glu Ser Gln Pro Ala Ile
130             135             140

Arg Asn Gln Gly Tyr Ser Thr Val Thr Phe Asp Gly Thr Pro Ser Tyr
145             150             155             160

Gly His Thr Pro Ser His His Ala Ala Gln Phe Pro Asn His Ser Phe
                165             170             175

Lys His Glu Asp Pro Met Gly Gln Gln Gly Ser Leu Gly Glu Gln Gln
                180             185             190

Tyr Ser Val Pro Pro Val Tyr Gly Cys His Thr Pro Thr Asp Ser
                195             200             205

Cys Thr Gly Ser Gln Ala Leu Leu Leu Arg Thr Pro Tyr Ser Ser Asp
210             215             220

Asn Leu Tyr Gln Met Thr Ser Gln Leu Glu Cys Met Thr Trp Asn Gln
225             230             235             240

Met Asn Leu Gly Ala Thr Leu Lys Gly Val Ala Ala Gly Ser Ser Ser
                245             250             255

Ser Val Lys Trp Thr Glu Gly Gln Ser Asn His Ser Thr Gly Tyr Glu
                260             265             270

Ser Asp Asn His Thr Thr Pro Ile Leu Cys Gly Ala Gln Tyr Arg Ile
                275             280             285

His Thr His Gly Val Phe Arg Gly Ile Gln Asp Val Arg Arg Val Pro
290             295             300

Gly Val Ala Pro Thr Leu Val Arg Ser Ala Ser Glu Thr Ser Glu Lys
305             310             315             320

Arg Pro Phe Met Cys Ala Tyr Pro Gly Cys Asn Lys Arg Tyr Phe Lys
                325             330             335

Leu Ser His Leu Gln Met His Ser Arg Lys His Thr Gly Glu Lys Pro
                340             345             350

Tyr Gln Cys Asp Phe Lys Asp Cys Glu Arg Arg Phe Ser Arg Ser Asp
                355             360             365

Gln Leu Lys Arg His Gln Arg Arg His Thr Gly Val Lys Pro Phe Gln
                370             375             380

Cys Lys Thr Cys Gln Arg Lys Phe Ser Arg Ser Asp His Leu Lys Thr
385             390             395             400

His Thr Arg Thr His Thr Gly Lys Thr Ser Glu Lys Pro Phe Ser Cys
                405             410             415

Arg Trp Pro Ser Cys Gln Lys Lys Phe Ala Arg Ser Asp Glu Leu Val
                420             425             430

Arg His His Asn Met His Gln Arg Asn Met Thr Lys Leu Gln Leu Ala
                435             440             445

Leu
```

<210> SEQ ID NO 51
<211> LENGTH: 453
<212> TYPE: PRT
<213> ORGANISM: Homo sapiens

<400> SEQUENCE: 51

```
Ala Ala Glu Ala Ser Ala Glu Arg Leu Gln Gly Arg Arg Ser Arg Gly
1               5                   10                  15

Ala Ser Gly Ser Glu Pro Gln Gln Met Gly Ser Asp Val Arg Asp Leu
            20                  25                  30

Asn Ala Leu Leu Pro Ala Val Pro Ser Leu Gly Gly Gly Gly Gly Cys
        35                  40                  45

Ala Leu Pro Val Ser Gly Ala Ala Gln Trp Ala Pro Val Leu Asp Phe
50                  55                  60

Ala Pro Pro Gly Ala Ser Ala Tyr Gly Ser Leu Gly Gly Pro Ala Pro
65                  70                  75                  80

Pro Pro Ala Pro Pro Pro Pro Pro Pro Pro His Ser Phe Ile
            85                  90                  95

Lys Gln Glu Pro Ser Trp Gly Gly Ala Glu Pro His Glu Glu Gln Cys
            100                 105                 110

Leu Ser Ala Phe Thr Val His Phe Ser Gly Gln Phe Thr Gly Thr Ala
        115                 120                 125

Gly Ala Cys Arg Tyr Gly Pro Phe Gly Pro Pro Pro Ser Gln Ala
130                 135                 140

Ser Ser Gly Gln Ala Arg Met Phe Pro Asn Ala Pro Tyr Leu Pro Ser
145                 150                 155                 160

Cys Leu Glu Ser Gln Pro Ala Ile Arg Asn Gln Gly Tyr Ser Thr Val
                165                 170                 175

Thr Phe Asp Gly Thr Pro Ser Tyr Gly His Thr Pro Ser His His Ala
            180                 185                 190

Ala Gln Phe Pro Asn His Ser Phe Lys His Glu Asp Pro Met Gly Gln
        195                 200                 205

Gln Gly Ser Leu Gly Glu Gln Gln Tyr Ser Val Pro Pro Pro Val Tyr
    210                 215                 220

Gly Cys His Thr Pro Thr Asp Ser Cys Thr Gly Ser Gln Ala Leu Leu
225                 230                 235                 240

Leu Arg Thr Pro Tyr Ser Ser Asp Asn Leu Tyr Gln Met Thr Ser Gln
                245                 250                 255

Leu Glu Cys Met Thr Trp Asn Gln Met Asn Leu Gly Ala Thr Leu Lys
            260                 265                 270

Gly His Ser Thr Gly Tyr Glu Ser Asp Asn His Thr Thr Pro Ile Leu
        275                 280                 285

Cys Gly Ala Gln Tyr Arg Ile His Thr His Gly Val Phe Arg Gly Ile
    290                 295                 300

Gln Asp Val Arg Arg Val Pro Gly Val Ala Pro Thr Leu Val Arg Ser
305                 310                 315                 320

Ala Ser Glu Thr Ser Glu Lys Arg Pro Phe Met Cys Ala Tyr Pro Gly
                325                 330                 335

Cys Asn Lys Arg Tyr Phe Lys Leu Ser His Leu Gln Met His Ser Arg
            340                 345                 350

Lys His Thr Gly Glu Lys Pro Tyr Gln Cys Asp Phe Lys Asp Cys Glu
        355                 360                 365

Arg Arg Phe Ser Arg Ser Asp Gln Leu Lys Arg His Gln Arg Arg His
    370                 375                 380
```

```
Thr Gly Val Lys Pro Phe Gln Cys Lys Thr Cys Gln Arg Lys Phe Ser
385                 390                 395                 400

Arg Ser Asp His Leu Lys Thr His Thr Arg Thr His Thr Gly Glu Lys
                405                 410                 415

Pro Phe Ser Cys Arg Trp Pro Ser Cys Gln Lys Lys Phe Ala Arg Ser
            420                 425                 430

Asp Glu Leu Val Arg His His Asn Met His Gln Arg Asn Met Thr Lys
        435                 440                 445

Leu Gln Leu Ala Leu
    450

<210> SEQ ID NO 52
<211> LENGTH: 514
<212> TYPE: PRT
<213> ORGANISM: Homo sapiens

<400> SEQUENCE: 52

Met Gln Asp Pro Ala Ser Thr Cys Val Pro Glu Pro Ala Ser Gln His
1               5                   10                  15

Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
        35                  40                  45

Ser Ala Glu Arg Leu Gln Gly Arg Arg Ser Arg Gly Ala Ser Gly Ser
    50                  55                  60

Glu Pro Gln Gln Met Gly Ser Asp Val Arg Asp Leu Asn Ala Leu Leu
65                  70                  75                  80

Pro Ala Val Pro Ser Leu Gly Gly Gly Gly Cys Ala Leu Pro Val
                85                  90                  95

Ser Gly Ala Ala Gln Trp Ala Pro Val Leu Asp Phe Ala Pro Pro Gly
            100                 105                 110

Ala Ser Ala Tyr Gly Ser Leu Gly Gly Pro Ala Pro Pro Ala Pro
        115                 120                 125

Pro Pro Pro Pro Pro Pro Pro His Ser Phe Ile Lys Gln Glu Pro
    130                 135                 140

Ser Trp Gly Gly Ala Glu Pro His Glu Glu Gln Cys Leu Ser Ala Phe
145                 150                 155                 160

Thr Val His Phe Ser Gly Gln Phe Thr Gly Thr Ala Gly Ala Cys Arg
                165                 170                 175

Tyr Gly Pro Phe Gly Pro Pro Pro Ser Gln Ala Ser Ser Gly Gln
            180                 185                 190

Ala Arg Met Phe Pro Asn Ala Pro Tyr Leu Pro Ser Cys Leu Glu Ser
        195                 200                 205

Gln Pro Ala Ile Arg Asn Gln Gly Tyr Ser Thr Val Thr Phe Asp Gly
    210                 215                 220

Thr Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Val Tyr Gly Cys His Thr
            260                 265                 270

Pro Thr Asp Ser Cys Thr Gly Ser Gln Ala Leu Leu Leu Arg Thr Pro
        275                 280                 285

Tyr Ser Ser Asp Asn Leu Tyr Gln Met Thr Ser Gln Leu Glu Cys Met
    290                 295                 300
```

Thr Trp Asn Gln Met Asn Leu Gly Ala Thr Leu Lys Gly Val Ala Ala
305                 310                 315                 320

Gly Ser Ser Ser Val Lys Trp Thr Glu Gly Gln Ser Asn His Ser
            325                 330                 335

Thr Gly Tyr Glu Ser Asp Asn His Thr Thr Pro Ile Leu Cys Gly Ala
            340                 345                 350

Gln Tyr Arg Ile His Thr His Gly Val Phe Arg Gly Ile Gln Asp Val
            355                 360                 365

Arg Arg Val Pro Gly Val Ala Pro Thr Leu Val Arg Ser Ala Ser Glu
370                 375                 380

Thr Ser Glu Lys Arg Pro Phe Met Cys Ala Tyr Pro Gly Cys Asn Lys
385                 390                 395                 400

Arg Tyr Phe Lys Leu Ser His Leu Gln Met His Ser Arg Lys His Thr
            405                 410                 415

Gly Glu Lys Pro Tyr Gln Cys Asp Phe Lys Asp Cys Glu Arg Arg Phe
            420                 425                 430

Ser Arg Ser Asp Gln Leu Lys Arg His Gln Arg His Thr Gly Val
            435                 440                 445

Lys Pro Phe Gln Cys Lys Thr Cys Gln Arg Lys Phe Ser Arg Ser Asp
450                 455                 460

His Leu Lys Thr His Thr Arg Thr His Thr Gly Glu Lys Pro Phe Ser
465                 470                 475                 480

Cys Arg Trp Pro Ser Cys Gln Lys Lys Phe Ala Arg Ser Asp Glu Leu
            485                 490                 495

Val Arg His His Asn Met His Gln Arg Asn Met Thr Lys Leu Gln Leu
            500                 505                 510

Ala Leu

<210> SEQ ID NO 53
<211> LENGTH: 168
<212> TYPE: PRT
<213> ORGANISM: Homo sapiens

<400> SEQUENCE: 53

Met Gly His His His His His His His His Ser Ser Gly His
1               5                   10                  15

Ile Glu Gly Arg His Met Arg Arg Val Pro Gly Val Ala Pro Thr Leu
            20                  25                  30

Val Arg Ser Ala Ser Glu Thr Ser Glu Lys Arg Pro Phe Met Cys Ala
            35                  40                  45

Tyr Pro Gly Cys Asn Lys Arg Tyr Phe Lys Leu Ser His Leu Gln Met
        50                  55                  60

His Ser Arg Lys His Thr Gly Glu Lys Pro Tyr Gln Cys Asp Phe Lys
65                  70                  75                  80

Asp Cys Glu Arg Arg Phe Phe Arg Ser Asp Gln Leu Lys Arg His Gln
            85                  90                  95

Arg Arg His Thr Gly Val Lys Pro Phe Gln Cys Lys Thr Cys Gln Arg
            100                 105                 110

Lys Phe Ser Arg Ser Asp His Leu Lys Thr His Thr Arg Thr His Thr
            115                 120                 125

Gly Glu Lys Pro Phe Ser Cys Arg Trp Pro Ser Cys Gln Lys Lys Phe
            130                 135                 140

```
Ala Arg Ser Asp Glu Leu Val Arg His His Asn Met His Gln Arg Asn
145                 150                 155                 160

Met Thr Lys Leu Gln Leu Ala Leu
                165
```